US008883322B2

(12) United States Patent
Wu et al.

(10) Patent No.: US 8,883,322 B2
(45) Date of Patent: Nov. 11, 2014

(54) PYRIDYL CARBENE PHOSPHORESCENT EMITTERS

(75) Inventors: Yonggang Wu, Hunan (CN); Chuanjun Xia, Lawrenceville, NJ (US); James Fiordeliso, Yardley, PA (US); Suman Layek, Lawrenceville, NJ (US); Bert Alleyne, Ewing, NJ (US); Alexey Borisovich Dyatkin, Ambler, PA (US); Nasrin Ansari, Monmouth Jct., NJ (US); Scott Beers, Flemington, NJ (US); Ed Barron, Hamilton, NJ (US); Jason Brooks, Philadelphia, PA (US)

(73) Assignee: Universal Display Corporation, Ewing, NJ (US)

( * ) Notice: Subject to any disclaimer, the term of this patent is extended or adjusted under 35 U.S.C. 154(b) by 664 days.

(21) Appl. No.: 13/043,180

(22) Filed: Mar. 8, 2011

(65) Prior Publication Data
US 2012/0228583 A1    Sep. 13, 2012

(51) Int. Cl.
| H01L 51/54 | (2006.01) |
| C09K 11/06 | (2006.01) |
| C07F 15/00 | (2006.01) |
| H05B 33/10 | (2006.01) |
| H01L 51/00 | (2006.01) |
| H01L 51/50 | (2006.01) |

(52) U.S. Cl.
CPC .... *H01L 51/0085* (2013.01); *C09K 2211/1029* (2013.01); *C09K 11/06* (2013.01); *C07F 15/0033* (2013.01); *H05B 33/10* (2013.01); *C09K 2211/1044* (2013.01); *C09K 2211/1011* (2013.01); *C09K 2211/185* (2013.01); *C09K 2211/1007* (2013.01); *H01L 51/5016* (2013.01); *Y10S 428/917* (2013.01)

USPC .... 428/690; 428/917; 313/504; 257/E51.044; 544/225; 548/108

(58) Field of Classification Search
None
See application file for complete search history.

(56) References Cited

U.S. PATENT DOCUMENTS

| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |

(Continued)

FOREIGN PATENT DOCUMENTS

| EP | 0650955 | 5/1995 |
| EP | 1725079 | 11/2006 |

(Continued)

OTHER PUBLICATIONS

U.S. Appl. No. 61/356,080, filed Jun. 18, 2010.*

(Continued)

*Primary Examiner* — Marie R. Yamnitzky
(74) *Attorney, Agent, or Firm* — Duane Morris LLP

(57) ABSTRACT

Organometallic compounds comprising an imidazole carbene ligand having a N-containing ring fused to the imidazole ring are provided. In particular, the N-containing ring fused to the imidazole ring may contain one nitrogen atom or more than one nitrogen atom. These compounds may demonstrate high photoluminescent (PL) efficiency, Gaussian emission spectra, and/or short excited state lifetimes. These materials may be especially useful as blue phosphorescent emitters.

8 Claims, 3 Drawing Sheets

(56) References Cited

U.S. PATENT DOCUMENTS

| | | | |
|---|---|---|---|
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260447 A1 | 11/2005 | Brooks et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0258043 A1 | 11/2006 | Bold et al. | |
| 2006/0263635 A1 | 11/2006 | Ise | |
| 2006/0280965 A1 | 12/2006 | Kwong et al. | |
| 2007/0141397 A1* | 6/2007 | Watanabe et al. | 428/690 |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0200686 A1* | 8/2008 | Molt et al. | 548/103 |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0092854 A1* | 4/2009 | Walters et al. | 428/691 |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2011/0309346 A1* | 12/2011 | Watanabe et al. | 257/40 |
| 2012/0212125 A1* | 8/2012 | Tsai | 313/504 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | WO 01/39234 | 5/2001 |
| WO | WO 02/02714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005/113704 | 12/2005 |
| WO | WO 2005123873 | 12/2005 |
| WO | WO 2006009024 | 1/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008056746 | 5/2008 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009021126 | 2/2009 |
| WO | WO 2009/046266 | 4/2009 |
| WO | WO 2009050290 | 4/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |
| WO | WO 2011/073149 | 6/2011 |
| WO | WO 2011/158204 | 12/2011 |

OTHER PUBLICATIONS

Baldo et al., "Highly Efficient Phosphorescent Emission from Organic Electroluminescent Devices," Nature, vol. 395, 151-154, (1998).

Baldo et al., "Very high-efficiency green organic light-emitting devices based on electrophosphorescence," Appl. Phys. Lett., vol. 75, No. 1, 4-6 (1999).

Hansch, C. et al., Chem. Rev. 1991, 91, 165-195.

The International Search Report issued in PCT/US2012/027044 application.

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Tung, Yung-Liang et al., "Organic Light-Emitting Diodes Based on Charge-Neutral $Ru^{II}$ PHosphorescent Emitters," Adv. Mater., 17(8):1059-1064 (2005).

(56) References Cited

OTHER PUBLICATIONS

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

Ma, Yuguang et al., "Triplet Luminescent Dinuclear-Gold(*I*) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylene-vinylene) derivative," *Appl. Phys. Lett.*, 74(6):865-867 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi et al., "Highly Efficient Phosphorescence From Organic Light-Emitting Devices with an Exciton-Block Layer," *Appl. Phys. Lett.*, 79(2):156-158 (2001).

Wang, Y. et al., "Highly Efficient Electroluminescent Materials Based on Fluorinated Organometallic Iridium Compounds," *Appl. Phys. Lett.*, 79(4):449-451 (2001).

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic LIght-Emitting Diodes with Phosphorescent Platinum Complexes Containing N^C^N-Coordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett.*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al., A Novel Class of Phosphorescent Gold(III) Alkynyl-Based Organic Light-Emitting Devices with Tunable Color, *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota, Yasuhiko, "5,5'-Bis(dimesitylboryl)-2,2'-bithiophene and 5,5''-Bis(dimesitylboryl)-2,2':5',2''-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko,"1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al.,"1,2,4-Triazole Derivative as an Electron Transport Layer in Organic Electroluminescent Devices," *Jpn. J. Appl. Phys.*, 32:L917-L920 (1993).

Van Slyke, S. A. et al., "Organic Electroluminescent Devices with Improved Stability," *Appl. Phys. Lett.*, 69(15):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 88:171-177 (1997).

Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

\* cited by examiner

PYRIDYL CARBENE PHOSPHORESCENT EMITTERS

The claimed invention was made by, on behalf of and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the present invention is related to organometallic compounds comprising an imidazole carbene ligand having a N-containing ring fused to the imidazole ring. These compounds may be used in OLEDs to provide devices with improved efficiency and lifetime. In particular, these compounds may be especially useful as blue phosphorescent emitters.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the structure:

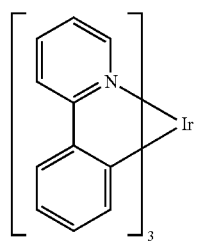

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Organometallic compounds comprising an imidazole carbene ligand having a N-containing ring fused to the imidazole ring are provided. In one aspect, the organometallic compounds comprise an imidazole carbene ligand with a diazine ring fused to the imidazole ring. The compounds comprise a ligand L having the formula:

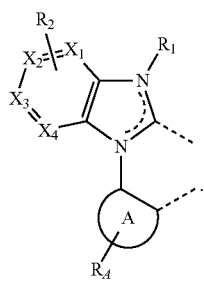

Formula I

A is a 5-membered or 6-membered carbocyclic or heterocyclic ring. Preferably, A is benzene. $R_2$ and $R_4$ may represent mono, di, tri or tetra substitutions. Each of $R_1$, $R_2$ and $R_4$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_2$ and $R_4$ are optionally joined to form a fused ring. Each of $X_1$, $X_2$, $X_3$ and $X_4$ are independently selected from the group consisting of C and N. At least two of $X_1$, $X_2$, $X_3$ and $X_4$ are N. The ligand L is coordinated to a metal M having an atomic number greater than 40. Preferably, the metal M is Ir or Pt. More preferably, the metal M is Ir. The bidentate ligand may be linked with other ligands to comprise a tridentate, tetradentate, pentadentate or hexadentate ligand.

In one aspect, $R_1$ is alkyl or cycloalkyl.

In another aspect, $R_1$ is aryl.

In one aspect, $R_4$ is an electron donating group with a Hammett constant less than 0. In another aspect, $R_4$ is selected from the group consisting of alkyl, acylamino, alkylamino, aryloxyl, and alkyloxyl.

In one aspect, the ligand L is selected from the group consisting of:

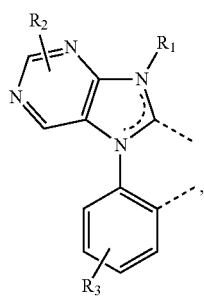

Formula II

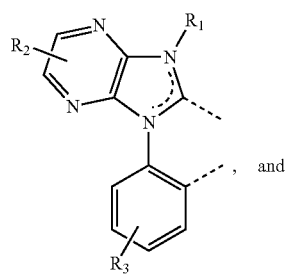

Formula III

, and

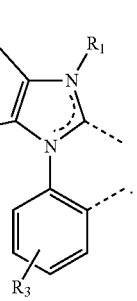

Formula IV $R_3$ may represent mono, di, tri or tetra substitutions. $R_3$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_3$ are optionally joined to form a fused ring.

In one aspect, the compound is homoleptic. In another aspect, the compound is heteroleptic.

In another aspect, the compound has a formula selected from the group consisting of:

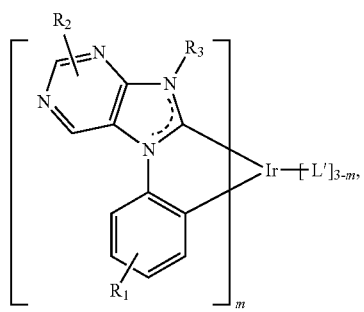

Formula V

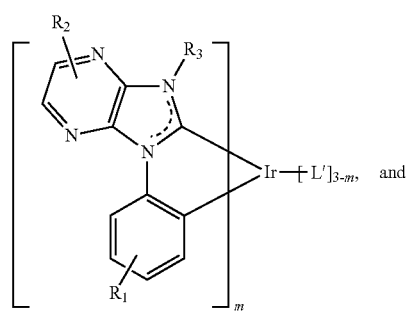

Formula VI and

Formula VII

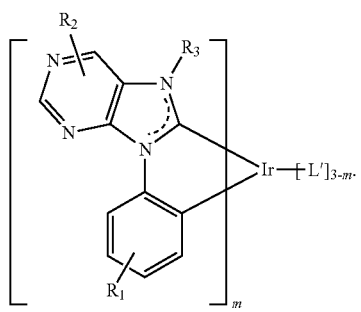

L' is a different ligand. m is 1, 2, or 3. Preferably, m is 3.

In one aspect, L' is a monoanionic bidentate ligand. In another aspect, L' is selected from the group consisting of:

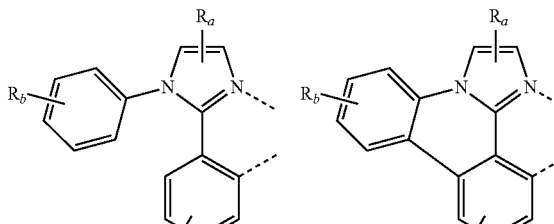

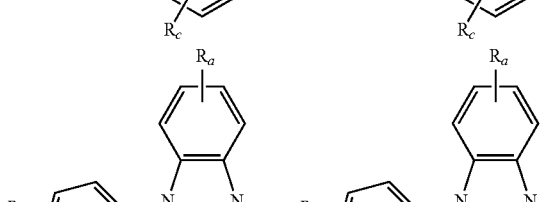

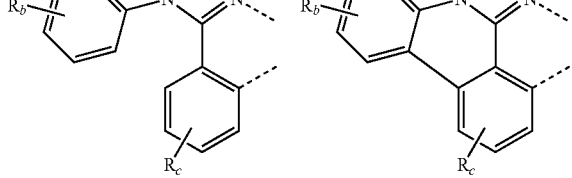

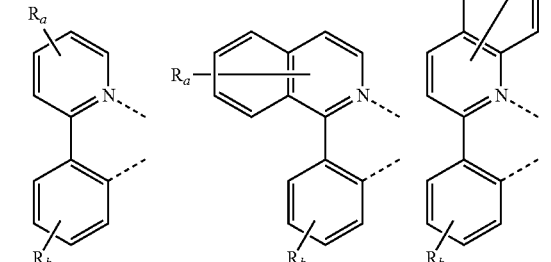

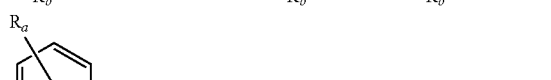

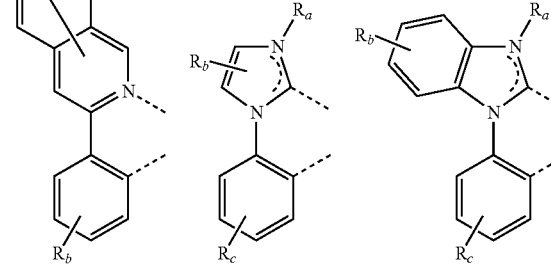

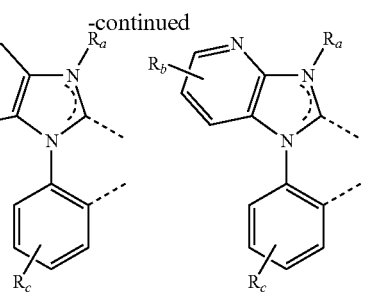

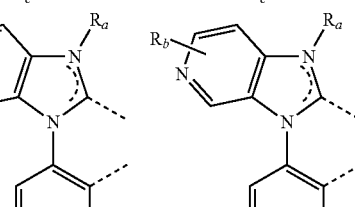

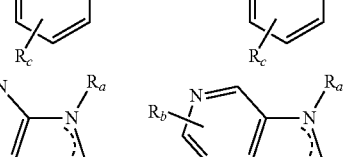

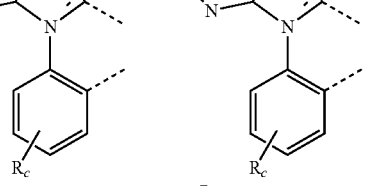

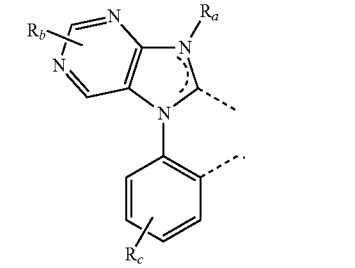

$R_a$, $R_b$, and $R_c$ may represent mono, di, tri or tetra substitutions. $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfonyl, sulfinyl, sulfonyl, phosphino, and combinations thereof. Two adjacent substituents of $R_a$, $R_b$, and $R_c$ are optionally joined to form a fused ring.

Specific, non-limiting examples of organometallic compounds comprising an imidazole carbene ligand with a diazine ring fused to the imidazole ring are provided. In one aspect, the compound is selected from the group consisting of Compound 1

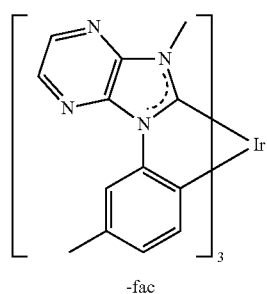

Compound 2
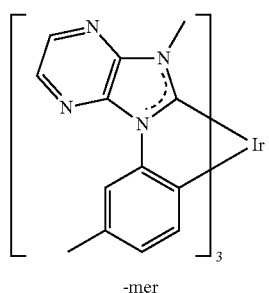
-mer
Compound 3
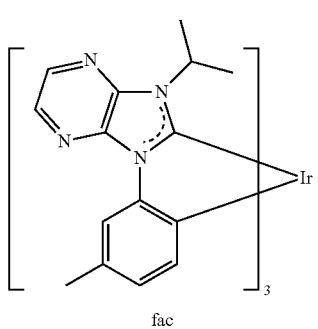
fac
Compound 4
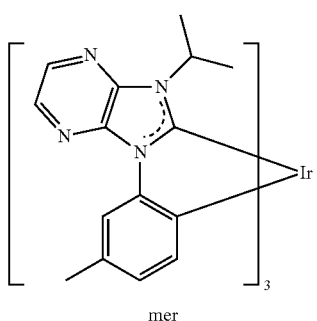
mer
Compound 5
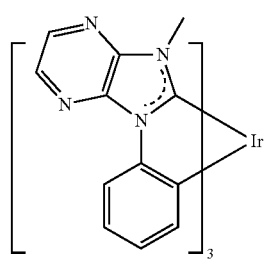
mer
Compound 6
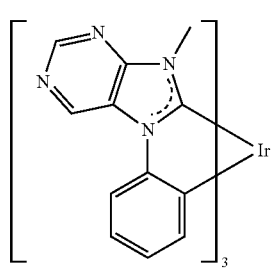
Compound 7
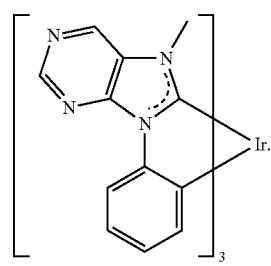
In another aspect, the organometallic compounds comprise an imidazole carbene ligand with a pyridine ring fused to the imidazole ring of the imidazole carbene ligand. Preferably, the compound is selected from the group consisting of:
Compound 8
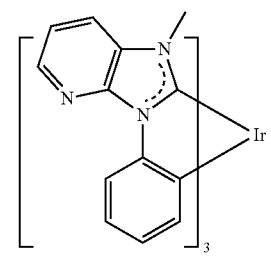
mer
Compound 9
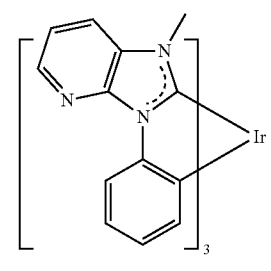
fac
Compound 10
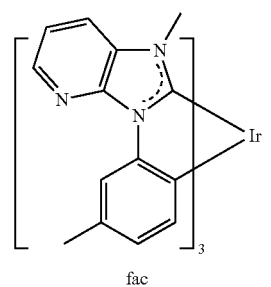
fac
Compound 11
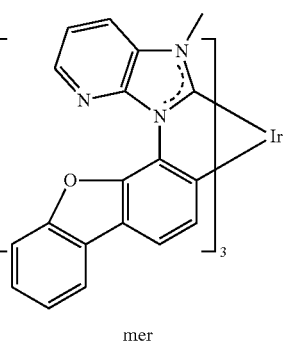
mer Compound 12
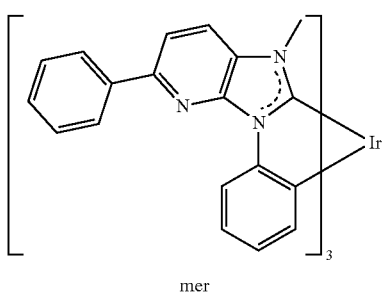
mer
Compound 13
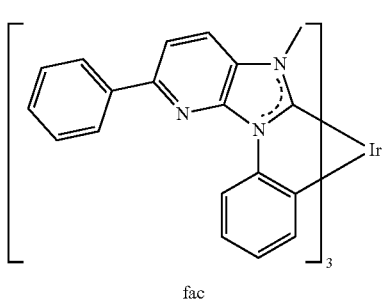
fac
Compound 14
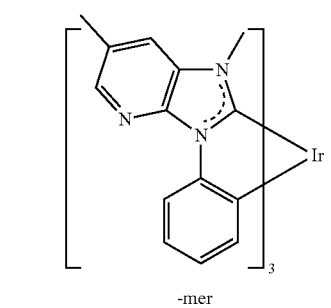
-mer
Compound 15
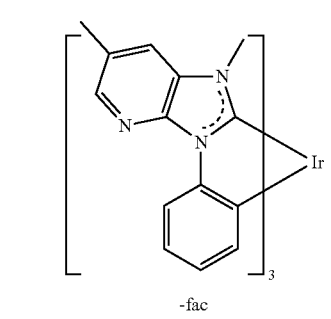
-fac
Compound 16
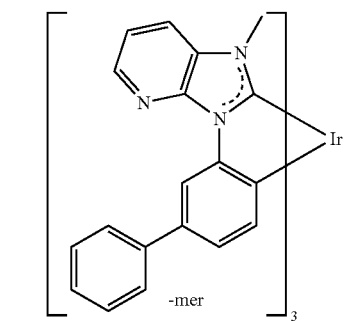
-mer
Compound 17
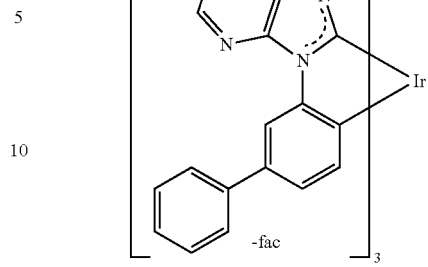
-fac
Compound 18
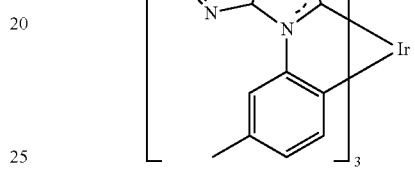
-mer
Compound 19
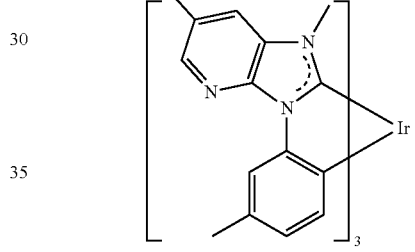
-fac
Compound 20
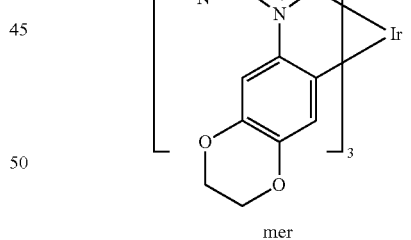
mer
Compound 21
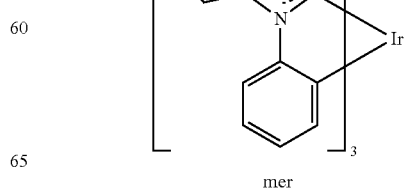
mer Compound 22
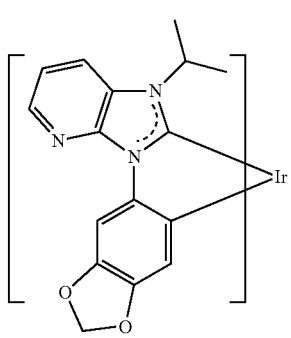
Compound 23
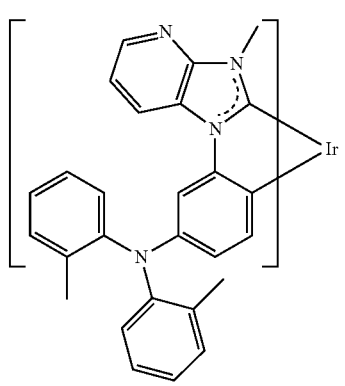
Compound 24
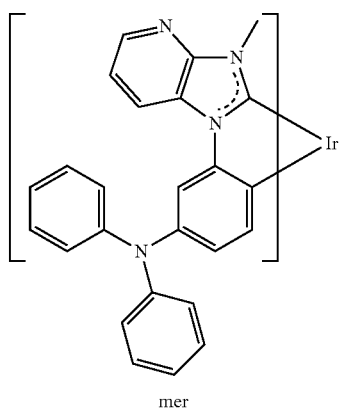
mer
Compound 25
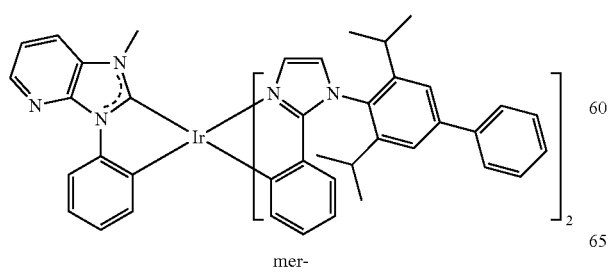
mer-
Compound 26
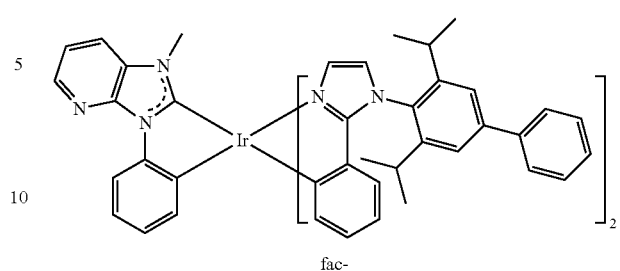
fac-
Compound 27
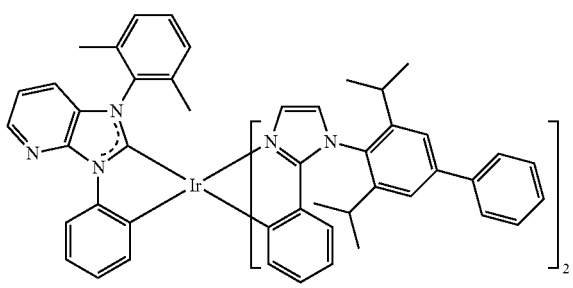
Compound 28
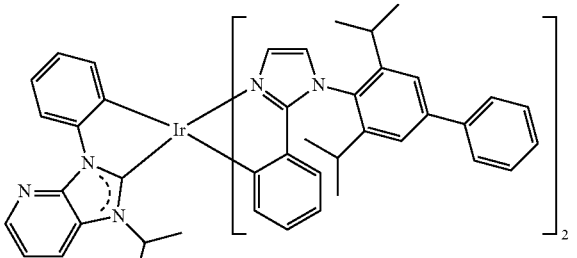
Compound 29
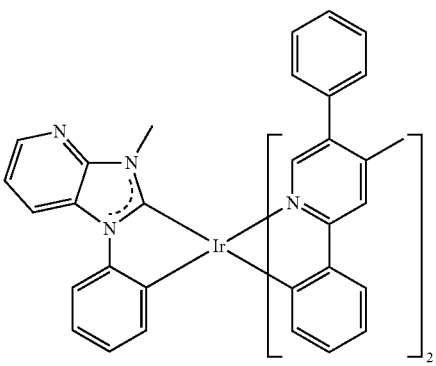

Compound 30

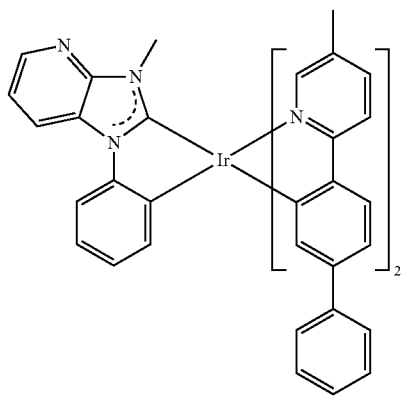

Compound 31

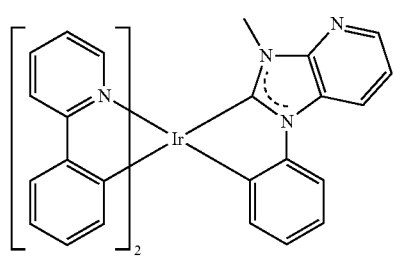

Compound 32

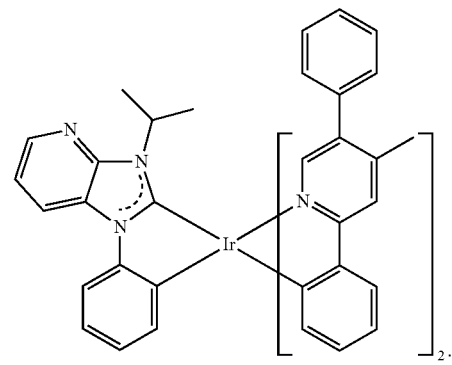

Additionally, a first device comprising an organic light emitting device is provided. The organic light emitting device further comprises an anode, a cathode and an organic layer, disposed between the anode and the cathode. The organic layer further comprises a compound comprising a ligand L having Formula I, as described above.

A is a 5-membered or 6-membered carbocyclic or heterocyclic ring. $R_2$ and $R_4$ may represent mono, di, tri or tetra substitutions. Each of $R_1$, $R_2$ and $R_4$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_2$ and $R_4$ are optionally joined to form a fused ring. Each of $X_1$, $X_2$, $X_3$ and $X_4$ are independently selected from the group consisting of C and N. At least two of $X_1$, $X_2$, $X_3$ and $X_4$ are N. The ligand L is coordinated to a metal M having an atomic number greater than 40. The bidentate ligand may be linked with other ligands to comprise a tridentate, tetradentate, pentadentate or hexadentate ligand.

Specific, non-limiting examples of devices comprising the compounds are provided. In one aspect, the compound used in the first device is selected from the group consisting of Compound 1-Compound 7.

The various specific aspects discussed above for compounds comprising a ligand L having Formula I are also applicable to a compound comprising a ligand L having Formula I that is used in the first device. In particular, specific aspects of A, M, $R_1$, $R_2$, $R_4$, $X_1$, $X_2$, $X_3$, $X_4$, L', $R_a$, $R_b$, $R_c$, Formula II, Formula III, Formula IV, Formula V, Formula VI, and Formula VII of the compound comprising a ligand L having Formula I discussed above are also applicable to a compound comprising a ligand L having Formula I that is used in the first device.

In one aspect, the organic layer is an emissive layer and the compound comprising the ligand L is an emissive dopant. In another aspect, the organic layer further comprises a host that comprises at least one of the chemical groups selected from the group consisting of

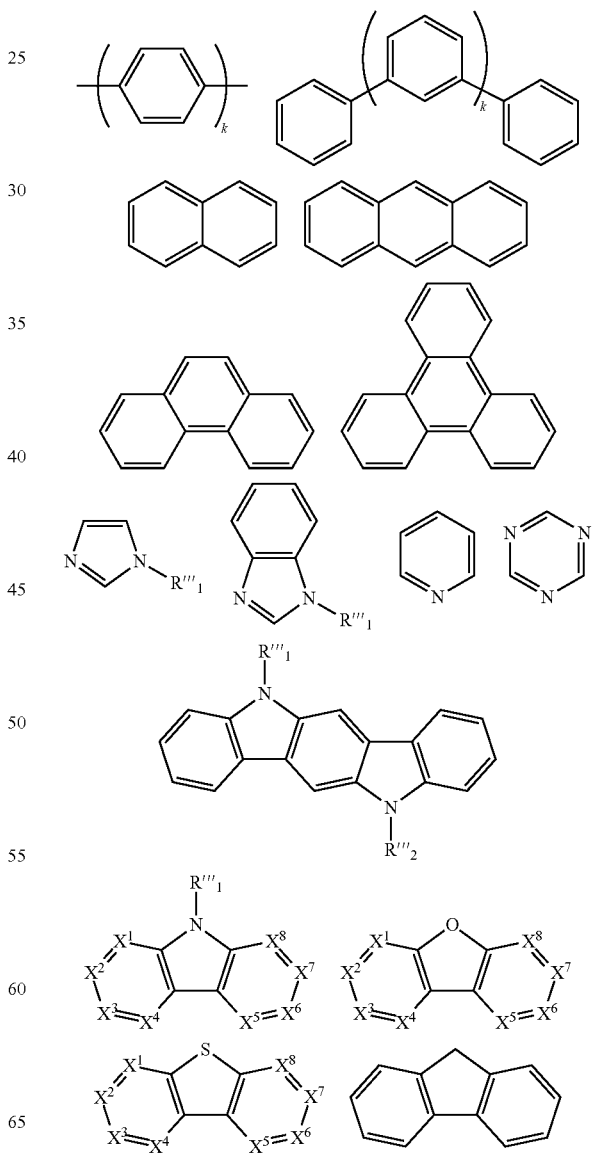

-continued

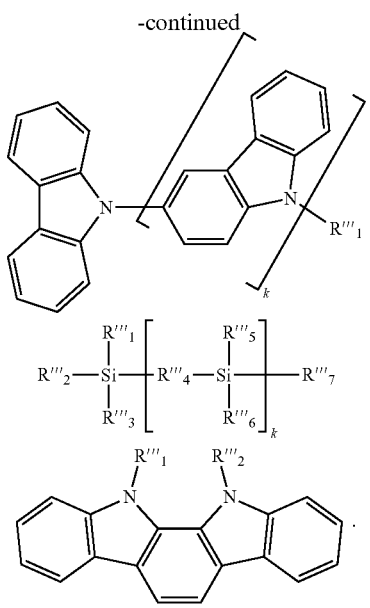

Each of $R'''_1$, $R'''_2$, $R'''_3$, $R'''_4$, $R'''_5$, $R'''_6$ and $R'''_7$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. k is an integer from 0 to 20. Each of $X^1$, $X^2$, $X^3$, $X^4$, $X^5$, $X^6$, $X^7$ and $X^8$ are independently selected from the group consisting of CH and N.

In one aspect, the first device is an organic light emitting device. In another aspect, the first device is a consumer product.

Another first device comprising an organic light emitting device is also provided. The organic light emitting device further comprises an anode, a cathode and an organic layer, disposed between the anode and the cathode. The organic layer further comprises a compound selected from the group consisting of Compound 8-Compound 32.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
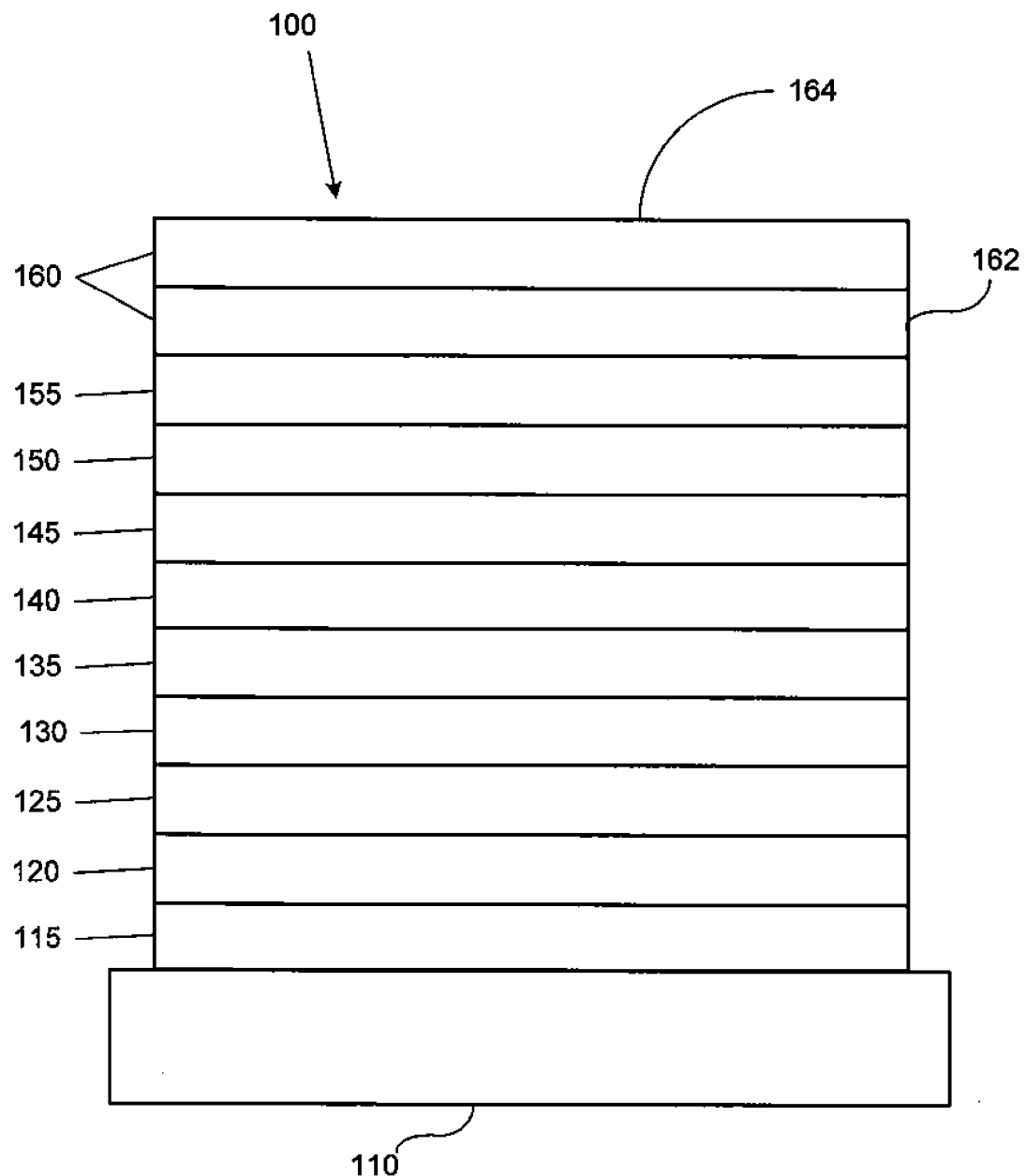
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
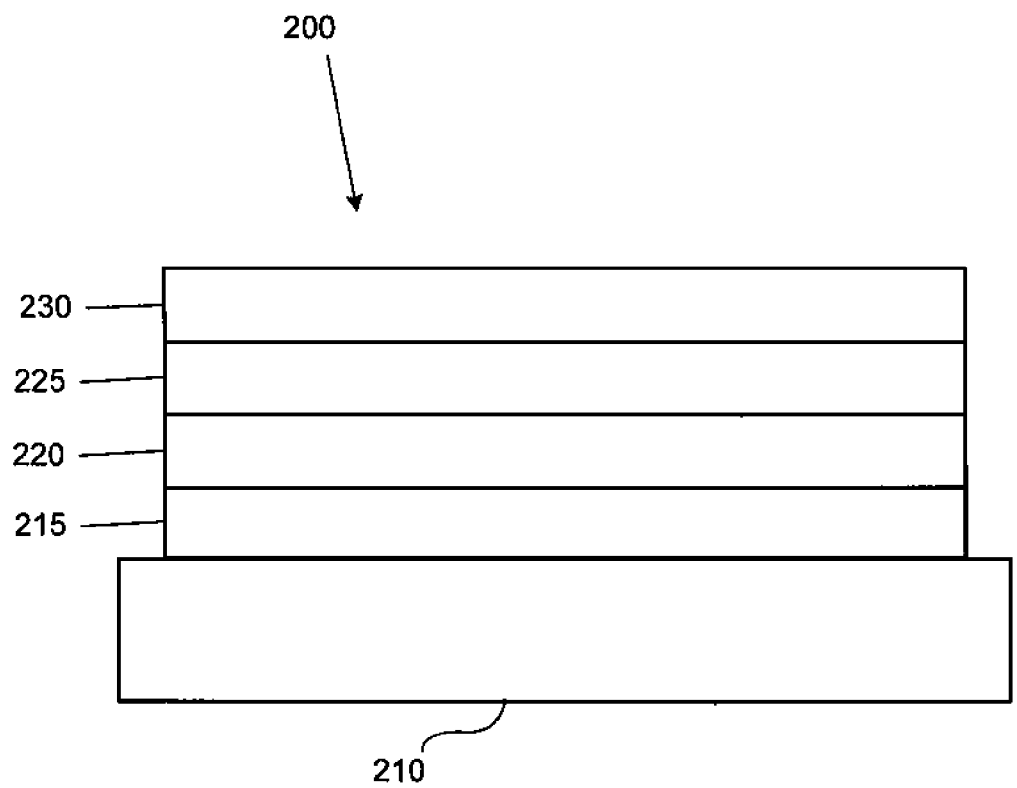
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
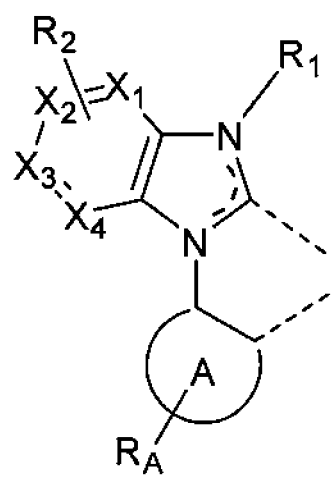
FIG. 3 shows a bidentate ligand comprising a nitrogen-containing heterocyclic ring fused to an imidazole ring bonded to another ring A.

Organometallic compounds comprising an imidazole carbene ligand having a N-containing ring fused to the imidazole ring are provided (as illustrated in FIG. 3). In one aspect, the organometallic compounds comprise an imidazole carbene ligand with a diazine ring fused to the imidazole ring, e.g., a pyrazine (1,4-diazine), a pyrimidine (1,3-diazine), or a pyridazine (1,2-diazine) ring may be fused to the imidazole ring of the imidazole carbene ligand. In another aspect, the organometallic compounds comprise an imidazole carbene ligand with a pyridine ring fused to the imidazole ring of the imidazole carbene ligand.

The compounds comprising a nitrogen-containing heterocyclic ring fused to the imidazole ring of the imidazole carbene ligand may have very strong photoluminescent properties. In particular, these compounds may demonstrate high photoluminescent (PL) efficiency, Gaussian emission spectra, and/or short excited state lifetimes. Therefore, these compounds may be useful as emitters in OLEDs. In particular, these materials may be especially useful as blue phosphorescent emitters, because of their desirable deep blue emission characteristics.

N-heterocylic imidazole carbene complexes with fused nitrogen-containing rings may have strong photoluminescent properties as compared to corresponding imidazole and benzimidazole carbene compounds. The compounds disclosed herein may have high PL efficiency, short radiative lifetime, and/or Gaussian emission characteristic of strong MLCT character. In comparison, the emission property of the imidazole and benzimidazole carbenes without nitrogen-containing fused rings may have longer radiative lifetime and lower PL efficiency. In addition, a nitrogen-containing heterocylic ring fused to the imidazole can tune the HOMO/LUMO energy levels and change emission color of the complex.

Without being bound by theory, it is believed that increasing the number of nitrogen atoms in the heterocyclic ring that is fused to the carbene may further increase the charge transfer character of the emission. For example, several inventive compounds having two nitrogen atoms in the ring fused to the carbene, e.g., Compounds 1-5, demonstrate a substantial red-shifting effect relative to benzimidazole carbenes, e.g., Comparative Compounds A and B, which only emit in the LTV region, but not in the desired visible region. One possible benefit of red-shifting using this method is that the degree of MLCT emission is not affected. The compounds having two nitrogen atoms in the ring fused to the carbene may have high quantum yield with short excited state lifetime. In particular, the Gaussian emission profile of these compounds may show the increased charge transfer character. On the other hand, red shifting the emission through increasing ligand conjugation in the imidazole carbene ring results in long excited state lifetime and more ligand based emission.

In addition, a subset of the compounds provided may be advantageously red-shifted by incorporating electron donating groups to the cyclometallated ring. This method of red-shifting may raise the HOMO energy of the material, allowing for better charge trapping property while maintaining desired optical properties, such as short excited state lifetime. In contrast, compounds that are red-shifted by different methods may have limitations. For example, compounds that are red-shifted by extending conjugation through aromatic substitution in the cyclometallated ring may have very long excited state lifetimes.

Red-shifting the compounds by extending the conjugation with aromatic rings in the cyclometallated ring may result in more ligand-based emission with a long excited state lifetime, whereas red-shifting the emission with electron donating groups can red-shift the emission while maintaining strong MLCT properties and short excited state lifetime. For example, each of Compounds 12, 13, 16, and 17 have a very long excited state lifetime and a large amount of ligand based emission. Compound 20 has electron-donating groups that red-shift the emission but the compound maintains strong MLCT properties and a short excited state lifetime. Red-shifting the emission with electron donating groups can also raise the HOMO energy, which can allow for the compound to be a better charge trap. As a result, these compounds may provide devices having improved efficiency.

The compounds described herein emit with high energy, and therefore may be particularly useful as deep blue phosphorescent emitters in OLEDs.

The photoluminescent properties of several of the inventive compounds are summarized below in Table 1.

TABLE 1

| | 77 K (nm) | RT (nm) | RT in PMMA (nm) | 77 K transient (μs) | PLQY in PMMA (%) |
|---|---|---|---|---|---|
| Compound 1 | 459 | 512 (G) | 486 (G) | 6 | 76 |
| Compound 2 | 520 (G) | — | 525 (G) | 2.2 | 64 |
| Compound 3 | 461 | — | 486 (G) | 4.5 | 80 |
| Compound 4 | 527 (G) | — | 525 (G) | 2.3 | 65 |
| Compound 5 | 500 (G) | 550 (G) | 505 | 2.18 | 73 |
| Compound 8 | 415 (G) | 469 (G) | 446 (G) | 1.3 | 73 |
| Compound 9 | 392 | 422 (G) | 416 (G) | 6.3 | 39 |
| Compound 10 | 398 | 435 (G) | 427 (G) | 3.8 | 57 |
| Compound 11 | 441 | 445 | 445 | 30 | 56 |
| Compound 12 | 461 | 468 | 464 | 290 | 80 |
| Compound 13 | 463 | 468 | 467 | 421 | 80 |
| Compound 14 | 418 (G) | 471 (G) | — | 1.3 | — |
| Compound 15 | 402 | 431 (G) | — | 3.5 | — |
| Compound 16 | 460 | 465 | — | 223 | — |
| Compound 17 | 454 | 460 | — | 240 | — |
| Compound 18 | 432 (G) | 486 (G) | — | 1.3 | — |
| Compound 19 | 402 | 435 (G) | — | 3.2 | — |
| Compound 20 | 433 (G) | 484 (G) | 452 (G) | 1.9 | 78 |
| Compound 21 | 406 | 449 (G) | 431 (G) | 1.2 | 73 |
| Compound A (comparative) | 380 | 385 | 387 | 3.2 | 48 |

(G) is Gaussian emission. 77K and room temperature (RT) emission in 2-methyl THF. PMMA films at 100:5 weight percent, dissolved in toluene and drop cast on quartz substrate. 77K transient also in 2-Methyl THF.

Organometallic compounds comprising an imidazole carbene ligand having a N-containing ring fused to the imidazole ring are provided. In one aspect, the organometallic compounds comprise an imidazole carbene ligand with a diazine ring fused to the imidazole, e.g., a pyrazine (1,4-diazine), a pyrimidine (1,3-diazine), or a pyridazine (1,2-diazine) ring may be fused to the imidazole ring of the imidazole carbene ligand. The compounds comprise a ligand L having the formula:

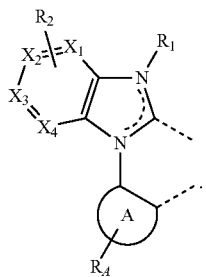

Formula I

A is a 5-membered or 6-membered carbocyclic or heterocyclic ring. Preferably, A is benzene. $R_2$ and $R_A$ may represent mono, di, tri or tetra substitutions. Each of $R_1$, $R_2$ and $R_A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_2$ and $R_A$ are optionally joined to form a fused ring. Each of $X_1$, $X_2$, $X_3$ and $X_4$ are independently selected from the group consisting of C and N. At least two of $X_1$, $X_2$, $X_3$ and $X_4$ are N. The ligand L is coordinated to a metal M having an atomic number greater than 40. Preferably, the metal M is Ir or Pt. More preferably, the metal M is Ir. The bidentate ligand may be linked with other ligands to comprise a tridentate, tetradentate, pentadentate or hexadentate ligand.

In one aspect, $R_1$ is alkyl or cycloalkyl.

In another aspect, $R_1$ is aryl.

The Hammett sigma constant is a measurement of electron withdrawing and donating ability of a given substituent. See, e.g., Hansch, C. et al., Chem. Rev. 1991, 91, 165-195. A large negative sigma value implies high electron donating power relative to H. In one aspect, $R_A$ is an electron donating group with a Hammett sigma constant less than 0. Without being bound by theory, it is believed that incorporating an electron donating group having a Hammett sigma constant less than 0 may raise the HOMO energy level of the compound, which has a deep HOMO. In another aspect, $R_A$ is selected from the group consisting of alkyl, arylamino, alkylamino, aryloxyl, and alkyloxyl.

In one aspect, the ligand L is selected from the group consisting of:

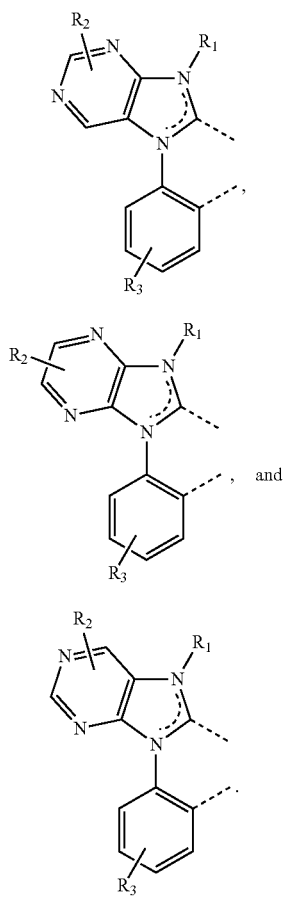

Formula II

Formula III

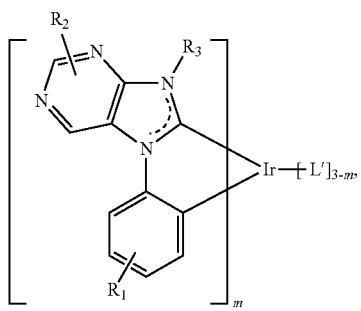

Formula IV $R_3$ may represent mono, di, tri or tetra substitutions. $R_3$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_3$ are optionally joined to form a fused ring.

In one aspect, the compound is homoleptic. In another aspect, the compound is heteroleptic.

In another aspect, the compound has a formula selected from the group consisting of:

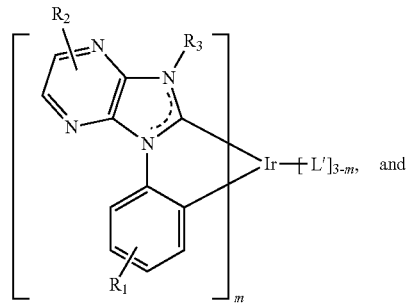

Formula V

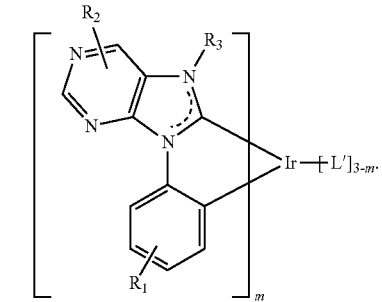

Formula VI

Formula VII $L'$ is a different ligand. m is 1, 2, or 3. Preferably, m is 3.

In one aspect, $L'$ is a monoanionic bidentate ligand. In another aspect, $L'$ is selected from the group consisting of:

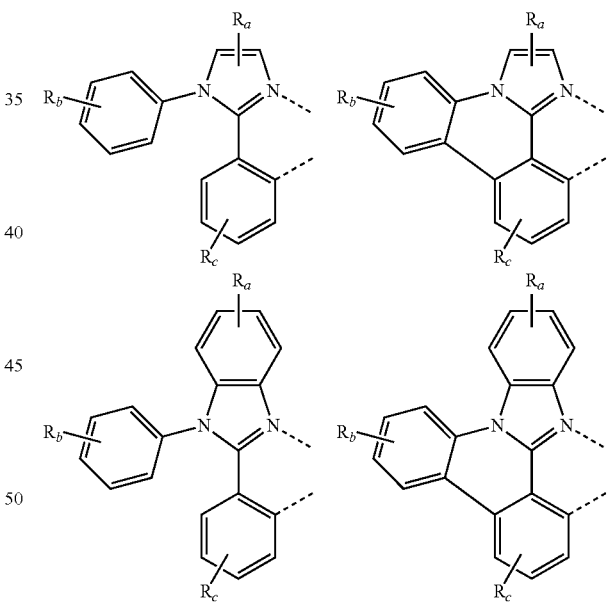

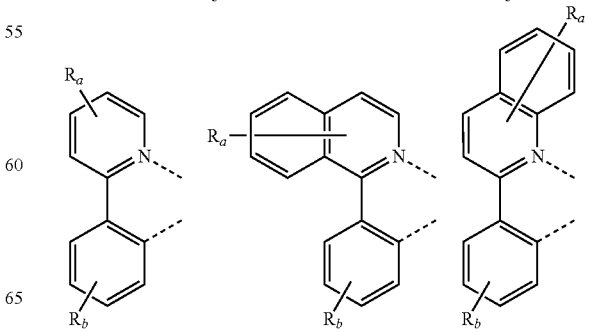

-continued

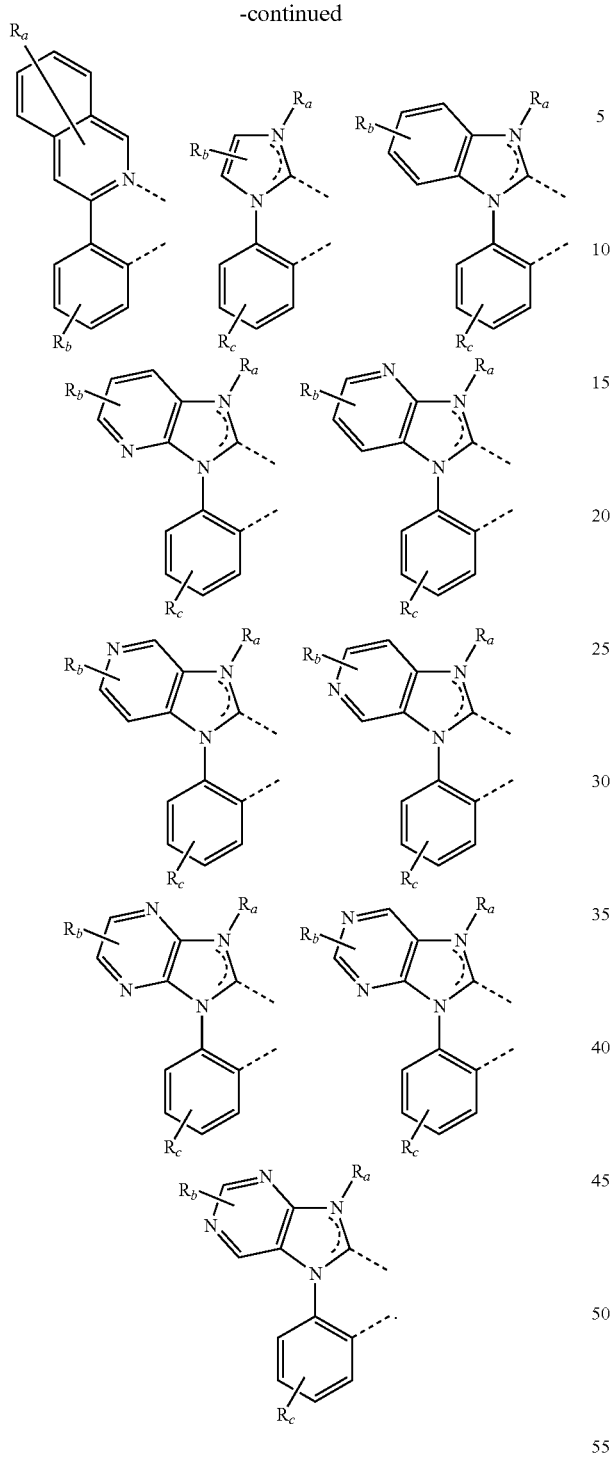

$R_a$, $R_b$, and $R_c$, may represent mono, di, tri or tetra substitutions. $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphino, and combinations thereof. Two adjacent substituents of $R_a$, $R_b$, and $R_c$ are optionally joined to form a fused ring.

Specific, non-limiting examples of organometallic compounds comprising an imidazole carbene ligand with a diazine ring fused to the imidazole ring are provided. In one aspect, the compound is selected from the group consisting of:

Compound 1

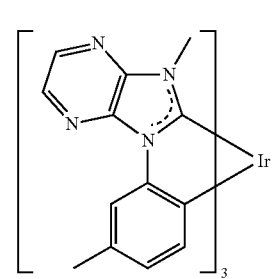

-fac

Compound 2

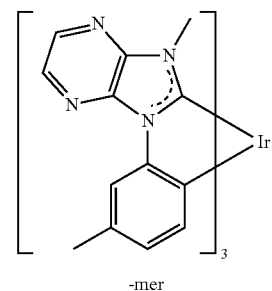

-mer

Compound 3

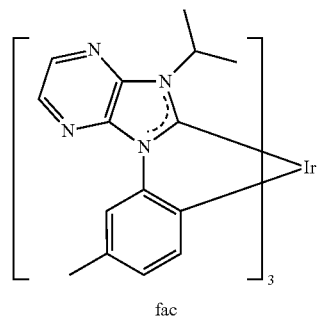

fac

Compound 4

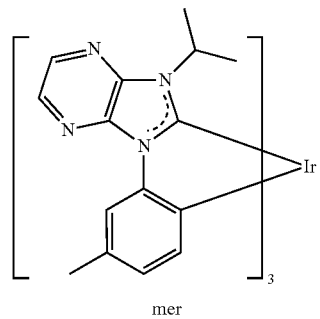

mer

Compound 5

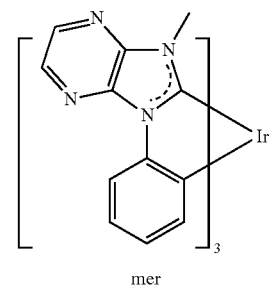

mer

Compound 6
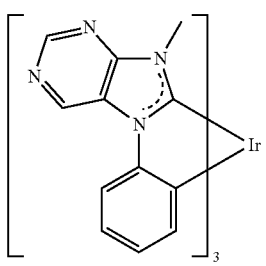
Compound 7
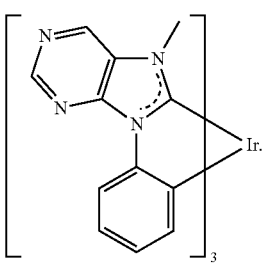
In another aspect, the organometallic compounds comprise an imidazole carbene ligand with a pyridine ring fused to the imidazole ring of the imidazole carbene ligand. Preferably, the compound is selected from the group consisting of:
Compound 8
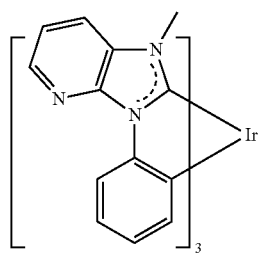
mer
Compound 9
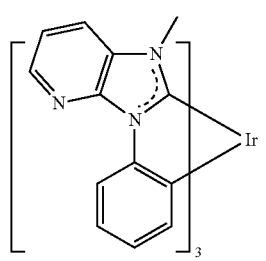
fac
Compound 10
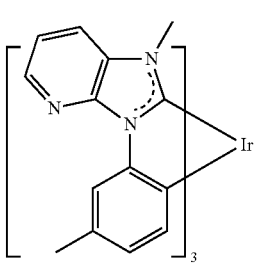
fac
Compound 11
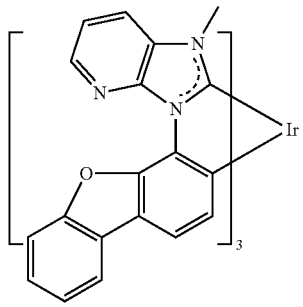
mer
Compound 12
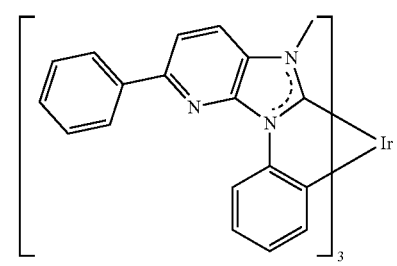
mer
Compound 13
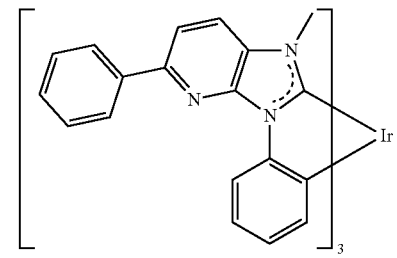
fac
Compound 14
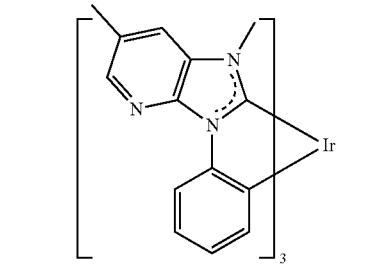
-mer
Compound 15
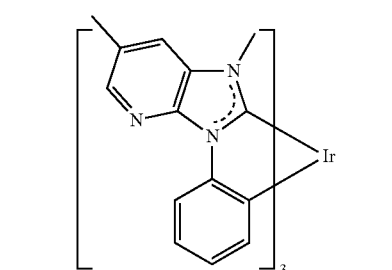
-fac Compound 16
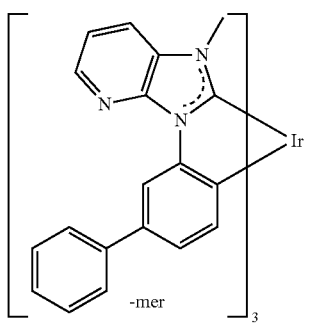
-mer
Compound 17
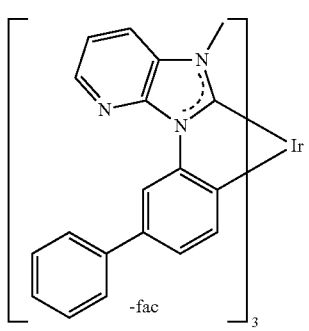
-fac
Compound 18
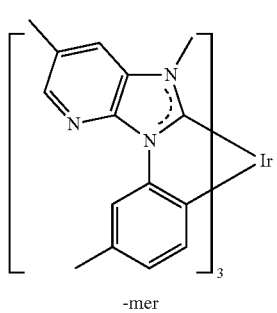
-mer
Compound 19
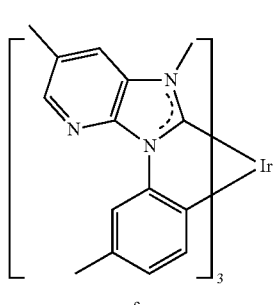
-fac
Compound 20
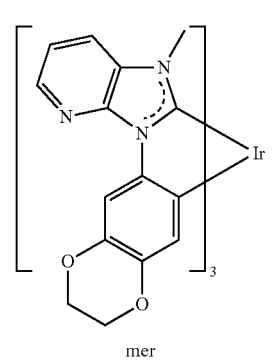
mer
Compound 21
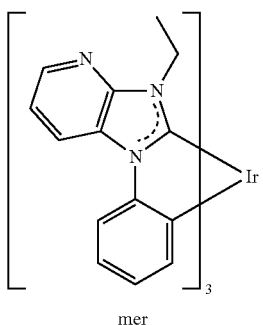
mer
Compound 22
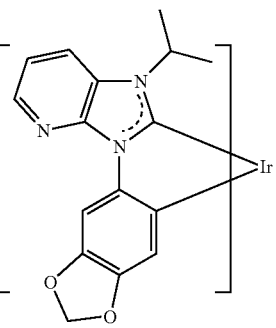
Compound 23
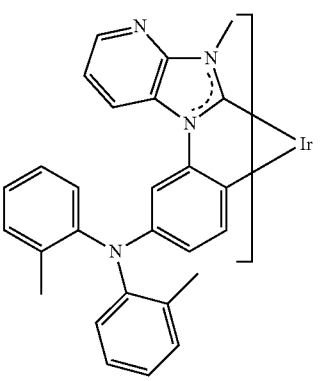
Compound 24
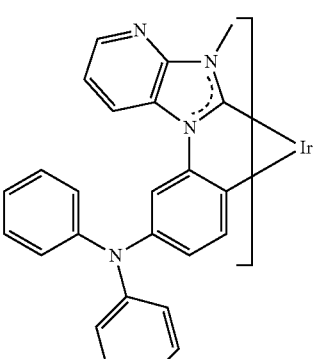
mer Compound 25

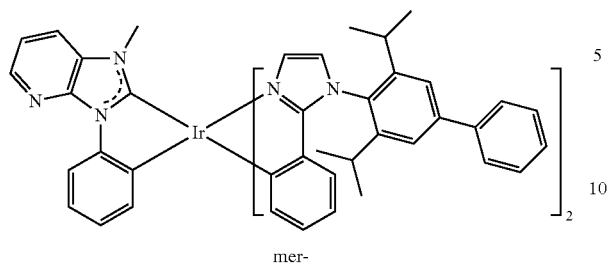

mer-

Compound 26

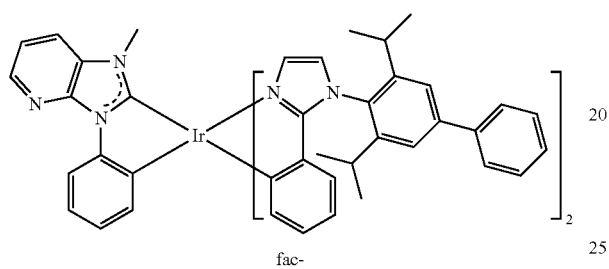

fac-

Compound 27

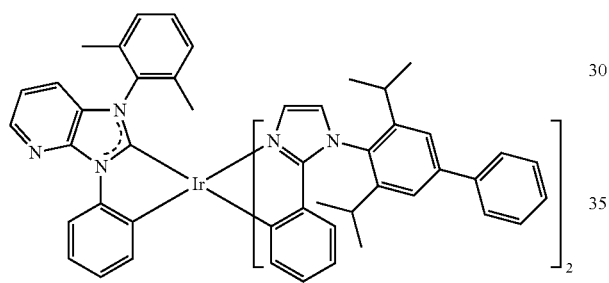

Compound 28

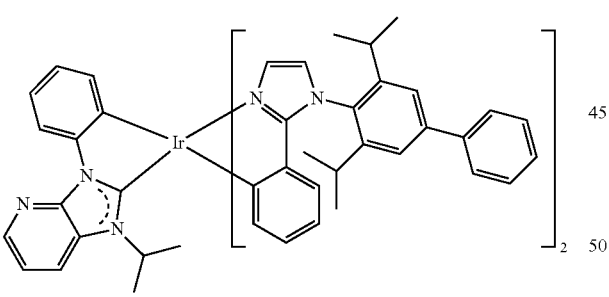

Compound 29

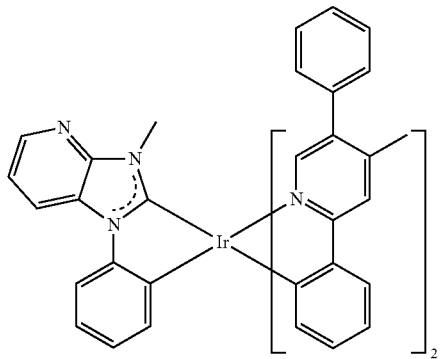

Compound 30

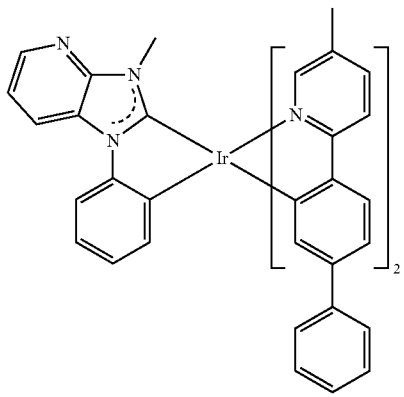

Compound 31

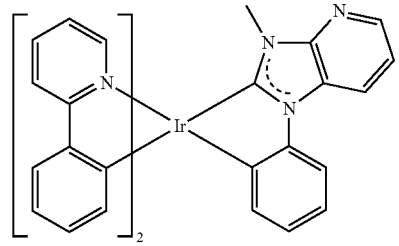

Compound 32

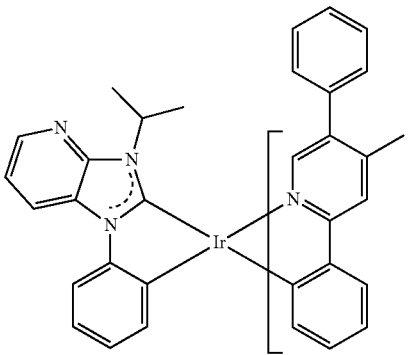

Additionally, a first device comprising an organic light emitting device is provided. The organic light emitting device further comprises an anode, a cathode and an organic layer, disposed between the anode and the cathode. The organic layer further comprises a compound comprising a ligand L having the formula:

Formula I

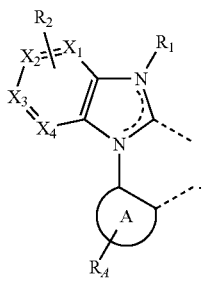

A is a 5-membered or 6-membered carbocyclic or heterocyclic ring. $R_2$ and $R_A$ may represent mono, di, tri or tetra substitutions. Each of $R_1$, $R_2$ and $R_A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphine, and combinations thereof. Two adjacent substituents of $R_2$ and $R_4$ are optionally joined to form a fused ring. Each of $X_1$, $X_2$, $X_3$ and $X_4$ are independently selected from the group consisting of C and N. At least two of $X_1$, $X_2$, $X_3$ and $X_4$ are N. The ligand L is coordinated to a metal M having an atomic number greater than 40. The bidentate ligand may be linked with other ligands to comprise a tridentate, tetradentate, pentadentate or hexadentate ligand.

In one aspect, the ligand L is selected from the group consisting of Formula II, Formula III, and Formula IV, as described above.

In one aspect, the compound is homoleptic. In another aspect, the compound is heteroleptic.

In another aspect, the compound has a formula selected from the group consisting of Formula V, Formula VI, and Formula VII, as described above.

In one aspect, L' is a monoanionic bidentate ligand. In another aspect, L' is selected from the group consisting of:

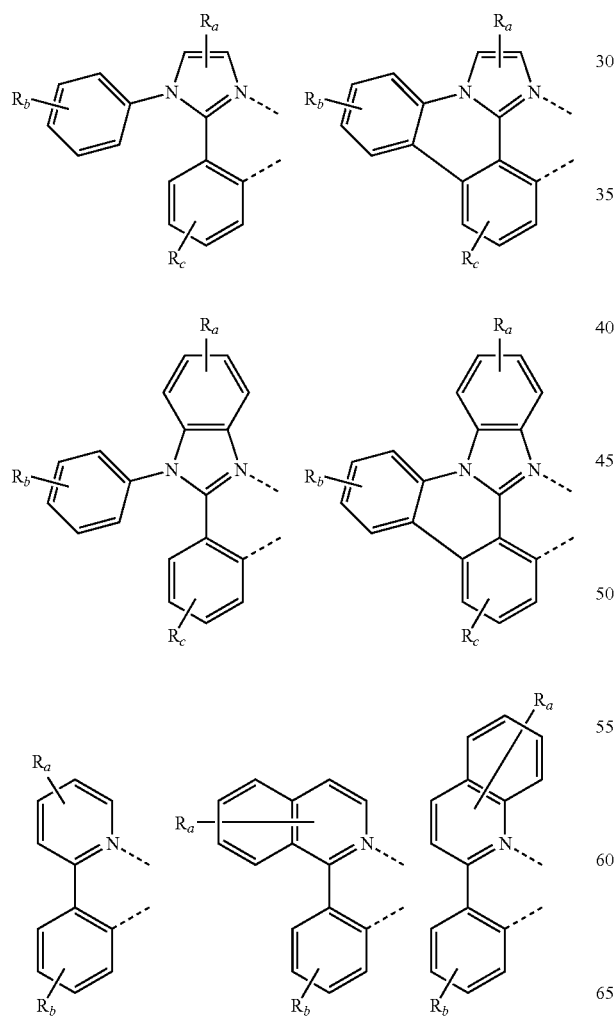

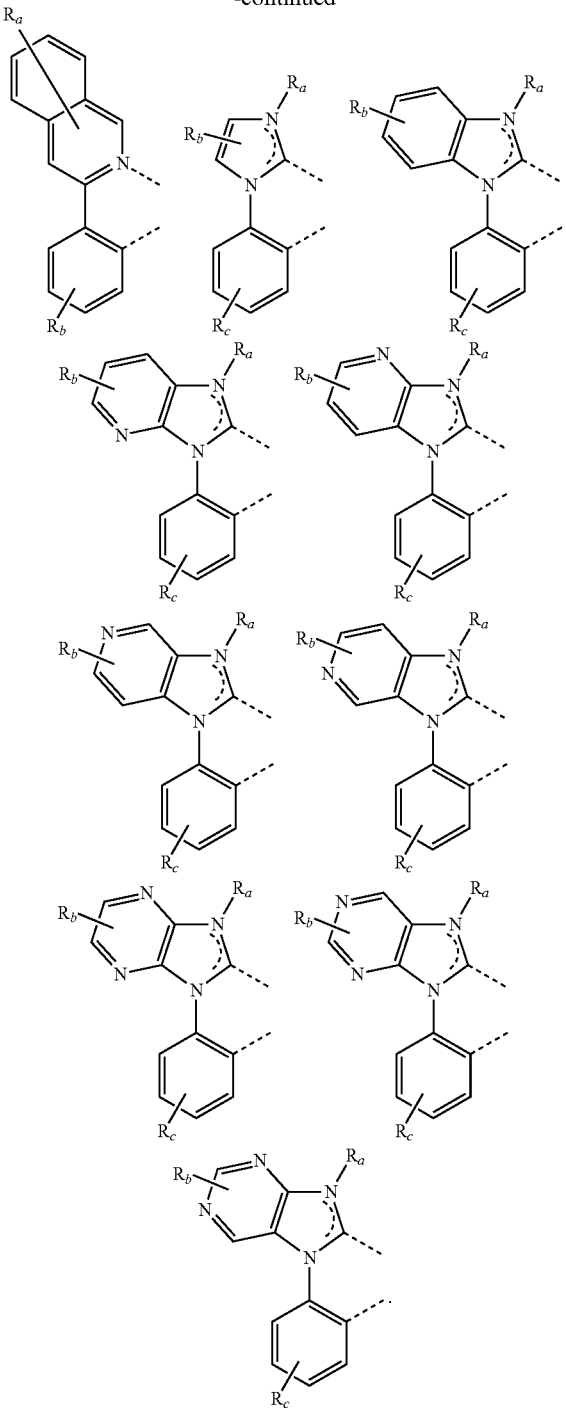

$R_a$, $R_b$, and $R_c$ may represent mono, di, tri or tetra substitutions. $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_a$, $R_b$, and $R_c$ are optionally joined to form a fused ring.

Specific, non-limiting examples of organometallic compounds comprising an imidazole carbene ligand with a diazine ring fused to the imidazole ring are provided. In one aspect, the compound is selected from the group consisting of Compound 1-Compound 7.

In one aspect, the organic layer is an emissive layer and the compound comprising the ligand L is an emissive dopant. In another aspect, the organic layer further comprises a host that comprises at least one of the chemical groups selected from the group consisting of

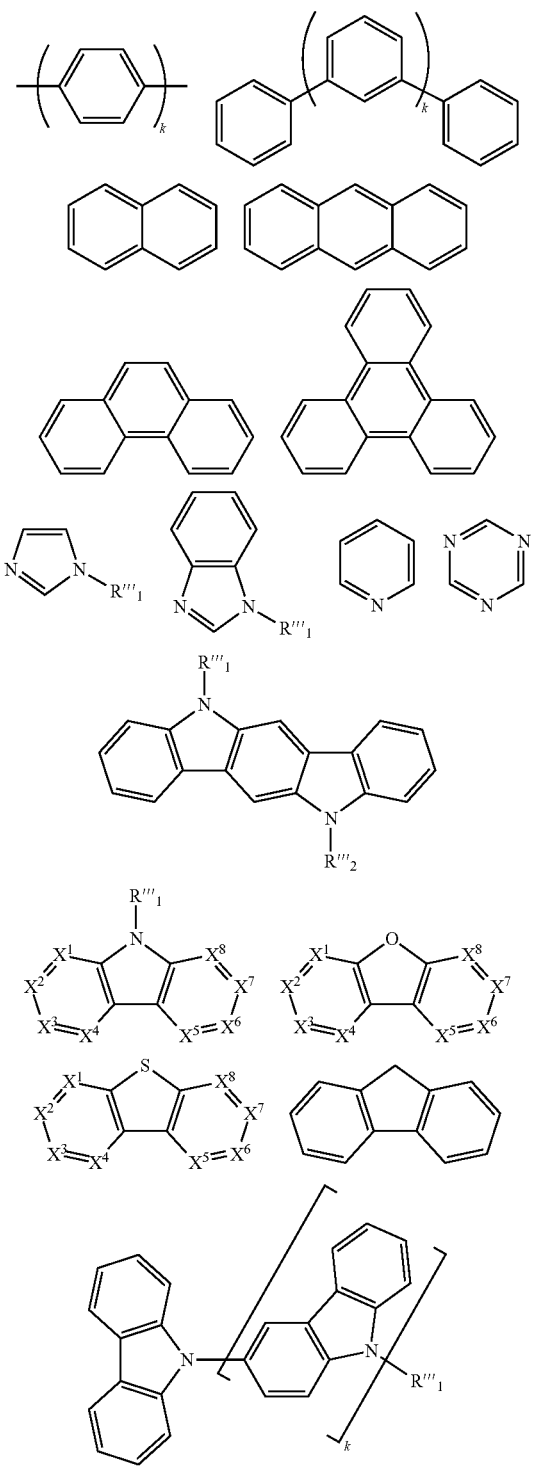

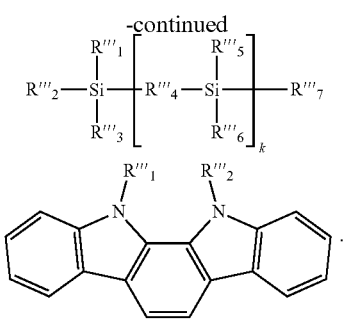

Each of $R'''_1$, $R'''_2$, $R'''_3$, $R'''_5$, $R'''_6$ and $R'''_7$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfonyl, sulfinyl, sulfonyl, phosphino, and combinations thereof. k is an integer from 0 to 20. Each of $X^1$, $X^2$, $X^3$, $X^4$, $X^5$, $X^6$, $X^7$ and $X^8$ are independently selected from the group consisting of CH and N.

In one aspect, the first device is an organic light emitting device. In another aspect, the first device is a consumer product.

Another first device comprising an organic light emitting device is also provided. The organic light emitting device further comprises an anode, a cathode and an organic layer, disposed between the anode and the cathode. The organic layer further comprises a compound selected from the group consisting of Compound 8-Compound 32.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in some embodiments of the present invention is not particularly limited, and any compound may be used as long as the compound is typically used as a hole injecting/transporting material. Examples of the material may include, but are not limited to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL may include, but are not limited to, the following general structures:

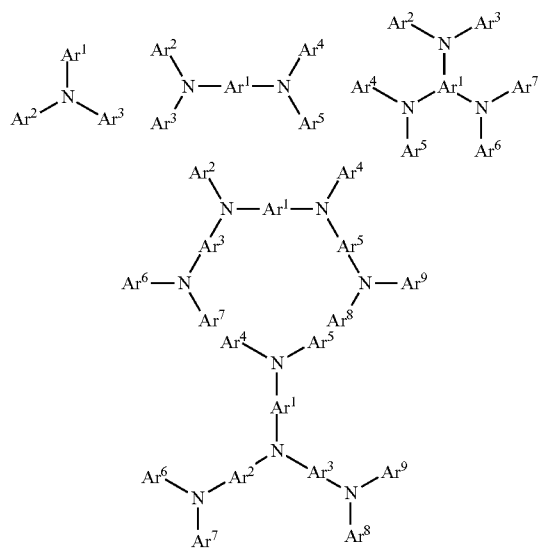

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof.

In one aspect, $Ar^1$ to $Ar^9$ is independently selected from the group consisting of:

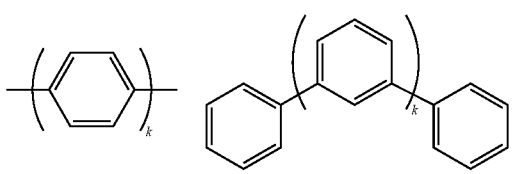

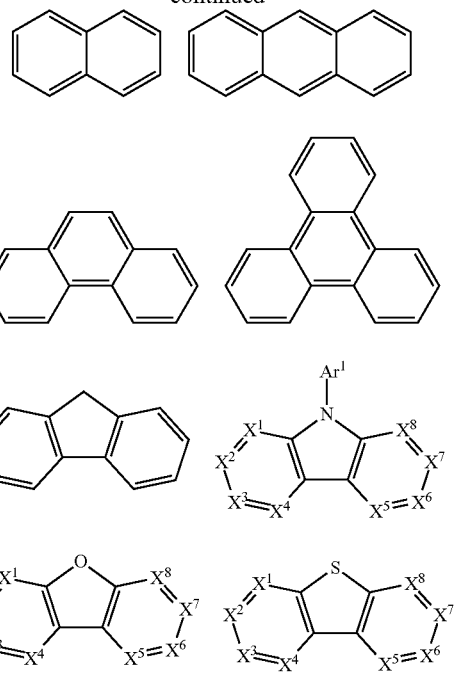

k is an integer from 1 to 20; $X^1$ to $X^8$ is CH or N; $Ar^1$ has the same group defined above.

Examples of metal complexes that may used in HIL or HTL include, but are not limited to, the following general formula:

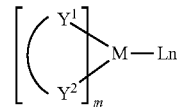

M is a metal having an atomic weight greater than 40; $(Y^1\text{-}Y^2)$ is a bidentate ligand, $Y^1$ and $Y^2$ are independently selected from C, N, O, P, and S; L is a different ligand; m is an integer value from 1 to the maximum number of ligands that may be attached to the metal; and m+n is the maximum number of ligands that may be attached to the metal.

In one aspect, $(Y^1\text{-}Y^2)$ is a 2-phenylpyridine derivative.

In another aspect, $(Y^1\text{-}Y^2)$ is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device in some embodiments of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host materials are preferred to have the following general formula:

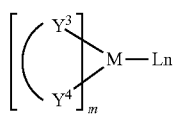

M is a metal; (Y³—Y⁴) is a bidentate ligand, $Y^3$ and $Y^4$ are independently selected from C, N, O, P, and S; L is a different ligand; m is an integer value from 1 to the maximum number of ligands that may be attached to the metal; and m+n is the maximum number of ligands that may be attached to the metal.

In one aspect, the metal complexes are:

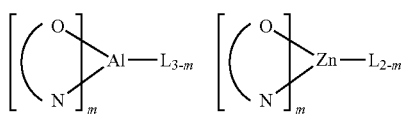

(O—N) is a bidentate ligand, having metal coordinated to atoms O and N.

In another aspect, M is selected from Ir and Pt.
In a further aspect, (Y³—Y⁴) is a carbene ligand.

Examples of organic compounds used as host materials include materials selected from the group consisting of: aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

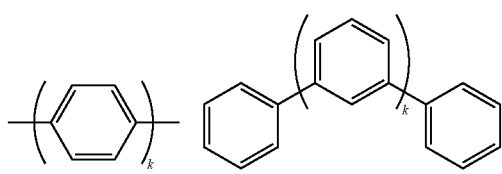

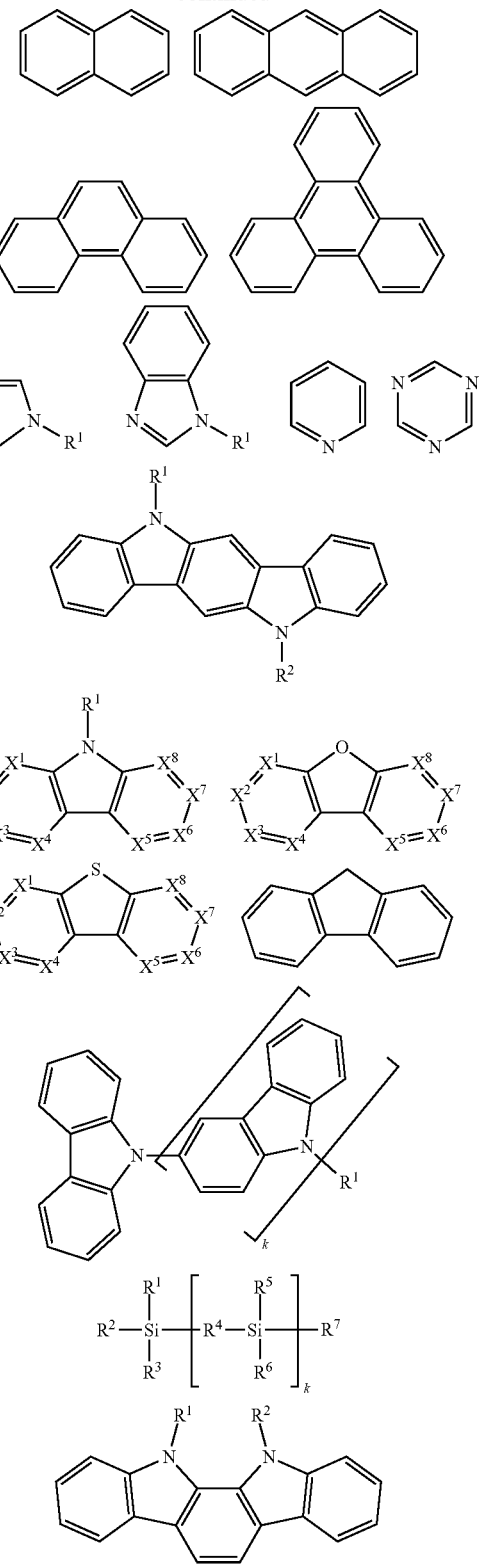

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. When it is aryl or heteroaryl, it has the similar definition as Ar's mentioned above.

k is an integer from 0 to 20.

$X^1$ to $X^8$ is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, the compound used in the HBL contains the same molecule used as host described above.

In another aspect, the compound used in the HBL contains at least one of the following groups in the molecule:

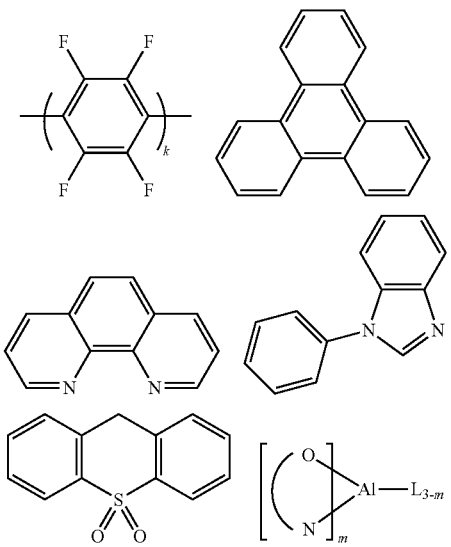

k is an integer from 0 to 20; L is a different ligand, m is an integer from 1 to 3.

ETL:

The electron transport layer (ETL) may include a material capable of transporting electrons. The electron transport layer may be intrinsic (undoped) or doped. Doping may be used to enhance conductivity. Examples of the ETL material are not particularly limited, and any metal complexes or organic compounds may be used as long as they are typically used to transport electrons.

In one aspect, the compound used in the ETL contains at least one of the following groups in the molecule:

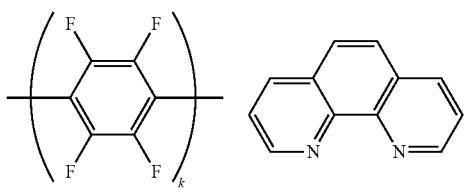

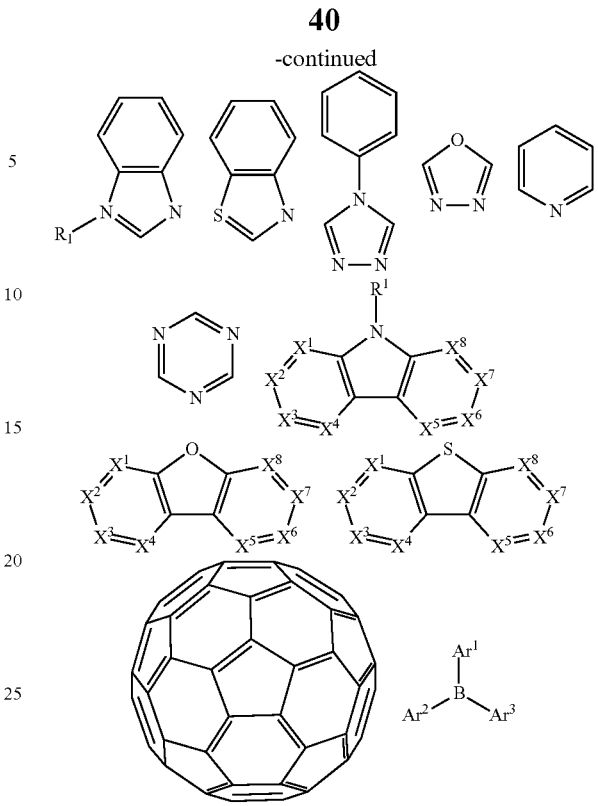

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. When it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from CH or N.

In another aspect, the metal complexes used in the ETL may contain, but are not limit to, the following general formula:

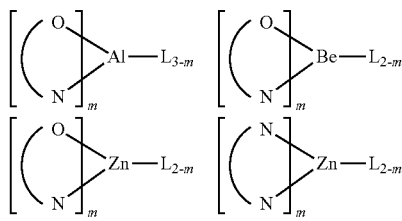

(O—N) or (N—N) is a bidentate ligand, having metal coordinated to atoms O, N or N, N; L is a different ligand; m is an integer value from 1 to the maximum number of ligands that may be attached to the metal.

In any above-mentioned compounds used in each layer of OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 2 below. Table 2 lists non-limiting classes of materials, non-limiting examples of compounds for each class, and references that disclose the materials.

TABLE 2

| MATERIAL | EXAMPLES OF MATERIAL | PUBLICATIONS |
|---|---|---|
| Hole injection materials | | |
| Phthalocyanine and porphryin compounds | 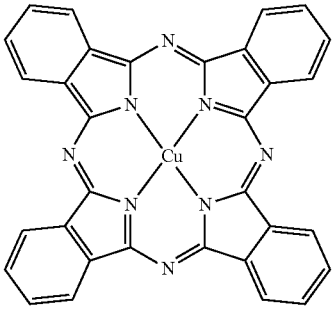 | Appl. Phys. Lett. 69, 2160 (1996) |
| Starburst triarylamines | 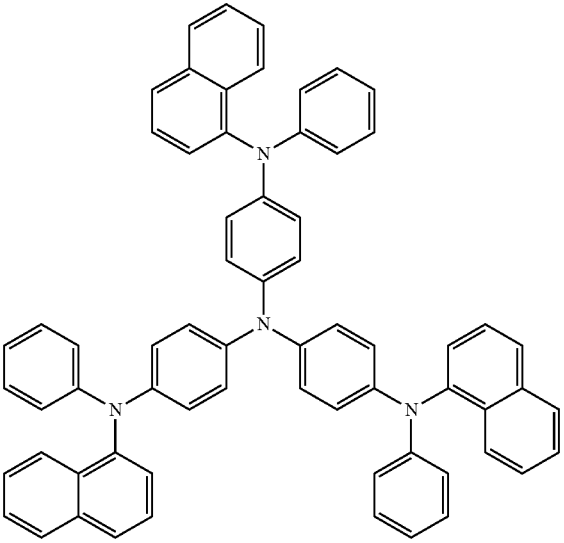 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | 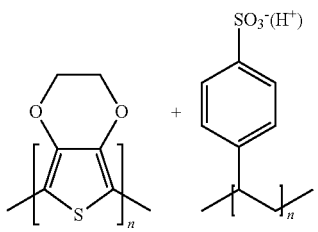 | Synth. Met. 87, 171 (1997) WO2007002683 |
| Phosphonic acid and silane SAMs | 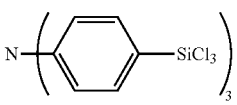 | US20030162053 |

TABLE 2-continued

| MATERIAL | EXAMPLES OF MATERIAL | PUBLICATIONS |
|---|---|---|
| Triarylamine or polythiophene polymers with conductivity dopants | [chemical structures] and [chemical structure] and [chemical structure] | EA01725079A1 |
| Arylamines complexed with metal oxides such as molybdenum and tungsten oxides | [chemical structure] + $MoO_x$ | SID Symposium Digest, 37, 923 (2006) WO2009018009 |

TABLE 2-continued
| MATERIAL | EXAMPLES OF MATERIAL | PUBLICATIONS |
| --- | --- | --- |
| Semiconducting organic complexes | 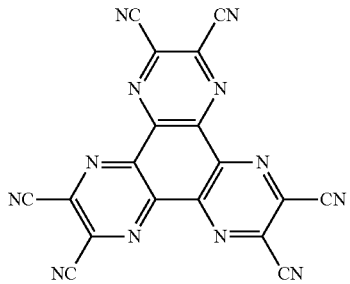 [SMILES: N#Cc1nc2c3nc(C#N)c(C#N)nc3c3nc(C#N)c(C#N)nc3c2nc1C#N] | US20020158242 |
| Metal organometallic complexes | 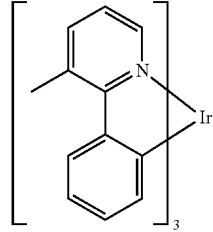 | US20060240279 |
| Cross-linkable compounds | 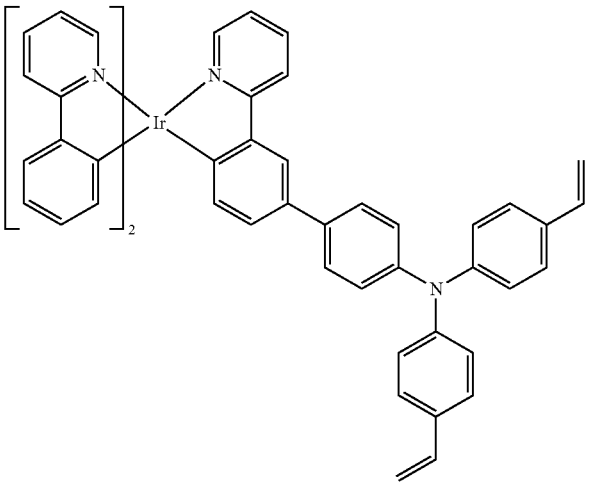 | US20080220265 |
| Hole transporting materials | | |
| Triarylamines (e.g., TPD, α-NPD) | 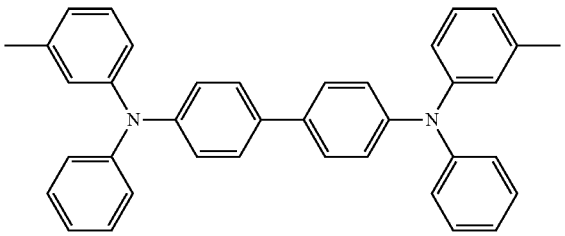 | Appl. Phys. Lett. 51, 913 (1987) |
| | 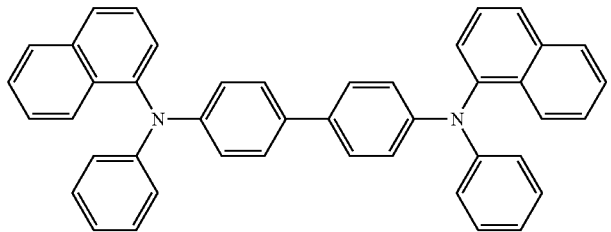 [SMILES: c1ccc(N(c2ccc(-c3ccc(N(c4ccccc4)c4cccc5ccccc45)cc3)cc2)c2cccc3ccccc23)cc1] | US5061569 |

TABLE 2-continued
| MATERIAL | EXAMPLES OF MATERIAL | PUBLICATIONS |
|---|---|---|
| | 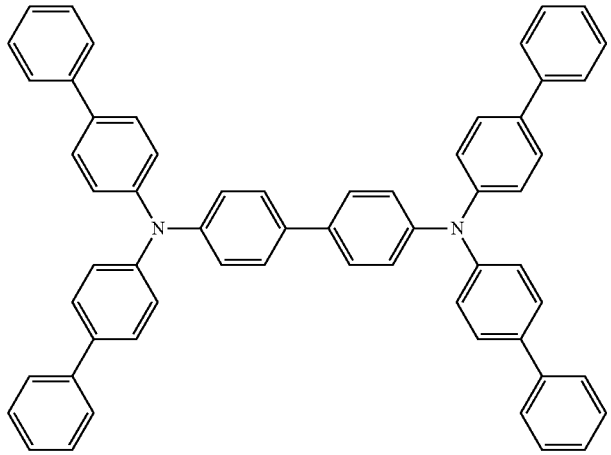 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 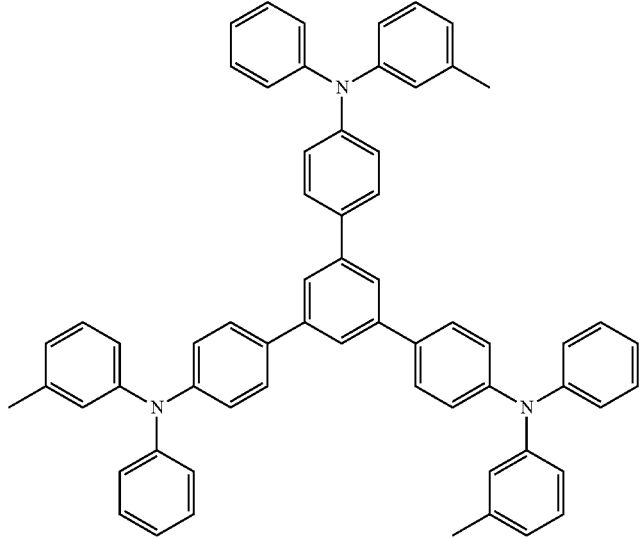 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 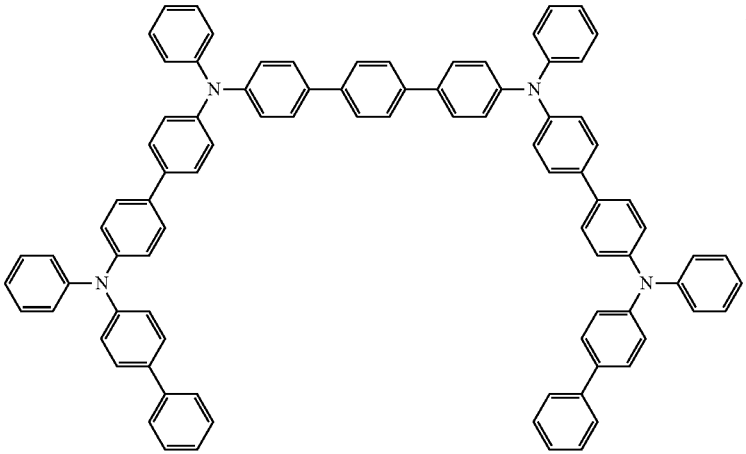 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 2-continued

| MATERIAL | EXAMPLES OF MATERIAL | PUBLICATIONS |
|---|---|---|
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US2008 0124572 |
| Triarylamine with (di)benzothiophene/(di) benzofuran | | US20070278938, US20080106190 |

TABLE 2-continued

| MATERIAL | EXAMPLES OF MATERIAL | PUBLICATIONS |
| --- | --- | --- |
| Indolocarbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |

TABLE 2-continued
| MATERIAL | EXAMPLES OF MATERIAL | PUBLICATIONS |
|---|---|---|
| Metal 8-hydroxyquinolates (e.g., Alq3, BAlq) | 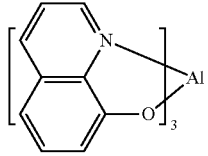 | Nature 395, 151 (1998) |
| | 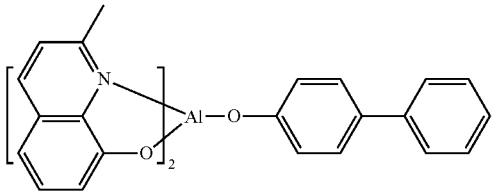 | US20060202194 |
| | 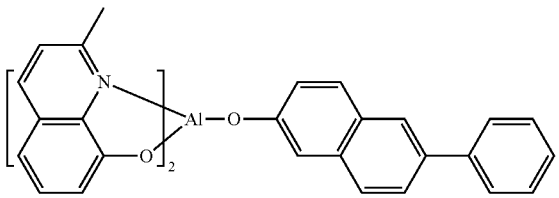 | WO2005014551 |
| | 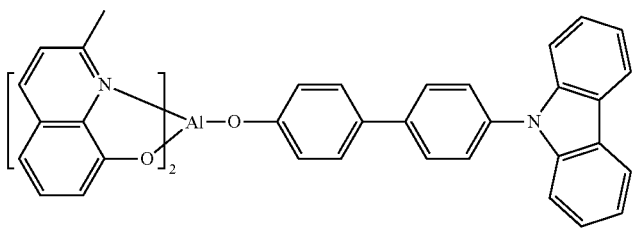 | WO2006072002 |
| Metal phenoxybenzothiazole compounds | 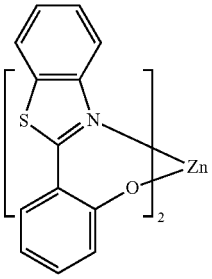 | Appl. Phys. Lett. 90, 123509 (2007) |
| Conjugated oligomers and polymers (e.g., polyfluorene) | 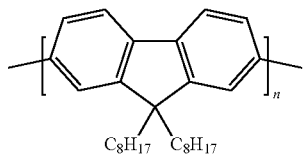 | Org. Electron. 1, 15 (2000) |
| Aromatic fused rings | 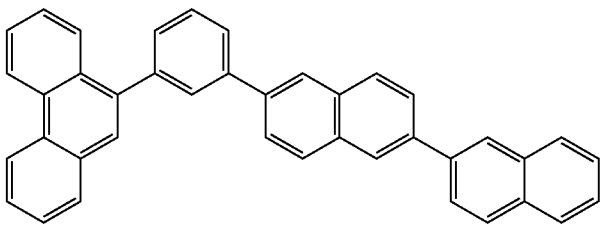 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |

TABLE 2-continued

| MATERIAL | EXAMPLES OF MATERIAL | PUBLICATIONS |
|---|---|---|
| Zinc complexes | | WO2009062578 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 2-continued

| MATERIAL | EXAMPLES OF MATERIAL | PUBLICATIONS |
| --- | --- | --- |
| | | US20060280965 |
| | | WO2009021126 |
| Donor acceptor type molecules | | WO2008056746 |
| Aza-carbazole/DBT/DBF | | JP2008074939 |
| Polymers (e.g., PVK) | | Appl. Phys. Lett. 77, 2280 (2000) |

TABLE 2-continued

| MATERIAL | EXAMPLES OF MATERIAL | PUBLICATIONS |
|---|---|---|
| Spirofluorene compounds | | WO2004093207 |
| Metal phenoxybenzooxazole compounds | | WO2005089025 |
| | | WO2006132173 |
| | | JP200511610 |
| Spirofluorene-carbazole compounds | | JP2007254297 |

TABLE 2-continued

| MATERIAL | EXAMPLES OF MATERIAL | PUBLICATIONS |
|---|---|---|
| | | JP2007254297 |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |

| MATERIAL | EXAMPLES OF MATERIAL | PUBLICATIONS |
|---|---|---|
| Tetraphenylene complexes | 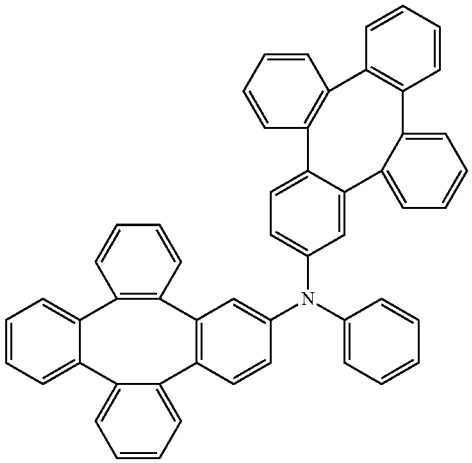 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 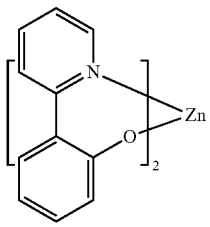 | WO2005030900 |
| Metal coordination complexes (e.g., Zn, Al, with N^N ligands) | 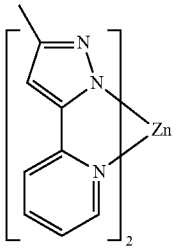 | US20040137268, US20040137267 |
| Blue hosts | | |
| Arylcarbazoles | 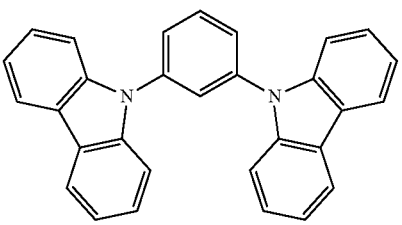 [SMILES: c1cc(-n2c3ccccc3c3ccccc32)cc(-n2c3ccccc3c3ccccc32)c1] | Appl. Phys. Lett, 82, 2422 (2003) |
| | 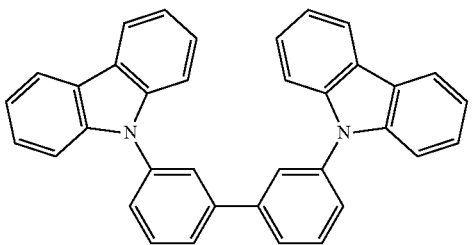 [SMILES: c1cc(-c2cccc(-n3c4ccccc4c4ccccc43)c2)cc(-n2c3ccccc3c3ccccc32)c1] | US20070190359 |

TABLE 2-continued
| MATERIAL | EXAMPLES OF MATERIAL | PUBLICATIONS |
|---|---|---|
| Dibenzothiophene/Dibenzofuran-carbazole compounds | 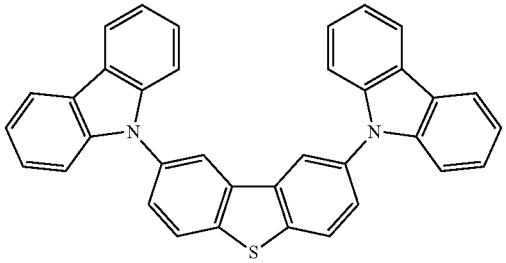 [SMILES: c1ccc2c(c1)c1ccccc1n2-c1ccc2sc3ccc(-n4c5ccccc5c5ccccc54)cc3c2c1] | WO2006114966, US20090167162 |
| | 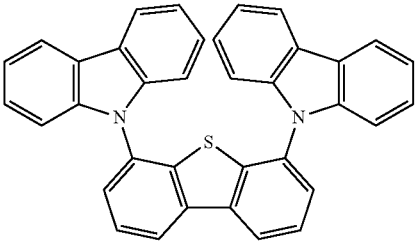 [SMILES: c1cc(-n2c3ccccc3c3ccccc32)c2sc3c(-n4c5ccccc5c5ccccc54)cccc3c2c1] | US20090167162 |
| | 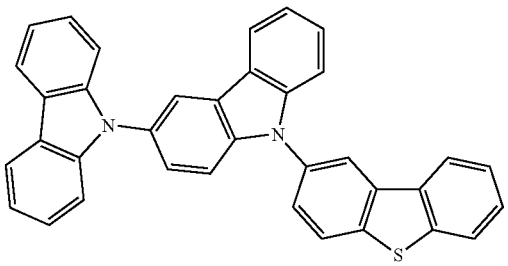 [SMILES: c1ccc2c(c1)sc1ccc(-n3c4ccccc4c4cc(-n5c6ccccc6c6ccccc65)ccc43)cc12] | WO2009086028 |
| | 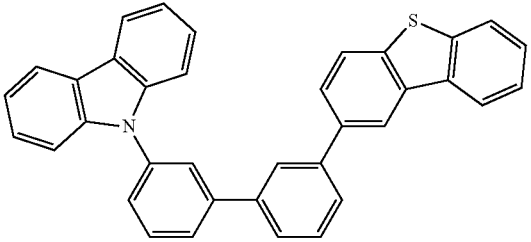 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 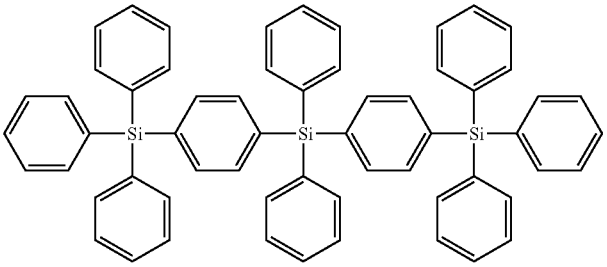 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 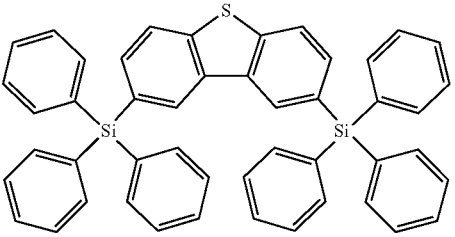 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 2-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| High triplet metal organometallic complex | | US7154114 |

Phosphorescent dopants
Red dopants

| | | |
| --- | --- | --- |
| Heavy metal porphyrins (e.g., PtOEP) | | Nature 395, 151 (1998) |
| Iridium(III) organometallic complexes | | Appl. Phys. Lett. 78, 1622 (2001) |

TABLE 2-continued
| MATERIAL | EXAMPLES OF MATERIAL | PUBLICATIONS |
|---|---|---|
| | 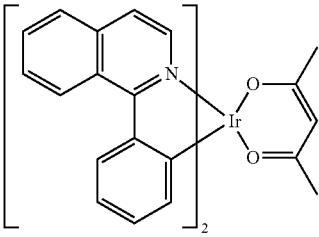 | US2006835469 |
| | 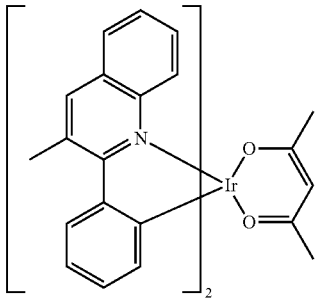 | US2006835469 |
| | 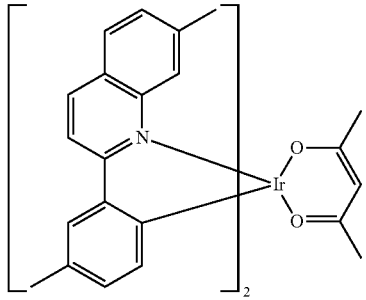 | US20060202194 |
| | 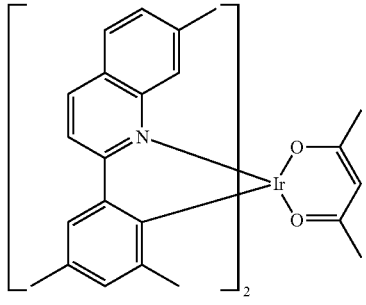 | US20060202194 |
| | 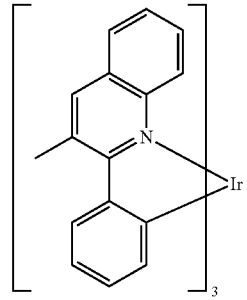 | US20070087321 |

TABLE 2-continued

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| Platinum(II) organometallic complexes | | WO2003040257 |

TABLE 2-continued

| MATERIAL | EXAMPLES OF MATERIAL | PUBLICATIONS |
| --- | --- | --- |
| Osminum(III) complexes | [structure with $F_3C$, pyrazole, pyridine, $Os(PPhMe_2)_2$] | Chem. Mater. 17, 3532 (2005) |
| Ruthenium(II) complexes | [structure with $^tBu$, pyrazole, isoquinoline, $Ru(PPhMe_2)_2$] | Adv. Mater. 17, 1059 (2005) |
| Rhenium (I), (II), and (III) complexes | [structure with quinolinolate, $Re-(CO)_4$] | US2005244673 |

Green dopants

| | | |
| --- | --- | --- |
| Iridium(III) organometallic complexes | [Ir(ppy)₃ structure] and its derivatives | Inorg. Chem. 40, 1704 (2001) |
| | [Ir(ppy)₂(acac) structure] | US20020034656 |

TABLE 2-continued
| MATERIAL | EXAMPLES OF MATERIAL | PUBLICATIONS |
|---|---|---|
| | 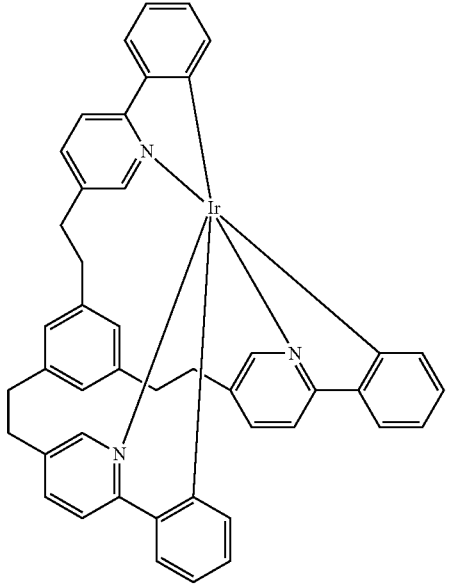 | US7332232 |
| | 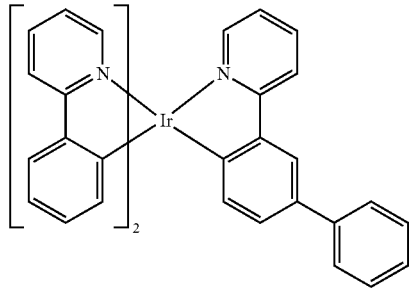 | US20090108737 |
| | 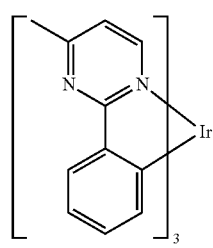 | US20090039776 |
| | 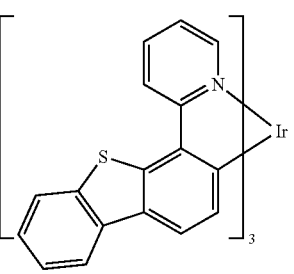 | US6921915 |

TABLE 2-continued
| MATERIAL | EXAMPLES OF MATERIAL | PUBLICATIONS |
|---|---|---|
| | 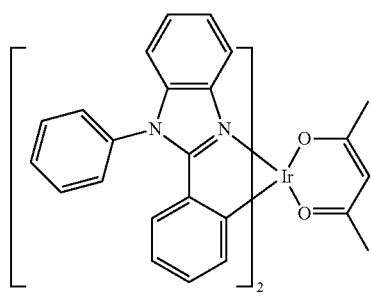 | US6687266 |
| | 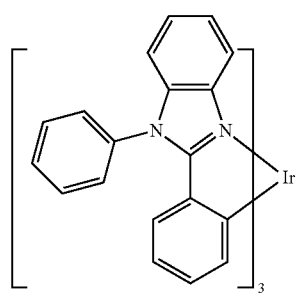 | Chem. Mater. 16, 2480 (2004) |
| | 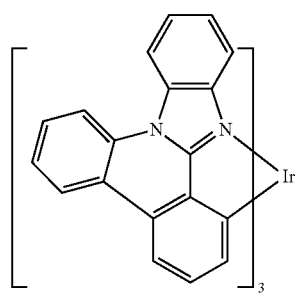 | US20070190359 |
| | 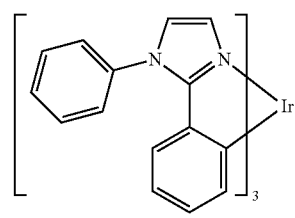 | US 20060008670<br>JP2007123392 |
| | 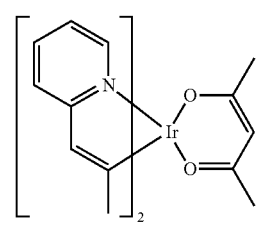 | Adv. Mater. 16, 2003 (2004) |

TABLE 2-continued
| MATERIAL | EXAMPLES OF MATERIAL | PUBLICATIONS |
|---|---|---|
| | 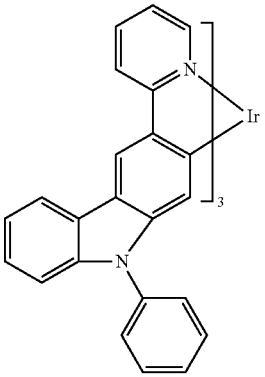 | Angew. Chem. Int. Ed. 2006, 45, 7800 |
| | 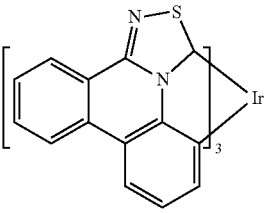 | WO2009050290 |
| | 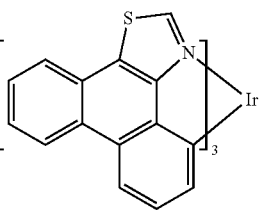 | US2009165846 |
| | 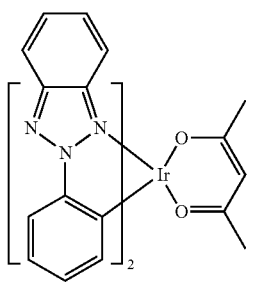 | US20080015355 |
| Monomer for polymeric metal organometallic compounds | 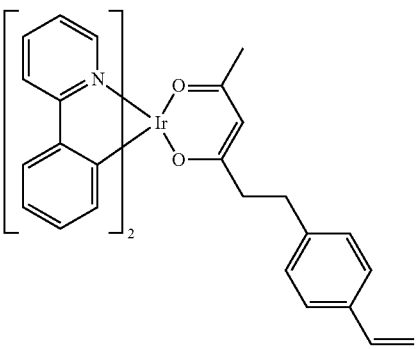 | US7250226, US7396598 |

TABLE 2-continued

| MATERIAL | EXAMPLES OF MATERIAL | PUBLICATIONS |
| --- | --- | --- |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |
| | | US20060263635 |

TABLE 2-continued

| MATERIAL | EXAMPLES OF MATERIAL | PUBLICATIONS |
|---|---|---|
| Cu complexes | | WO2009000673 |
| Gold complexes | | Chem. Commun. 2906 (2005) |
| Rhenium(III) complexes | | Inorg. Chem. 42, 1248 (2003) |
| Deuterated organometallic complexes | | US20030138657 |

TABLE 2-continued
| MATERIAL | EXAMPLES OF MATERIAL | PUBLICATIONS |
|---|---|---|
| Organometallic complexes with two or more metal centers | 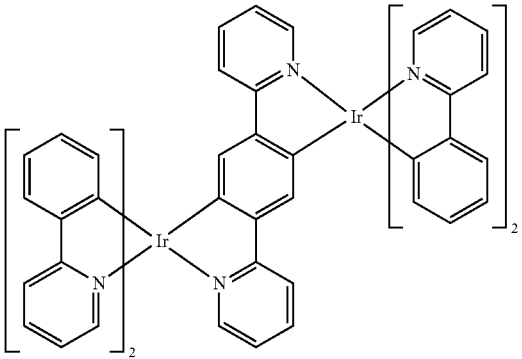 | US20030152802 |
| | 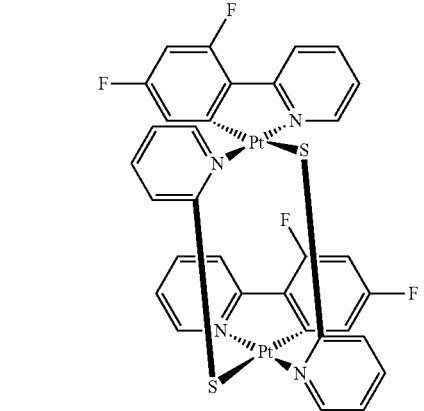 | US7090928 |
Blue dopants
| | | |
|---|---|---|
| Iridium(III) organometallic complexes | 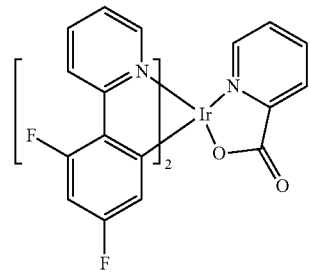 | WO2002002714 |
| | 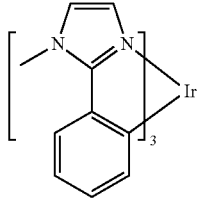 | WO2006009024 |
| | 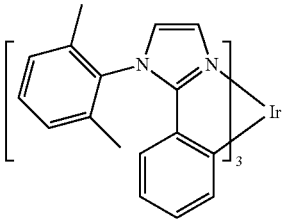 | US20060251923 |

TABLE 2-continued
| MATERIAL | EXAMPLES OF MATERIAL | PUBLICATIONS |
|---|---|---|
| | 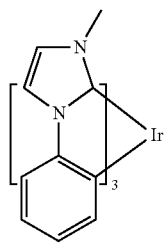 | US7393599, WO2006056418, US20050260441, WO2005019373 |
| | 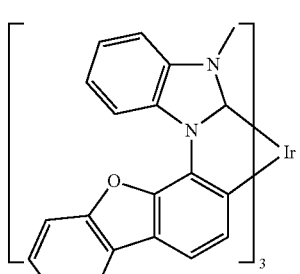 | US7534505 |
| | 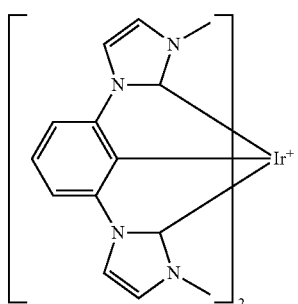 | US7445855 |
| | 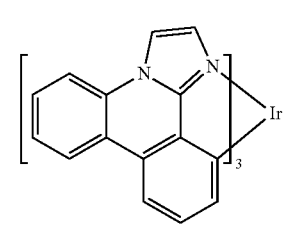 | US20070190359, US20080297033 |
| | 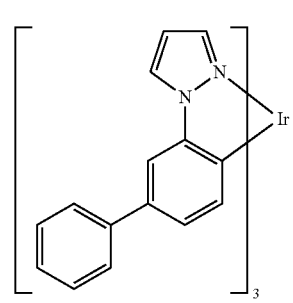 | US7338722 |
| | 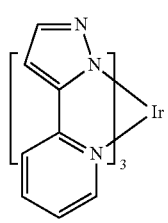 | US20020134984 |

TABLE 2-continued
| MATERIAL | EXAMPLES OF MATERIAL | PUBLICATIONS |
|---|---|---|
| | 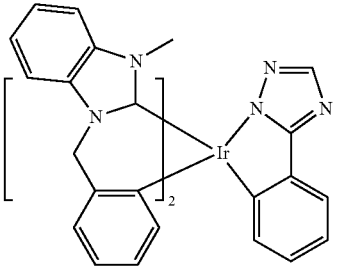 | Angew. Chem. Int. Ed. 47, 1 (2008) |
| | 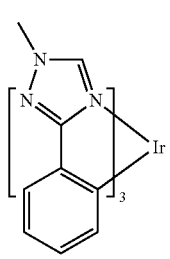 | Chem. Mater. 18, 5119 (2006) |
| | 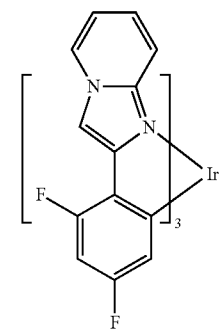 | Inorg. Chem. 46, 4308 (2007) |
| | 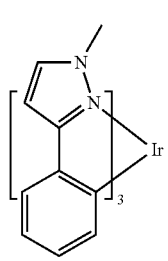 | WO2005123873 |
| | 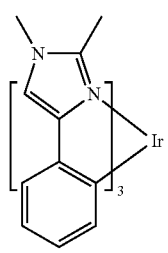 | WO2005123873 |
| | 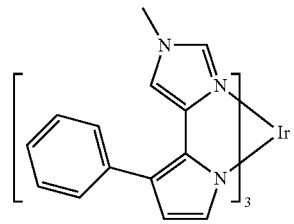 | WO2007004380 |

TABLE 2-continued

| MATERIAL | EXAMPLES OF MATERIAL | PUBLICATIONS |
|---|---|---|
|  |  | WO2006082742 |
| Osmium(II) complexes |  | US7279704 |
|  |  | Organometallics 23, 3745 (2004) |
| Gold complexes |  | Appl. Phys. Lett. 74, 1361 (1999) |
| Platinum(II) complexes |  | WO2006098120, WO2006103874 |

TABLE 2-continued

| MATERIAL | EXAMPLES OF MATERIAL | PUBLICATIONS |
|---|---|---|
| Exciton/hole blocking layer materials | | |
| Bathocuprine compounds (e.g., BCP, BPhen) | 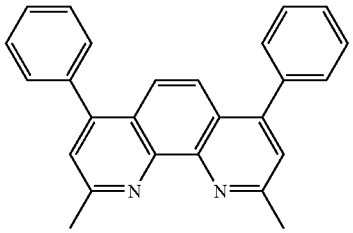 [SMILES: Cc1cc(-c2ccccc2)c2ccc3c(-c4ccccc4)cc(C)nc3c2n1] | Appl. Phys. Lett. 75, 4 (1999) |
| | 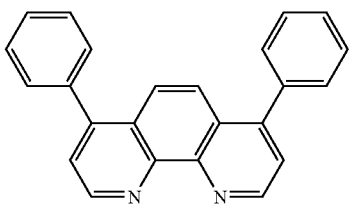 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 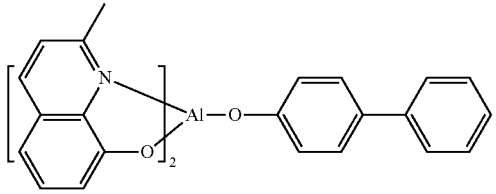 | Appl. Phys. Lett. 81, 162 (2002) |
| 5-member ring electron deficient heterocycles such as triazole, oxadiazole, imidazole, benzoimidazole | 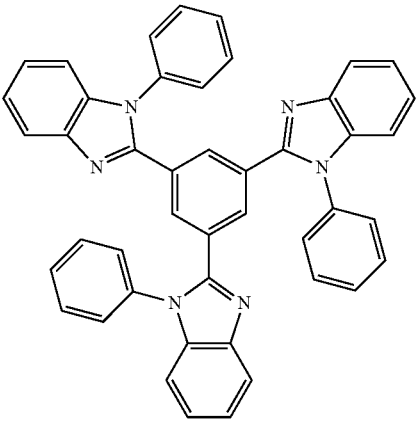 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 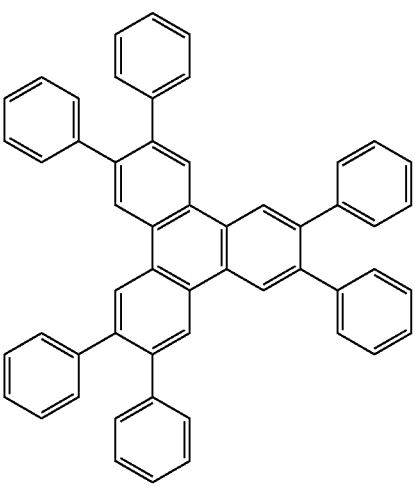 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 2-continued
| MATERIAL | EXAMPLES OF MATERIAL | PUBLICATIONS |
|---|---|---|
| Fluoinated aromatic compounds | 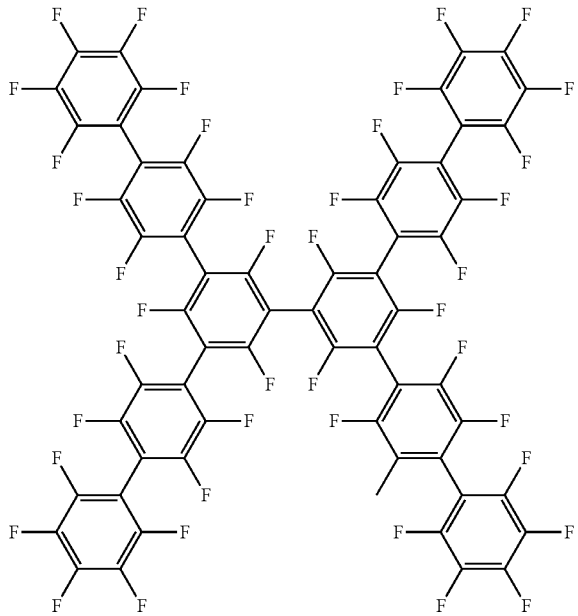 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 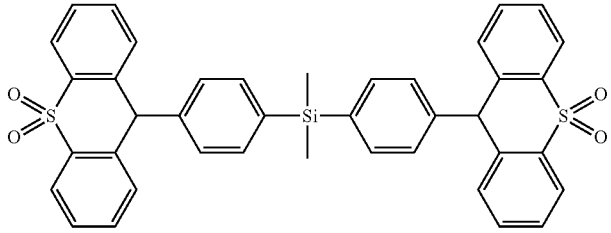 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
Electron transporting materials
| | | |
|---|---|---|
| Anthracene-benzoimidazole compounds | 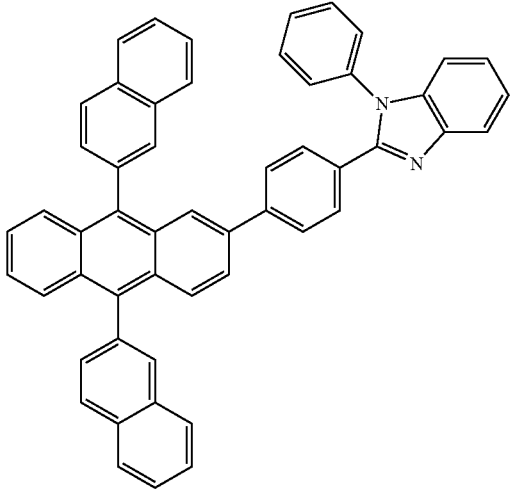 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |

TABLE 2-continued
| MATERIAL | EXAMPLES OF MATERIAL | PUBLICATIONS |
|---|---|---|
| | 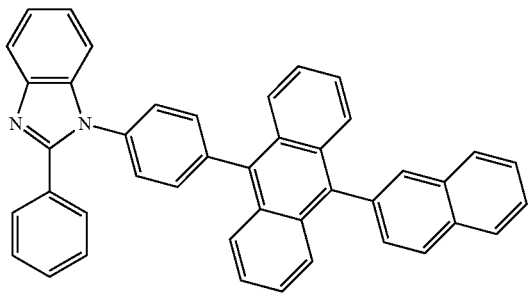 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 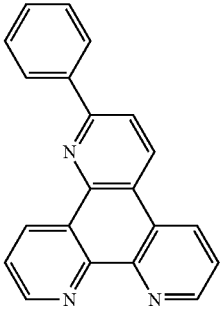 [SMILES: c1ccc(-c2ccc3c4cccnc4c4ncccc4c3n2)cc1] | US20090115316 |
| Anthracene-benzothiazole compounds | 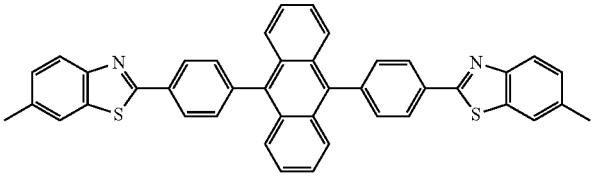 | Appl. Phys. Lett. 89, 063504 (2006) |
| Metal 8-hydroxyquinolates (e.g., Alq$_3$, Zrq$_4$) | 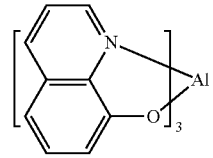 | Appl. Phys. Lett. 51, 913 (1987)<br>US7230107 |
| Metal hydroxybenoquinolates | 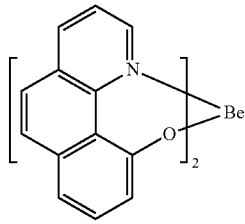 | Chem. Lett. 5, 905 (1993) |
| Bathocuprine compounds such as BCP, BPhen, etc | 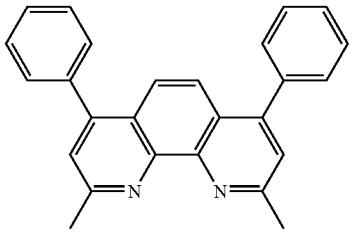 [SMILES: Cc1cc(-c2ccccc2)c2ccc3c(-c4ccccc4)cc(C)nc3c2n1] | Appl. Phys. Lett. 91, 263503 (2007) |

TABLE 2-continued
| MATERIAL | EXAMPLES OF MATERIAL | PUBLICATIONS |
|---|---|---|
| | 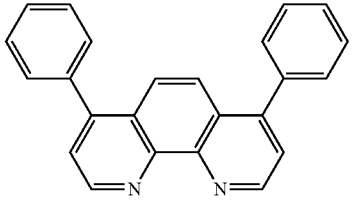 [SMILES: c1ccc(-c2ccnc3c2ccc2c(-c4ccccc4)ccnc23)cc1] | Appl. Phys. Lett. 79, 449 (2001) |
| 5-member ring electron defieicnt heterocycles (e.g., triazole, oxidiazole, imidazole, benzoimidazole) | 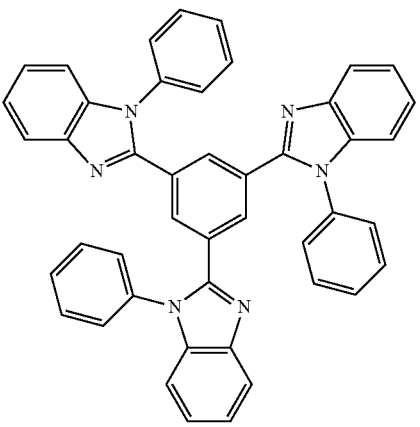 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 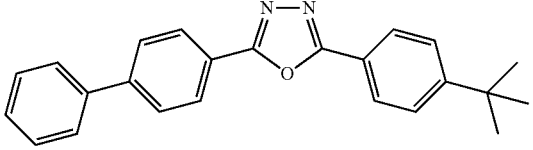 [SMILES: CC(C)(C)c1ccc(-c2nnc(-c3ccc(-c4ccccc4)cc3)o2)cc1] | Appl. Phys. Lett. 55, 1489 (1989) |
| | 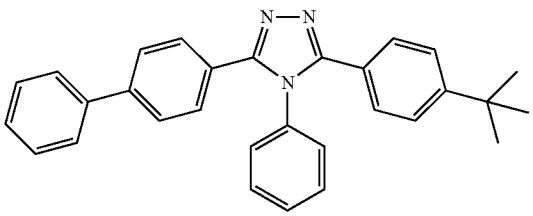 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 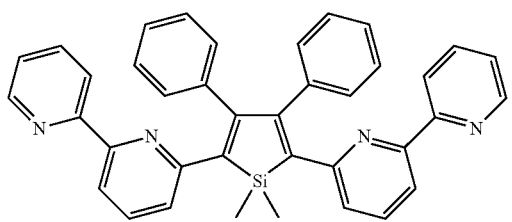 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |

TABLE 2-continued
| MATERIAL | EXAMPLES OF MATERIAL | PUBLICATIONS |
|---|---|---|
| Arylborane compounds | 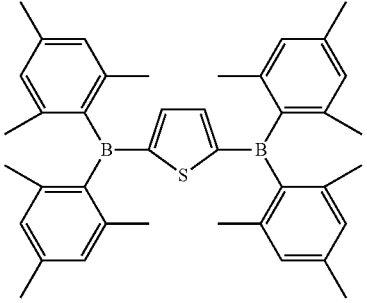 | J. Am. Chem. Soc. 120, 9714 (1998) |
| Fluorinated aromatic compounds | 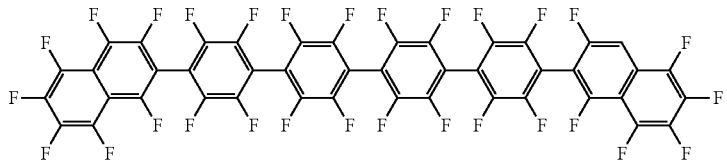 [SMILES: Fc1cc2c(F)c(F)c(F)c(F)c2c(F)c1-c1c(F)c(F)c(-c2c(F)c(F)c(-c3c(F)c(F)c(-c4c(F)c(F)c(-c5c(F)c(F)c6c(F)c(F)c(F)c(F)c6c5F)c(F)c4F)c(F)c3F)c(F)c2F)c(F)c1F] | J. Am. Chem. Soc. 122, 1832 (2000) |
| Fullerene (e.g., C60) | 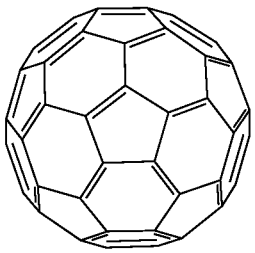 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 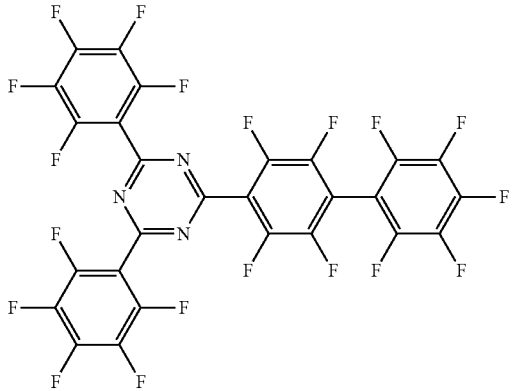 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 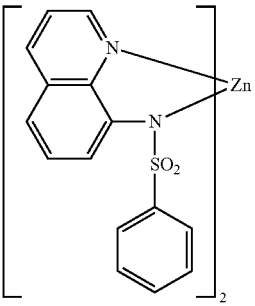 | US6528187 |

EXPERIMENTAL

Compound Examples

Example 1

Synthesis of Compound 1 and Compound 2

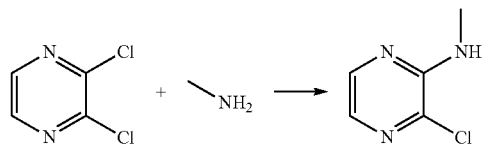

Synthesis of 3-chloro-N-methylpyrazin-2-amine 2,3-dichloropyrazine (15 g, 101 mmol), methanamine (9.48 g, 101 mmol), and 100 mL of THF were stirred at room temperature for 24 h. The solvent was evaporated. The residue was dissolved in dichloromethane and washed with NaOH solution. The organic layer was separated and dried over $MgSO_4$. After evaporating solvent, the residue was purified by column using dichloromethane as solvent to give 3-chloro-N-methylpyrazin-2-amine (6.3 g, 43.6% yield).

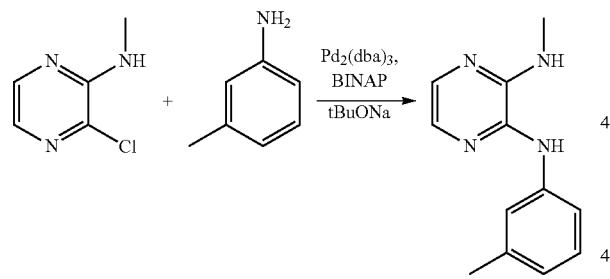

Synthesis of $N^2$-methyl-$N^3$-(m-tolyl)pyrazine-2,3-diamine 3-chloro-N-methylpyrazin-2-amine (6 g, 41.8 mmol), m-toluidine (6.72 g, 62.7 mmol), 2,2'-bis(diphenylphosphino)-1,1'-binaphthalene (0.520 g, 0.836 mmol), $Pd_2(dba)_3$ (0.383 g, 0.418 mmol), and sodium t-butoxide (6.02 g, 62.7 mmol) were mixed in 200 mL of toluene and degassed for 20 minutes. The mixture was heated to reflux overnight. TLC indicated the reaction did not go to completion. 0.3 g of $Pd_2(dba)_3$ and 0.56 g of BINAP was added and heated up to reflux again for 24 h. The reaction was filtered through Celite® and concentrated. The residue was purified by column using 10% ethyl acetate and dichloromethane as solvent to give $N^2$-methyl-$N^3$-(m-tolyl)pyrazine-2,3-diamine (2.7 g, 30.2%).

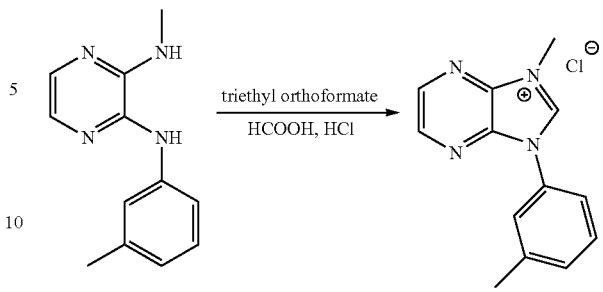

Synthesis of 3-m-tolyl-3H-imidazo[4,5-b]pyrazine methyl salt $N^2$-methyl-$N^3$-(m-tolyl)pyrazine-2,3-diamine (2.7 g, 12.6 mmol), concentrated HCl (1 mL), and 5 drops of formic acid were added in triethyl orthoformate (52 mL). The reaction was refluxed overnight. After cooled to room temperature, the white solid was collected by filtration. The solid was further purified by recrystallizing from ethanol to give 3-m-tolyl-3H-imidazo[4,5-b]pyrazine methyl salt (3 g, 80% yield).

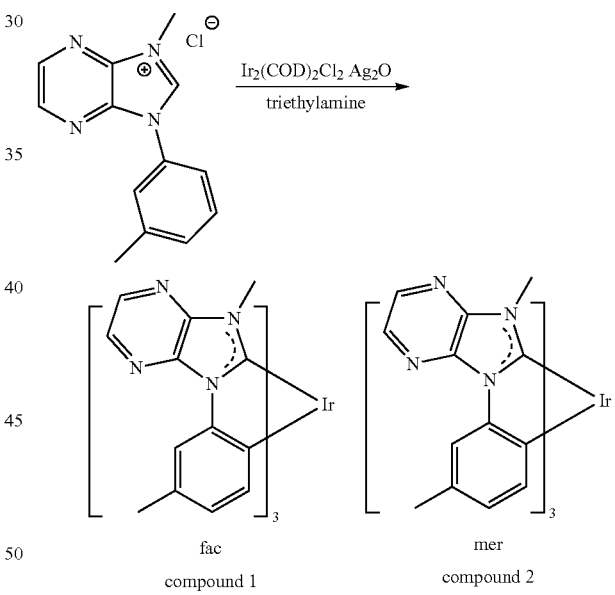

fac
compound 1 mer
compound 2

Synthesis of Compound 1 and Compound 2

Carbene ligand (2.9 g, 9.79 mmol), $Ir_2(COD)_2Cl_2$ (1.093 g, 1.632 mmol), silver oxide (2.269 g, 9.79 mmol), triethylamine (1.365 ml, 9.79 mmol), and chlorobenzene (200 mL) were mixed in a 500 mL flask and degassed for 30 minutes. The mixture was then heated up to reflux for 24 h. After the reaction cooled to room temperature, it was filtered through Celite®. The solvent was evaporated and purified by column using hexanes and ethyl aceate as solvent to give Compound 1 (0.9 g, 30% yield) and Compound 2 (0.3 g, 10% yield).

Example 2

Synthesis of Compound 3 and Compound 4

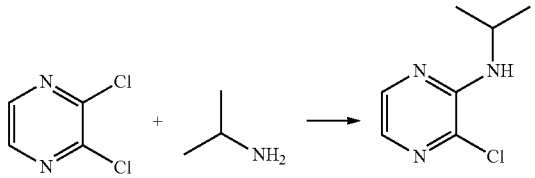

Synthesis of 3-chloro-N-isopropylpyrazin-2-amine 2,3-dichloropyrazine (10 g, 67.1 mmol), propan-2-amine (11.90 g, 201 mmol), and 50 mL of THF were mixed in a three-neck flask and stirred at room temperature overnight. The reaction was brought to reflux overnight. The reaction was cooled and the solvent was evaporated. The residue was dissolved in dichloromethane and the salt was filtered. The solvent was then evaporated and the residue was purified by column using dichloromethane as solvent to give 3-chloro-N-isopropylpyrazin-2-amine (6.2 g, 53.8%).

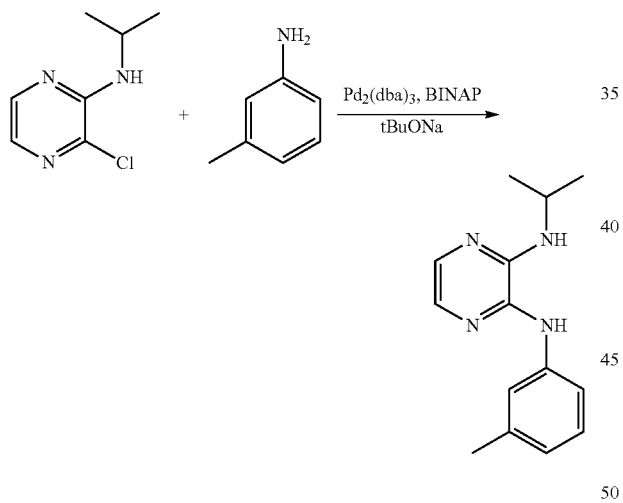

Synthesis of $N^2$-isopropyl-$N^3$-(m-tolyl)pyrazine-2,3-diamine 3-chloro-N-isopropylpyrazin-2-amine (6 g, 35.0 mmol), m-toluidine (5.62 g, 52.4 mmol), 2,2'-bis(diphenylphosphino)-1,1'-binaphthalene (0.435 g, 0.699 mmol), $Pd_2(dba)_3$ (0.320 g, 0.350 mmol), and sodium t-butoxide (5.04 g, 52.4 mmol) were mixed in 200 mL of toluene and degassed for 20 minutes. The mixture was heated to reflux for 5 h. The reaction was cooled to room temperature and water was added. The reaction mixture was extracted with dichloromethane and washed with water. The crude was columned with 10% ethyl acetate and dichloromethane to give $N^2$-isopropyl-$N^3$-(m-tolyl)pyrazine-2,3-diamine (7.4 g, 87%).

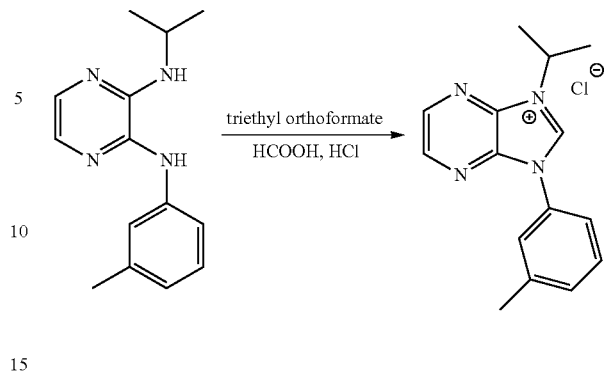

Synthesis of carbene precursor $N^2$-isopropyl-$N^3$-(m-tolyl)pyrazine-2,3-diamine (7.3 g, 30.5 mmol), concentrated HCl (2 mL), and 20 drops of formic acid were added in triethyl orthoformate (124 mL). The reaction was refluxed overnight. After it cooled to room temperature, the white solid was collected by filtration and washed with ethyl acetate to give desired product (7.3 g, 75% yield).

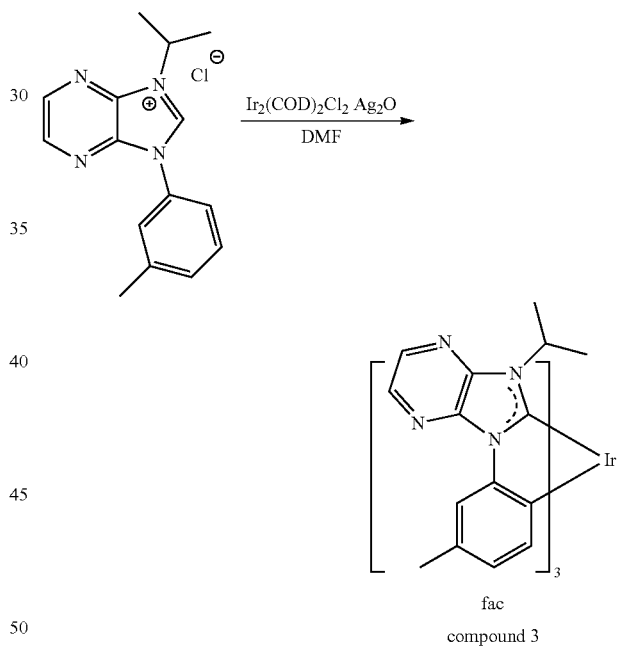

fac
compound 3

Synthesis of Compound 3

Carbene ligand (3.8 g, 11.72 mmol), $Ir_2(COD)_2Cl_2$ (1.308 g, 1.953 mmol), silver oxide (2.72 g, 11.72 mmol), and DMF (Volume: 200 ml) were mixed M a 500 mL flask and degassed for 30 minutes. The mixture was then heated up to reflux for 24 h. After it cooled to room temperature, the reaction mixture was filtered through Celite®. The solvent was then distilled under vacuum. The residue was dissolved in dichloromethane and washed with sodium hydroxide solution and dried over $MgSO_4$. The solvent was evaporated and residue was purified by column using dichloromethane and 3:1 dichloromethane and hexanes as solvent to give Compound 3 (1 g, 27%).

107

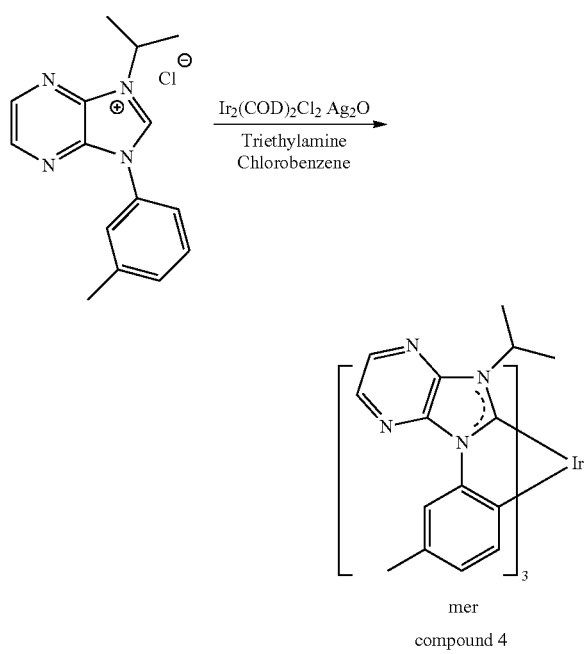

mer
compound 4

Synthesis of Compound 4

Carbene ligand (7 g, 21.59 mmol), Ir$_2$(COD)$_2$Cl$_2$ (2.065 g, 3.08 mmol), silver(I) oxide (5.00 g, 21.59 mmol), triethylamine (3.07 ml, 21.59 mmol) were mixed in 400 mL of chlorobenzene. The mixture was bubbled with nitrogen for 20 minutes. The reaction was then heated up to reflux for 24 h. After it cooled to room temperature, the mixture was filtered through Celite®. The solvent was evaporated. The residue was purified by column using dichloromethane to 5% ethyl acetate and dichloromethane to give compound 4 (1.8 g, 62% yield).

Example 3

Synthesis of Compound 5

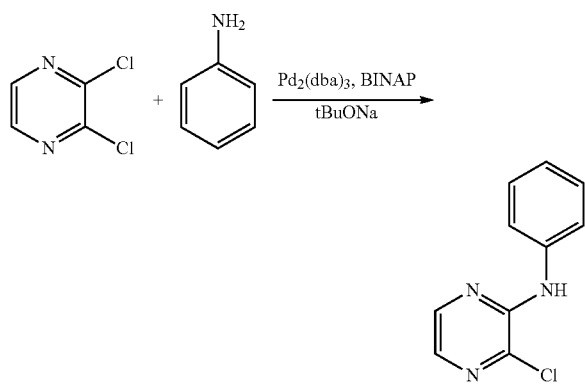

Synthesis of 3-chloro-N-phenylpyrazin-2-amine

Aniline (11.25 g, 121 mmol), dichloropyrazine (20 g, 134 mmol), sodium t-butoxide (15.48 g, 161 mmol) were stirred in toluene (300 mL) under nitrogen purging for 15 minutes.

108

Pd$_2$(dba)$_3$ (1.23 g, 1.34 mmol) and BINAP (3.34 g, 5.47 mmol) were added. The reaction was heated to 90° C. for 5 h. After it cooled to room temperature, the reaction was filtered through Celite®. After solvent evaporation, the residue was purified with column chromatography using 30% ethyl acetate in hexanes as solvent to give 3-chloro-N-phenylpyrazin-2-amine (4.5 g, 16.3% yield).

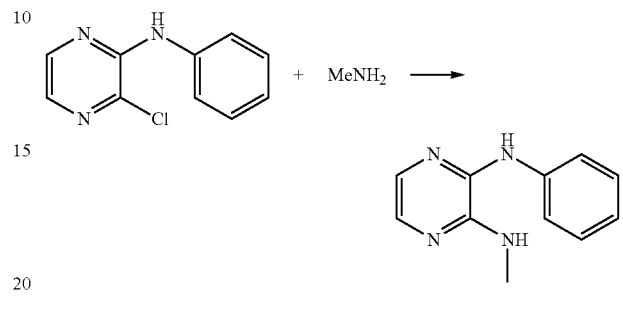

Synthesis of N$^2$-methyl-N$^3$-phenylpyrazine-2,3-diamine 3-chloro-N-phenylpyrazin-2-amine (4.5 g, 21.22 mmol) was stirred with methyl amine (20.59 g, 20.9 mmol, 33 wt % in THF) under reflux overnight. The solvent was evaporated and the residue was purified by column chromatography using 50% ethyl acetate and hexanes to give N$^2$-methyl-N$^3$-phenylpyrazine-2,3-diamine (2.4 g, 54.8%).

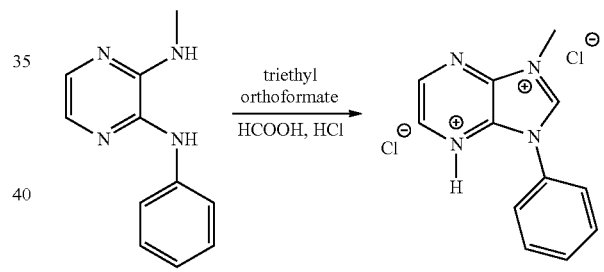

Synthesis of 3-phenyl-3H-imidazo[4,5-b]pyrazine methyl salt

N$^2$-methyl-N$^3$-phenylpyrazine-2,3-diamine (2.5 g, 12.5 mmol), concentrated HCl (1 mL), and 5 drops of formic acid were added in triethyl orthoformate (52 mL). The reaction was refluxed overnight. After it cooled to room temperature, the white solid was collected by filtration. The solid was further purified by recrystallizing from ethanol to give 3-phenyl-3H-imidazo[4,5-b]pyrazine methyl salt (1.2 g, 34% yield).

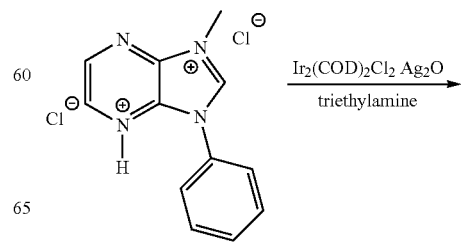

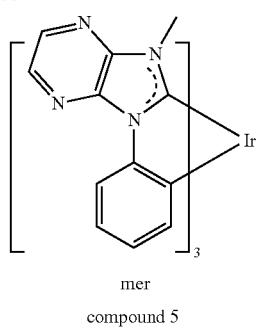

mer
compound 5

Synthesis of Compound 5

The carbene precursor (1.2 g, 4.25 mmol), silver oxide (0.99 g, 4.25 mmol), triethylamine (0.43 g, 4.25 mmol), Ir$_2$(COD)$_2$Cl$_2$ (0.475 g, 0.7 mmol) and chlorobenzene (50 mL) were added to the reaction flask and heated to reflux overnight. After it cooled to room temperature, the reaction mixture was filtered through Celite®. The solution was concentrated and purified by column using 5-20% of ethyl acetate and dichloromethane as solvent to give compound 5 (0.37 g, 32% yield).

Example 4

Synthesis of Compound 8 and Compound 9

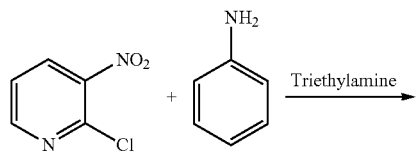

Synthesis of 3-nitro-N-phenylpyridin-2-amine 2-chloro-3-nitropyridine (25 g, 158 mmol), aniline (17.62 g, 189 mmol), and triethylamine (19.15 g, 189 mmol) were mixed in 1-butanol (500 mL). The reaction was heated to reflux overnight. After it cooled to room temperature, the solvent was distilled. The residue was purified by column chromatography using hexanes/ethyl acetate to give 3-nitro-N-phenylpyridin-2-amine (29 g, 85% yield).

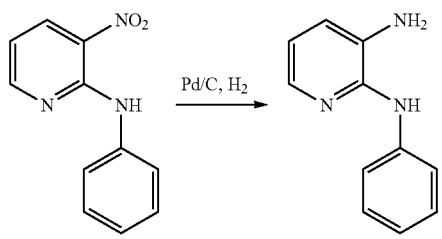 [SMILES: O=[N+]([O-])c1cccnc1Nc1ccccc1 ; Nc1cccnc1Nc1ccccc1]

Synthesis of N$^2$-phenylpyridine-2,3-diamine 3-nitro-N-phenylpyridin-2-amine (29 g, 135 mmol) and palladium on carbon (10 wt %, 3 g) in ethanol (200 mL) were hydrogenated on a Parr hydrogenator at 45 psi for 8 h. The catalyst was filtered. The solution was concentrated to give N$^2$-phenylpyridine-2,3-diamine (20 g, 80% yield).

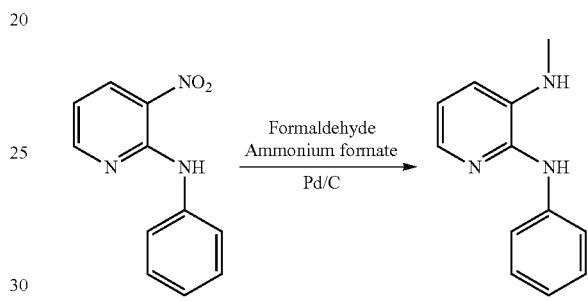

Synthesis of N$^3$-methyl-N$^2$-phenylpyridine-2,3-diamine

Pd/C (10%, 11.49 g) was added to a three-neck flask. A gentle nitrogen flow was applied to the flask. Water (40 mL) and methanol (800 mL) were added to the flask. Then, N$^2$-phenylpyridine-2,3-diamine (20 g, 108 mmol), formaldehyde (8.76 g, 108 mmol), and ammonium formate (136 g, 2160 mmol) were added. The reaction was stirred at room temperature overnight. The solution was filtered through a Celite® plug. The filtrate was concentrated and water was added. The solution was extracted with dichloromethane. The combined organic layer was concentrated and purified by column chromatography (30% ethyl acetate in hexanes) to give N$^3$-methyl-N$^2$-phenylpyridine-2,3-diamine (12 g, 55.8% yield).

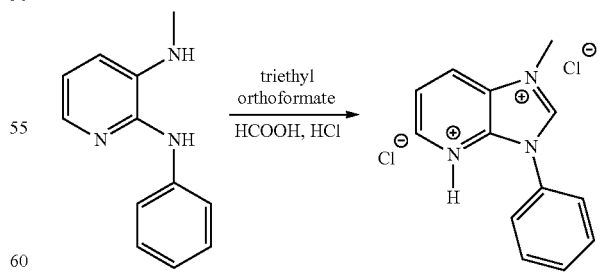

Synthesis of 3-phenyl-3H-imidazo[4,5-b]pyridine methyl salt

N$^3$-methyl-N$^2$-phenylpyridine-2,3-diamine (9 g, 45.2 mmol), concentrated HCl (2 mL), and 10 drops of formic acid were added in triethyl orthoformate (376 mL). The reaction was refluxed overnight. After it cooled to room temperature, the white solid was collected by filtration. The solid was further purified by recrystallizing from ethanol to give 3-phenyl-3H-imidazo[4,5-b]pyridine methyl salt (10 g, 79% yield).

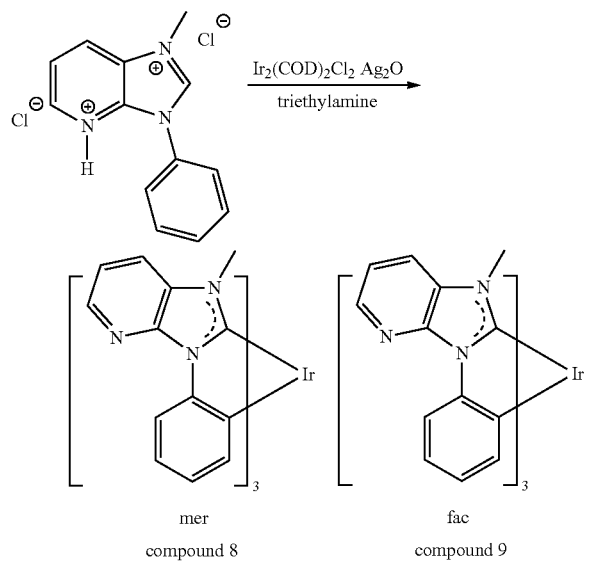

mer
compound 8 fac
compound 9

Synthesis of Compound 8 and Compound 9

The carbene precursor (9 g, 32 mmol), silver oxide (7.42 g, 32 mmol), triethylamine (3.24 g, 32 mmol), $Ir_2(COD)_2Cl_2$ (3.57 g, 5.34 mmol) and chlorobenzene (500 mL) were added to the reaction flask and heated to reflux overnight. After it cooled to room temperature, the reaction mixture was filtered through Celite®. The solution was concentrated and purified by column using dichloromethane as solvent to give Compound 8 (6 g, 70% yield) and Compound 9 (1 g, 10% yield).

Example 5

Synthesis of Compound 10

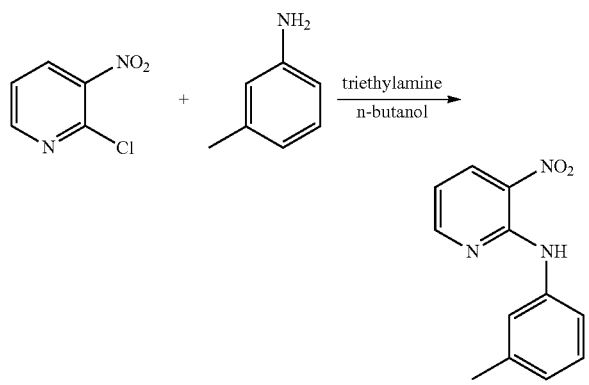

Synthesis of 3-nitro-N-(m-tolyl)pyridine-2-amine 2-chloro-3-nitropyridine (25 g, 158 mmol), m-toluidine (20.5 mL, 189 mmol), triethylamine (26.4 mL, 189 mmol), and 400 mL butanol were added to a 1 L 3-neck round-bottom flask. The reaction mixture was heated overnight under nitrogen. The solvent was evaporated leaving a bright orange solid. The solid was triturated with hexanes and filtered. The filtrate was not pure and contained product, so it was evaporated and purified by column chromatography eluting with 10 and 20% ethyl acetate/hexanes. A total of 3.15 g was obtained from the column. The bulk of the material was dissolved in dichloromethane and washed twice with water, dried over magnesium sulfate, filtered, and evaporated to an orange solid (31.2 g). The total amount obtained was 34.35 g (95%).

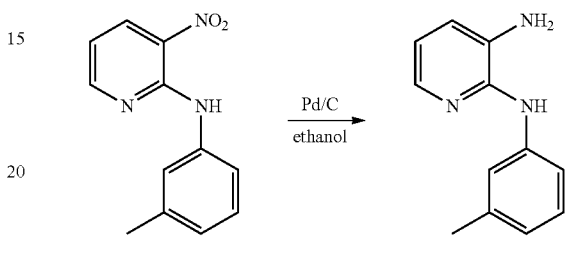

Synthesis of $N^2$-(m-tolyl)pyridine-2,3-diamine

10% palladium on carbon (10%, 1.84 g, 1.729 mmol) was added to a Parr Hydrogenator bottle. The bottle was purged with nitrogen and 3-nitro-N-(m-tolyl)pyridin-2-amine (17.97 g, 78 mmol) was added in 250 mL of ethanol. The material was hydrogenated on a Parr hydrogenator overnight. The reaction mixture was filtered through Celite®, and the Celite® was washed with dichloromethane. The filtrate was evaporated leaving a brown solid (15.44 g, 99%).

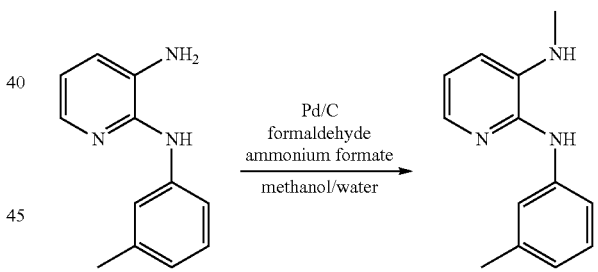

Synthesis of $N^3$-methyl-$N^2$-(m-tolyl)pyridine-2,3-diamine 600 mL of methanol and 24 mL water were added to a 3-neck 2 L round bottom flask. Nitrogen was bubbled directly into the solution. Palladium on carbon was added (10%, 10.35 g, 9.73 mmol) while bubbling continued. Next, $N^2$-(m-tolyl)pyridine-2,3-diamine (19.38 g, 97 mmol) and formaldehyde (37%, 14.48 mL, 195 mmol) were added. The reaction mixture was stirred under nitrogen for 3 h. Next, nitrogen was bubbled into the solution and ammonium formate (123 g, 1945 mmol) was added slowly. The reaction mixture was stirred under nitrogen overnight at room temperature. The reaction mixture was filtered through Celite® and the Celite® was washed with dichloromethane. The filtrate was washed with water twice, and the organic layer was dried over magnesium sulfate, filtered, and evaporated. The residue was purified using column chromatography eluting with 30% ethyl acetate/hexanes to isolate the desired product. The product was combined with material from other reactions and purified by column chromatography eluting with 30% ethyl acetate/hexanes. A dark reddish-brown solid was obtained. The solid was recrystallized from boiling hexanes with a small amount of ethyl acetate to dissolve the solid. The product was filtered off as needles with some reddish color which were washed with hexanes, obtained 15.1 g.

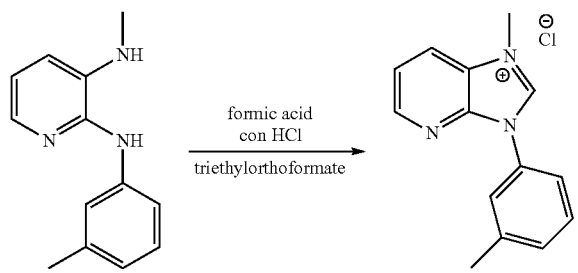 [SMILES: CNc1cccnc1Nc1cccc(C)c1 ; Cc1cccc(-n2c[n+](C)c3cccnc32)c1 ; [Cl-]]

Synthesis of 3-(m-tolyl)-3H-imidazo[4,5-b]pyridine methyl salt

In a 1 L round bottom flask, $N^3$-methyl-$N^2$-(m-tolyl)pyridine-2,3-diamine (15.1 g, 70.8 mmol), triethylorthofommate (589 ml, 3540 mmol), 15 drops of formic acid, and 3 mL of concentrated HCl were added. The reaction mixture was heated to reflux overnight under nitrogen. The reaction mixture was cooled to room temperature, and a purple solid was filtered off. The material was recrystallized from boiling ethyl acetate with enough ethanol to dissolve it. The product was isolated as needles with a purple tinge (6.7 g, 32% yield).

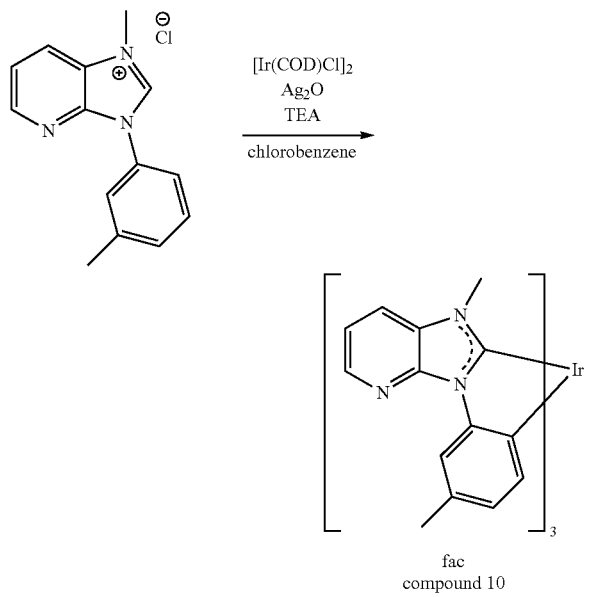

fac compound 10

Synthesis of Compound 10

350 mL chlorobenzene was added to a 1 L 3-neck round bottom flask. Nitrogen was bubbled in directly, and the imidazole salt was added (6.7 g, 22.62 mmol) as well as Ir$_2$(COD)$_2$Cl$_2$ (2.52 g, 3.77 mmol), silver oxide (5.24 g, 22.62 mmol), and triethylamine (2.289 g, 22.62 mmol). The flask was covered with aluminum foil and the mixture refluxed overnight under nitrogen. The reaction mixture was cooled and filtered through a pad of Celite®, the Celite® rinsed with dichloromethane. The filtrate was evaporated and purified by column chromatography twice, eluting with dichloromethane both times. 1.63 g of material was obtained (50% yield).

Example 6

Synthesis of Compound 11

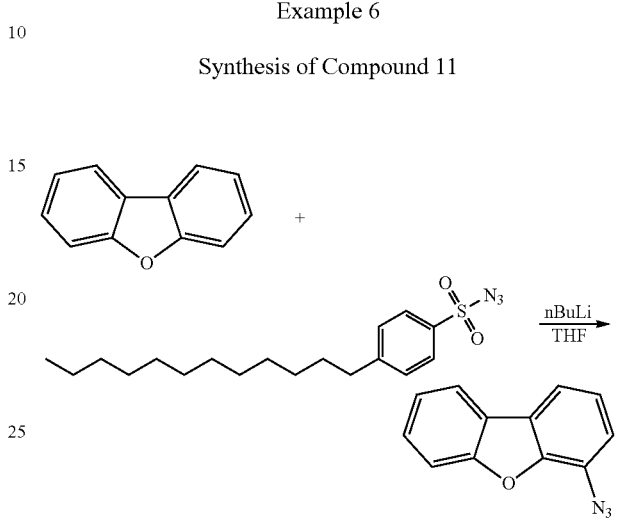

Synthesis of 4-azidodibenzo[b,d]furan

Dibenzo[b,d]furan and 114 mL THF were added to a 500 mL 3-neck round bottom flask. The solution was cooled in a dry ice/acetone bath under nitrogen. Next, butyllithium was added dropwise via dropping funnel. The reaction mixture was allowed to warm to room temperature overnight. It was cooled in a dry ice/acetone bath again, and 4-dodecylbenzenesulfonyl azide in 70 mL of THF was added dropwise via dropping funnel. The solution turned from yellow to orange after the addition. The cooling bath was removed, and the reaction mixture was stirred at room temperature for 3 h. Next, the reaction was quenched with water dropwise, diluted with 1N HCl, and extracted with ether. The ether extracts were dried over magnesium sulfate, filtered, and evaporated. The residue was purified by column chromatography eluting with 5% dichloromethane/hexanes (7.39 g, 55% yield).

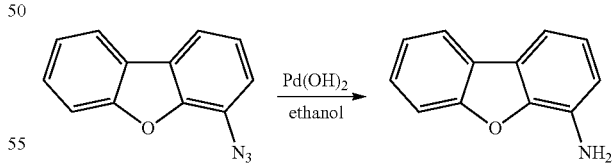

Synthesis of dibenzo[b,d]furan-4-amine

Palladium hydroxide (20%, 0.75 g, 1.068 mmol) was added to a Parr hydrogenation bottle, and the bottle was purged with nitrogen. Next, 4-azidodibenzo[b,d]furan (7.39 g, 35.3 mmol) and 150 mL ethanol were added, and the reaction mixture was hydrogenated on Parr hydrogenator overnight. The reaction mixture was filtered through a pad of Celite®, and the Celite® was washed with dichloromethane.

The filtrate was evaporated, and the residue was purified by column chromatography eluting with 50% dichloromethane/hexanes (5.58 g, 86%).

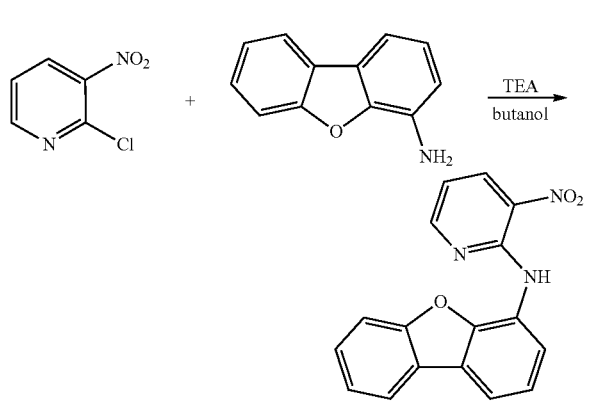

Synthesis of N-(dibenzo[b,d]furan-4-yl)-3-nitropyridin-2-amine 2-chloro-3-nitropyridine (4.39 g, 27.7 mmol), dibenzo[b,d]furan-4-amine (5.58 g, 30.5 mmol), triethylamine (4.3 mL, 30.9 mmol), and butanol (90 mL) were mixed in a 250 mL round bottom flask. The reaction mixture was refluxed overnight under nitrogen. The solvent was evaporated, leaving an orange solid which was dried under vacuum. The solid was taken up in ethyl acetate, water was added and the layers were separated. The organic layer with washed with brine, dried over magnesium sulfate, filtered, and evaporated to a residue. The residue was purified on by column chromatography eluting with 10% ethyl acetate/hexanes followed by ethyl acetate (4.6 g, 54%).

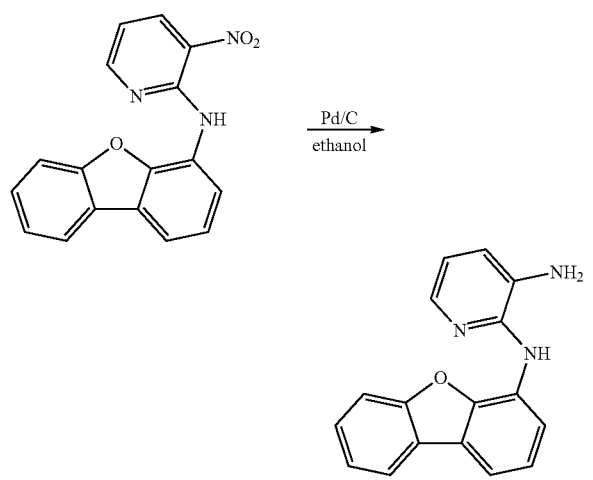

Synthesis of $N^2$-(dibenzo[b,d]furan-4-yl)pyridine-2,3-diamine

10% palladium on carbon (10%; 0.50 g, 0.47 mmol) was added to a Parr hydrogenation bottle. The bottle was purged with nitrogen. Next, N-(dibenzo[b,d]furan-4-yl)-3-nitropyridin-2-amine (3.8 g, 12.45 mmol) and 200 mL ethanol were added. The reaction mixture was hydrogenated overnight using a Parr hydrogenator. The reaction mixture was filtered through Celite® and the Celite® washed with dichloromethane and ethyl acetate. The filtrate was evaporated leaving a dark brown solid, which was not purified (3.32 g, 97%).

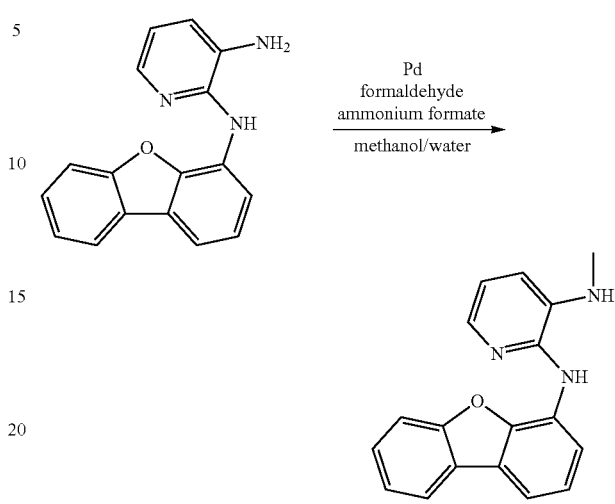

Synthesis of $N^2$-(dibenzo[b,d]furan-4-yl)-$N^3$-methylpyridine-2,3-diamine 100 mL methanol and 4 mL water were added to a 250 mL 3-neck round bottom flask. Nitrogen was bubbled directly into the solution. Palladium on carbon was added (10%, 1.71 g, 1.607 mmol) as bubbling of nitrogen continued. Next, $N^2$-(dibenzo[b,d]furan-4-yl)pyridine-2,3-diamine (3.85 g, 13.98 mmol) and formaldehyde (37%, 2.08 mL, 28.0 mmol) were added, and the mixture was stirred for 2 h under nitrogen. Nitrogen was bubbled into the solution and ammonium formate (17.64 g, 280 mmol) was added. The reaction mixture was stirred overnight under nitrogen. The mixture was filtered through a pad of Celite®, and the Celite® washed with dichloromethane. The solution was washed with water, dried over magnesium sulfate, filtered, and evaporated. The material was purified by column chromatography eluting with 20% ethyl acetate/hexanes. The product was recrystallized from boiling hexanes and a small amount of dichloromethane (0.77 g, 18% yield).

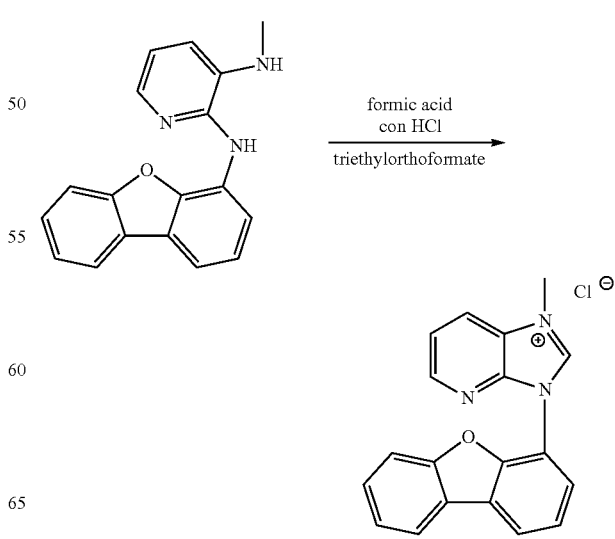

Synthesis of 3-(dibenzo[b,d]furan-4-yl)-3H-imidazo[4,5-b]pyridine methyl salt $N^2$-(dibenzo[b,d]furan-4-yl)-$N^3$-methylpyridine-2,3-diamine (0.77 g, 2.66 mmol), triethylorthoformate (22 mL, 132 mmol), 15 drops concentrated HCl, and 3 drops formic acid were added to a 100 mL round bottom flask. The reaction mixture was heated to reflux overnight under nitrogen, and a solid precipitated out. The solid was filtered; washed with a small amount of methanol, and dried under vacuum (0.3 g, 30%).

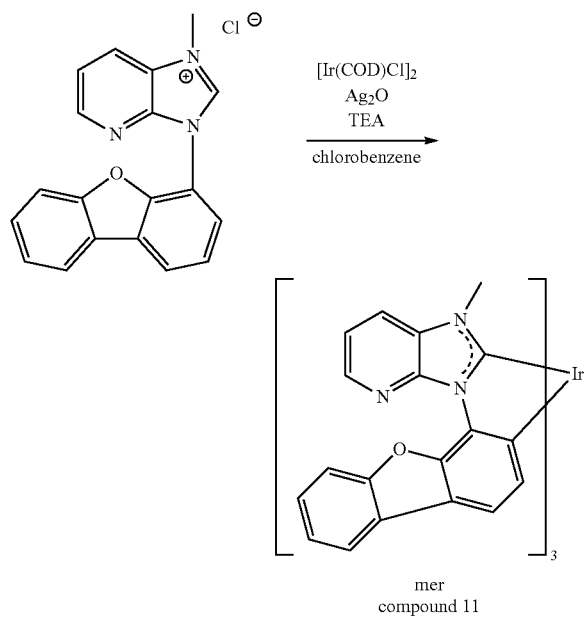

mer
compound 11

Synthesis of Compound 11

20 mL of chlorobenzene was added to a 100 mL round-bottom flask, and was degassed by bubbling nitrogen into solvent. To the solvent was added the imidazole salt (0.30 g, 0.806 mmol), $Ir_2(COD)_2Cl_2$ (0.090 g, 0.134 mmol), silver oxide (0.187 g, 0.806 mmol), and triethylamine (0.112 mL, 0.806 mmol). The flask was covered with aluminum foil, and the mixture refluxed overnight under nitrogen. The next day, the mixture was cooled and filtered through a pad of Celite®. The Celite® pad was washed with dichloromethane, and the filtrate evaporated. The residue was purified by column chromatography eluting with 5% ethyl acetate/dichloromethane twice (70 mg, 48%).

Example 7

Synthesis of Compound 12 and Compound 13

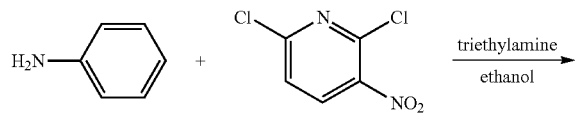

Synthesis of 6-chloro-3-nitro-N-phenylpyridin-2-amine

A mixture of aniline (7.24 g, 78 mmol), triethylamine (13 mL, 93 mmol), and 2,6-dichloro-3-nitropyridine (15 g, 78 mmol) was stirred overnight in 500 mL ethanol at room temperature under nitrogen. The solid that formed was filtered off, washed with water and ethanol, and dried. The solid was purified by column chromatography eluting with 20% ethyl acetate/hexane (8.62 g, 44%).

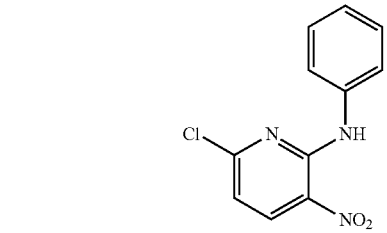

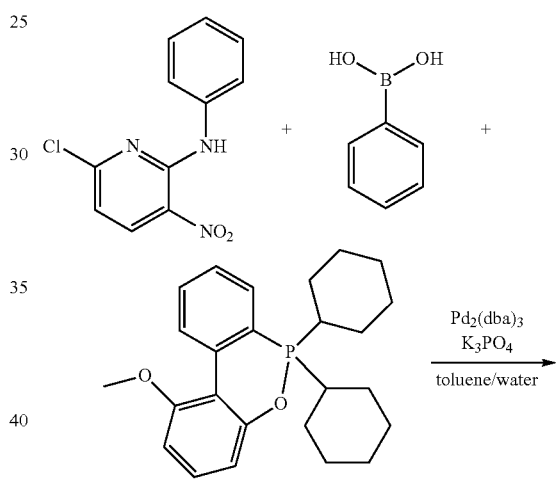

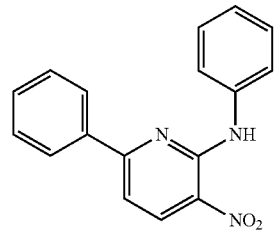

Synthesis of 3-nitro-N-6-diphenylpyridin-2-amine 6-chloro-3-nitro-N-phenylpyridin-2-amine (8.62 g, 34.5 mmol), phenylboronic acid (5.05 g, 41.4 mmol), dicyclohexyl(2',6'-dimethoxy-[1,1'-biphenyl]-2-yl)phosphine (0.567 g, 1.381 mmol), potassium phosphate tribasic monohydrate (23.85 g, 104 mmol), 300 mL toluene and 30 mL water were added to a 3-neck 1000 mL round bottom flask. Nitrogen was bubbled directly into the mixture for 20 minutes. $Pd_2(dba)_3$ (0.316 g, 0.345 mmol) was added and the mixture refluxed overnight under nitrogen. The reaction mixture was diluted with ethyl acetate/water. The layers were separated, and the aqueous layer was extracted with ethyl acetate. The organic layers were dried over magnesium sulfate, filtered, and evaporated to a residue. The residue was purified by column chromatography eluting with 20% ethyl acetate/hexanes initially, and ethyl acetate was added to flush off the product. The product was washed with hexanes (7.58 g, 75%).

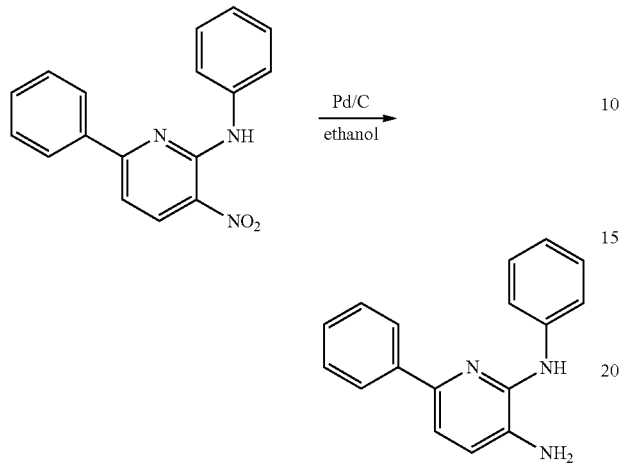

Synthesis of N-2,6-diphenylpyridine-2,3-diamine

Palladium on carbon (10%, 0.8 g, 0.752 mmol) was added to a Parr Hydrogenator bottle. The bottle was purged with nitrogen, and 3-nitro-N-6-diphenylpyridin-2-amine (7.58 g, 26.0 mmol) in 150 mL of ethanol was added. The material was hydrogenated overnight on a Parr hydrogenator. The mixture was filtered through Celite® to remove the palladium on carbon. The Celite® pad was washed with dichloromethane and evaporated to a dark brown solid (6.3 g, 93%).

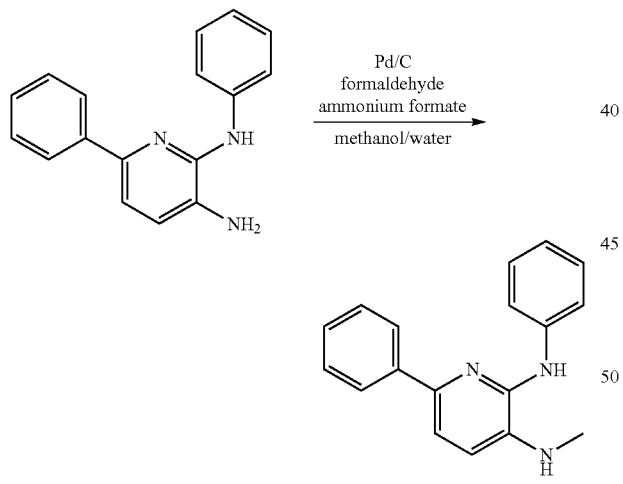

Synthesis of N3-methyl-N-2,6-diphenylpyridine-2,3-diamine 200 mL of methanol and 8 mL of water was added to a 500 mL 3-neck round bottom flask. Nitrogen was bubbled into the liquid. Next, palladium on carbon was added (10%, 2.57 g, 2.411 mmol), followed by N-2,6-diphenylpyridine-2,3-diamine (6.3 g, 24.11 mmol) and formaldehyde in water solution (37%, 3.59 mL, 48.2 mmol). The mixture was stirred at room temperature under nitrogen for 3 h. Then, nitrogen was bubbled into the mixture and ammonium formate (30.4 g, 482 mmol) was added. The reaction mixture was stirred overnight at room temperature under nitrogen. Next, the reaction mixture was filtered through a pad of Celite® and washed Celite® with dichloromethane. The filtrate was evaporated and the residue partitioned between ethyl acetate and water. The layers were separated and the aqueous layer extracted with ethyl acetate. The organic layers were dried over magnesium sulfate, filtered, and evaporated leaving a residue. The residue was purified by column chromatography eluting with 20% ethyl acetate/hexanes twice (2.57 g, 39%).

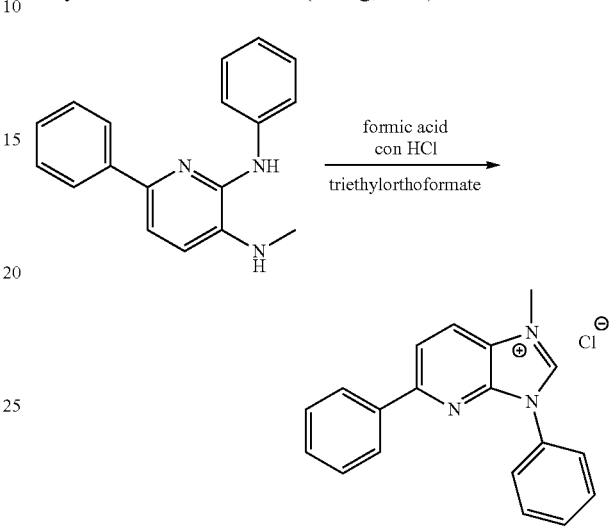

Synthesis of 3,5-diphenyl-3H-imidazo[4,5-b]pyridine methyl salt $N^3$-methyl-N-2,6-diphenylpyridine-2,3-diamine (2.57 g, 9.33 mmol), triethyl orthoformate (100 mL, 601 mmol), 0.4 mL concentrated HCl, and a few drops of formic acid were added to a 500 mL round bottom flask. The mixture was heated to reflux overnight under nitrogen. The mixture was cooled, and a solid was filtered off and rinsed with hexanes. The solid was recrystallized from boiling ethyl acetate and a small amount of ethanol (1.3 g, 39%).

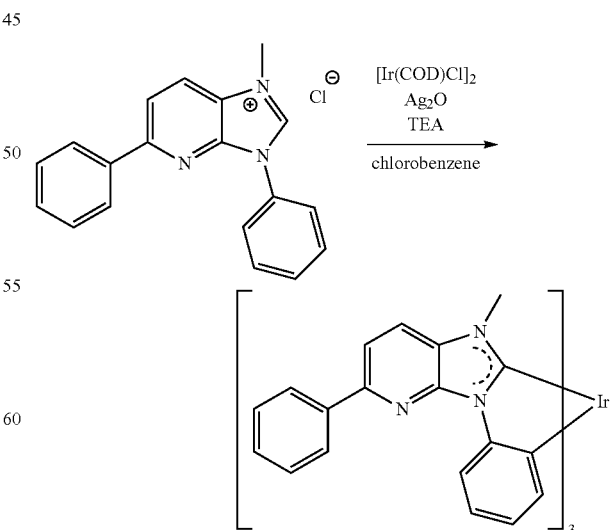

mer = compound 12
fac = compound 13

Synthesis of Compounds 12 and 13

60 mL of chlorobenzene was added to a 250 mL round bottom flask. Nitrogen was bubbled into the chlorobenzene, and the imidazole salt (1.30 g, 3.64 mmol), Ir$_2$(COD)$_2$Cl$_2$ (0.406 g, 0.606 mmol), silver(I) oxide (0.843 g, 3.64 mmol), and triethylamine (0.507 mL, 3.64 mmol) was added to the flask. The flask was covered with aluminum foil, and the mixture heated to reflux overnight under nitrogen. The reaction mixture was filtered through Celite®, washed Celite® with dichloromethane. The filtrate was evaporated leaving a residue which was purified by column chromatography eluting with 70% dichloromethane/hexanes. The first spot was collected cleanly as the mer isomer (Compound 12), 0.27 g. The second spot was collected and purified material again by column chromatography eluting with 60 and 70% dichloromethane/hexanes, isolated as the fac isomer (Compound 13), 0.22 g. A total of 0.49 g was obtained (39% yield).

Example 8

Synthesis of Compound 14 and Compound 15

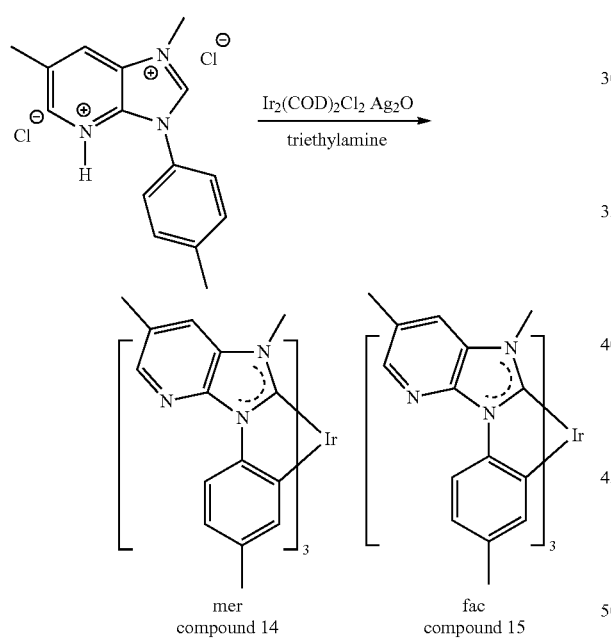

mer
compound 14 fac
compound 15

Synthesis of Compound 14 and Compound 15

The ligand precursor was prepared the same way as the ligand for Compound 8. The carbene precursor (4.4 g, 14.2 mmol), silver oxide (3.3 g, 14.2 mmol), triethylamine (1.44 g, 14.2 mmol), Ir$_2$(COD)$_2$Cl$_2$ (1.59 g, 2.4 mmol) and chlorobenzene (300 mL) were added to the reaction flask and heated to reflux overnight under nitrogen. After it cooled to room temperature, the reaction mixture was filtered through Celite®. The solution was concentrated and purified by column using dichloromethane as solvent to give Compound 14 (1.3 g, 30% yield), then 5% ethyl acetate in dichloromethane to give Compound 15 (1.8 g, 42% yield).

Example 9

Synthesis of Compound 16 and Compound 17

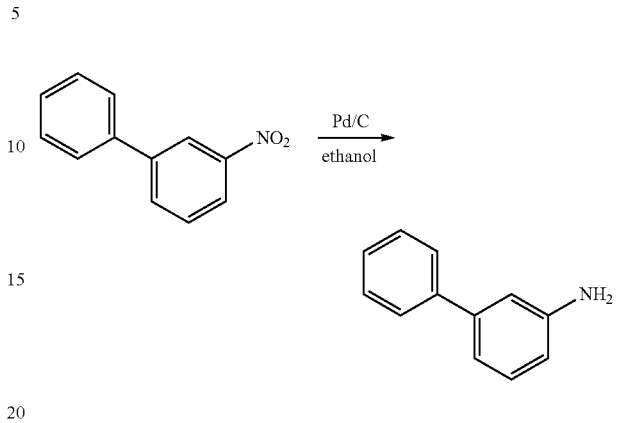

Synthesis of [1,1'-biphenyl]-3-amine

Palladium on carbon (10%, 0.70 g, 0.658 mmol) was added to a Parr hydrogenator bottle. The bottle was purged with nitrogen. Next, 3-nitro-1,1'-biphenyl (10 g, 50.2 mmol) and 190 mL ethanol were added to the bottle. The material was hydrogenated on a Parr hydrogenator. After 3 h, the reaction mixture was filtered through Celite® and the Celite® washed with dichloromethane. The filtrate was evaporated, obtained a brown oil, 8.69 g, assume quantitative yield (8.49 g).

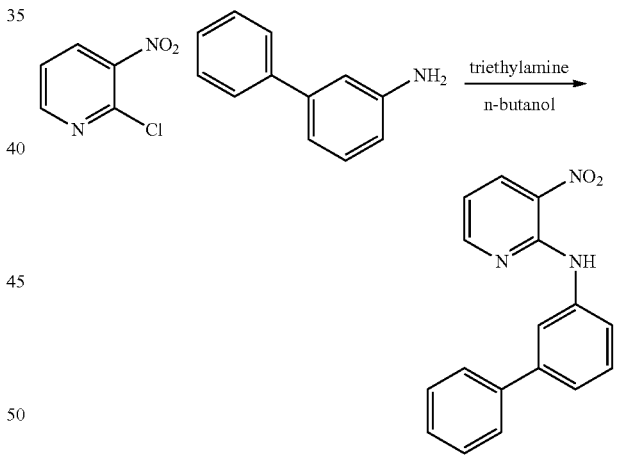

Synthesis of N-([1,1'-biphenyl]-3-yl)-3-nitropyridin-2-amine

[1,1'-biphenyl]-3-amine (8.49 g, 50.2 mmol), 2-chloro-3-nitropyridine (7.23 g, 45.6 mmol), triethylamine (6.99 mL, 50.2 mmol), and 200 mL of butanol were added to a 1 L round bottom flask. The mixture was refluxed overnight under nitrogen. The next day the solvent was evaporated, and the residue was taken up in dichloromethane and washed twice with water. The organic layer was dried over magnesium sulfate, filtered, and evaporated leaving an orange oil. 14.61 g, assume quantitative yield (13.29 g).

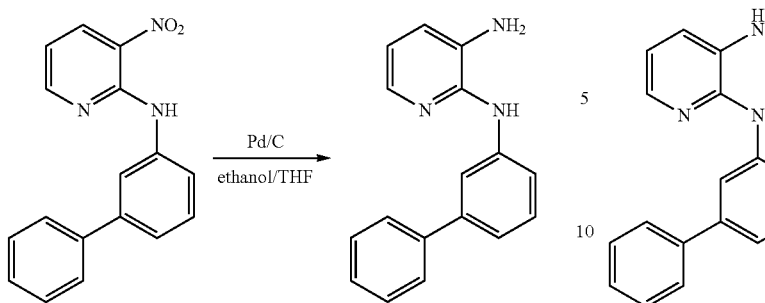

Synthesis of N²-([1,1'-biphenyl]-3-yl)pyridine-2,3-diamine 1.40 g of palladium on carbon (10%, 1.40 g, 1.316 mmol) was added to a Parr Hydrogenation bottle. The bottle was purged with nitrogen, and N-([1,1'-biphenyl]-3-yl)-3-nitropyridin-2-amine was added (13.29 g, 45.6 mmol) in 175 mL ethanol and 25 mL THF. The reaction mixture was hydrogenated overnight using a Parr hydrogenator. The reaction mixture was filtered through Celite®, washed Celite® with dichloromethane, evaporated filtrate to yield a tan solid with quantitiative yield.

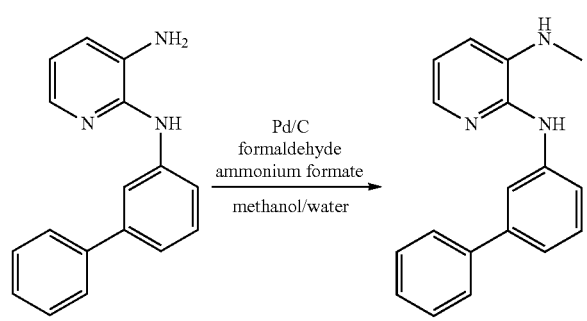 [SMILES: Nc1cccnc1Nc1cccc(-c2ccccc2)c1 ; CNc1cccnc1Nc1cccc(-c2ccccc2)c1]

Synthesis of N²-([1,1'-biphenyl]-3-yl)-N3-methylpyridine-2,3-diamine 325 mL of methanol and 13 mL of water were added to a 1 L 3-neck round bottom flask. Nitrogen was bubbled into the liquid. Palladium on carbon was added (10%, 5.55 g, 5.22 mmol) followed by N²-([1,1'-biphenyl)pyridine-2,3-diamine (13.63 g, 52.2 mmol) and formaldehyde in water solution (37%, 7.77 mL, 104 mmol). The mixture was stirred at room temperature under nitrogen for 2 h, then nitrogen was bubbled into the mixture and added ammonium formate (65.8 g, 1043 mmol). The reaction mixture was stirred overnight at room temperature under nitrogen. The mixture was filtered through a pad of Celite®, and washed Celite® with dichloromethane. The filtrate was evaporated and the residue partitioned between dichloromethane and water. The layers were separated and the aqueous layer extracted with dichloromethane. The organic layers were dried over magnesium sulfate, filtered, and evaporated leaving a brown oil. The material was purifed by column chromatography eluting with 30% ethyl acetate/hexanes to obtain product (5.37 g, 37%).

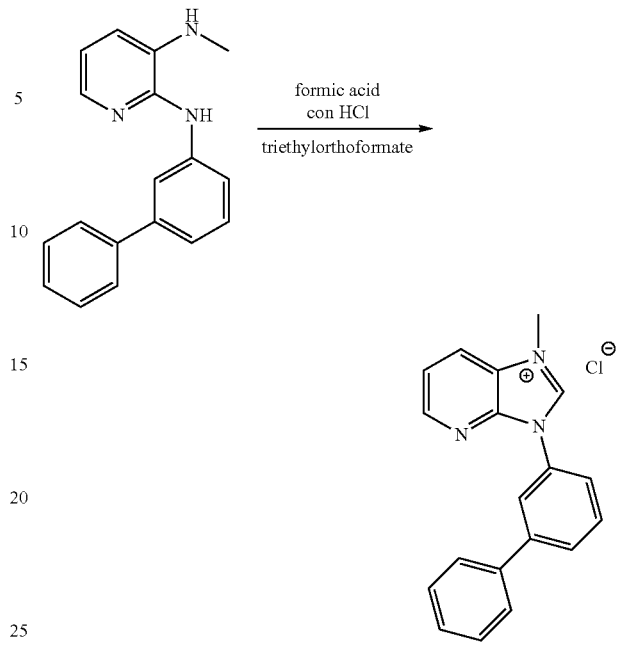

Synthesis of 3-([1,1'-biphenyl]-3-yl)-3H-imidazo[4,5-b]pyridine methyl salt

N²-([1,1'-biphenyl]-3-yl)-N3-methylpyridine-2,3-diamine (5.37 g, 19.50 mmol), triethyl orthoformate (162 mL, 975 mmol), 1.0 mL concentrated HCl, and 8 drops of formic acid were added in a 500 mL round bottom flask. The mixture was heated to 85° C. overnight under nitrogen. A solid was filtered off and washed with ethyl acetate. The solid was recrystallized from ethyl acetate and small amount of ethanol (3.0 g, 43%).

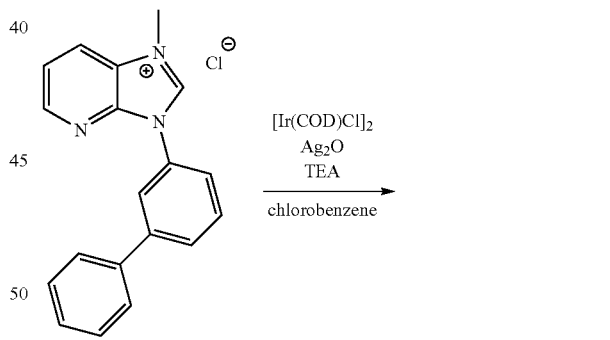

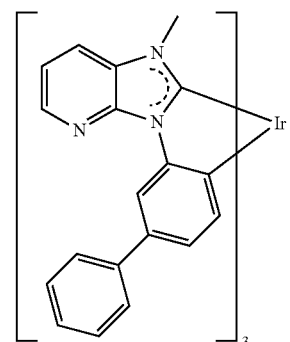

mer = compound 16
fac = compound 17

Synthesis of Compound 16 and Compound 17

120 mL of chlorobenzene was added to a 250 mL round bottom flask. Nitrogen was bubbled into the chlorobenzene, and the imidazole salt (3.00 g, 8.40 mmol), Ir$_2$(COD)$_2$Cl$_2$ (0.937 g, 1.400 mmol), silver(I) oxide (1.946 g, 8.40 mmol), and triethylamine (1.170 mL, 8.40 mmol) were added to the flask. The flask was covered with aluminum foil, and the mixture heated to reflux overnight under nitrogen. The reaction mixture was filtered through Celite®, and then the Celite® was washed with dichloromethane. The filtrate was evaporated, the residue purified by silica gel plug and eluted with dichloromethane. The material was collected and purified by column chromatography eluting with 80% dichloromethane/hexanes followed by pure dichloromethane. The first compound was collected as the mer isomer, Compound 16 (1 g). The second compound was collected as fac isomer isomer which was purified by column chromatography eluting with dichloromethane Compound 17 (1 g). The total amount of material obtained is 2 g, 68% yield.

Example 10

Synthesis of Compound 18 and Compound 19

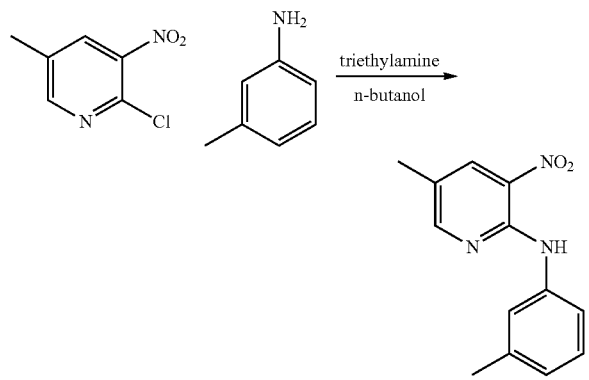

Synthesis of 5-methyl-3-nitro-N-(m-tolyl)pyridine-2-amine

A mixture of 2-chloro-5-methyl-3-nitropyridine (13 g, 75 mmol), triethylamine (12.6 mL, 90 mmol), and m-toluidine (9.8 mL, 90 mmol) in 200 mL butanol was heated overnight under nitrogen. The solvent was evaporated, and the residue dissolved in dichloromethane. The organic layer was washed twice with water, brine, dried over magnesium sulfate, filtered, and evaporated (15.5 g, 85%).

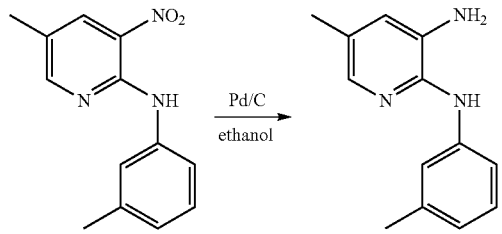 [SMILES: Cc1cccc(Nc2ncc(C)cc2[N+](=O)[O-])c1 ; Cc1cccc(Nc2ncc(C)cc2N)c1]

Synthesis of 5-methyl-N$^2$-(m-tolyl)pyridine-2,3-diamine

Palladium on carbon (10%, 1.55 g, 1.456 mmol) was added to a Parr Hydrogenator bottle. The bottle was purged with nitrogen. Then, 5-methyl-3-nitro-N-(m-tolyl)pyridin-2-amine (15.5 g, 63.7 mmol) in 90 mL of ethanol and 90 mL of THF was added. The material was hydrogenated overnight on a Parr Hydrogenator. The mixture was filtered through Celite® to remove the palladium on carbon. The Celite® pad was washed with dichloromethane and evaporated to a solid (13.5 g, 99%).

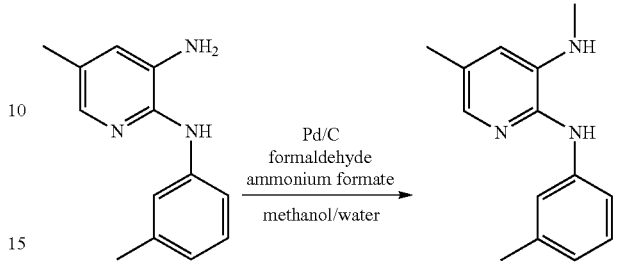

Synthesis of N-3,5-dimethyl-N$^2$(m-tolyl)pyridine-2,3-diamine 400 mL of methanol and 16 mL of water were added to a 1 L 3-neck round bottom flask. Nitrogen was bubbled into the liquid and palladium on carbon was added (10%, 6.71 g, 6.30 mmol). Then, 5-methyl-N$^2$-(m-tolyl)pyridine-2,3-diamine (13.44 g, 63.0 mmol) and formaldehyde in water solution (37%, 9.38 mL, 126 mmol) were also added. Methanol (100 mL) was used to aid in the transfer of the diamine. The mixture was stirred at room temperature under nitrogen for 2 h, then nitrogen was bubbled into mixture and ammonium formate (79 g, 1260 mmol) was added. The reaction mixture was stirred overnight at room temperature under nitrogen for one week. The reaction mixture was filtered through Celite® and the Celite® washed with dichloromethane. The filtrate was evaporated, and water was added. The mixture was extracted twice with dichloromethane, dried over magnesium sulfate, filtered, and evaporated. The residue was purified by column chromatography eluting with 30% ethyl acetate/hexanes to give product (5.31 g, 37%).

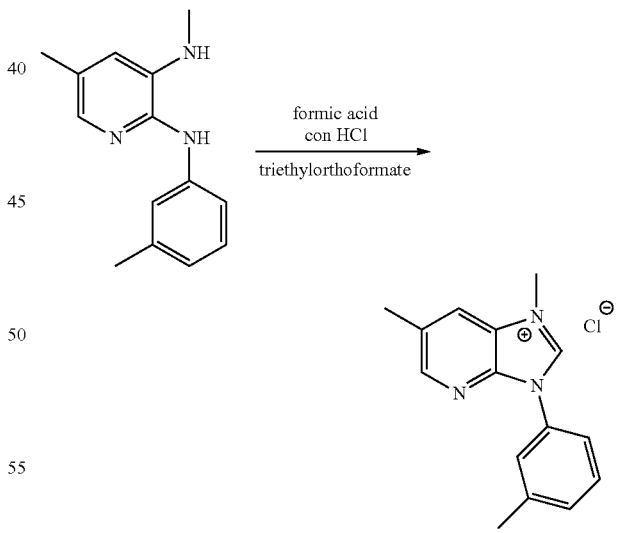

Synthesis of 6-methyl-3-(m-tolyl)-3H-imidazo[4,5-b]pyridine methyl salt

N-3,5-dimethyl-N$^2$(m-tolyl)pyridine-2,3-diamine (5.31 g, 23.36 mmol), triethyl orthoformate (194 mL, 1168 mmol), 0.8 mL concentrated HCl, and 6 drops of formic acid were added to a 500 mL round bottom flask. The mixture was heated to 85° C. overnight under nitrogen. The reaction mixture was cooled in an ice bath and diluted with ethyl acetate. A solid was filtered off, rinsed with ethyl acetate and dried in a vacuum oven (2.66 g, 37%).

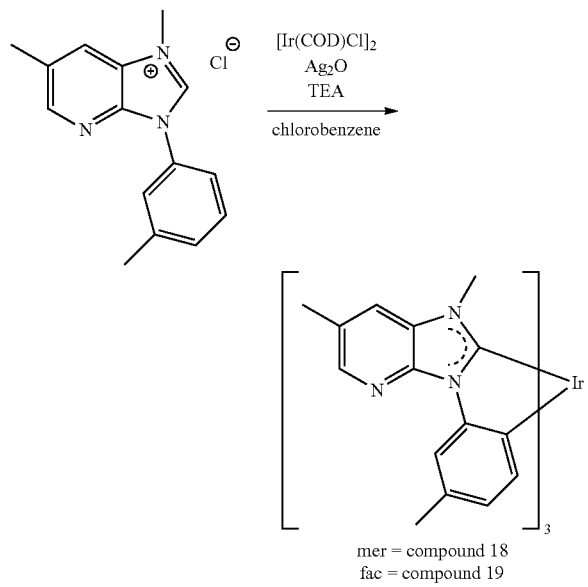

mer = compound 18
fac = compound 19

Synthesis of Compound 18 and Compound 19

120 mL of chlorobenzene was added to a 250 mL round bottom flask. Nitrogen was bubbled into the chlorobenzene and the imidazole salt (2.66 g, 8.60 mmol), $Ir_2(COD)_2Cl_2$ (0.960 g, 1.434 mmol), silver(I) oxide (1.993 g, 8.60 mmol), and triethylamine (1.199 mL, 8.60 mmol) were added to the flask. The flask was covered with aluminum foil and the mixture heated to reflux overnight under nitrogen. The reaction mixture was filtered through Celite®, and the Celite® was washed with dichloromethane. The filtrate was evaporated and the residue was purified by column eluting with dichloromethane. The material was collected as a mixture of mer and fac. The mixture was purified by column chromatography eluting with 50% ethyl acetate/hexanes to isolate the mer isomer which was purified again by column chromatography eluting with 5:2:3 hexanes:ethyl acetate:dichloromethane. A total of 1.04 g of the mer isomer, Compound 18 was isolated. Next, dichloromethane was eluted to isolate the fac isomer, Compound 19 (0.61 g). The total amount of material obtained is 1.65 g, 64% yield.

Example 11

Synthesis of Compound 20

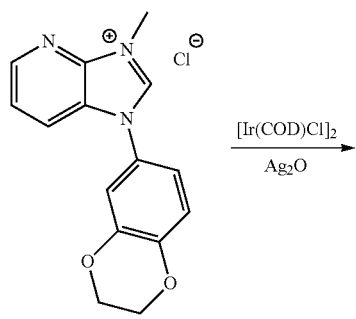

-continued

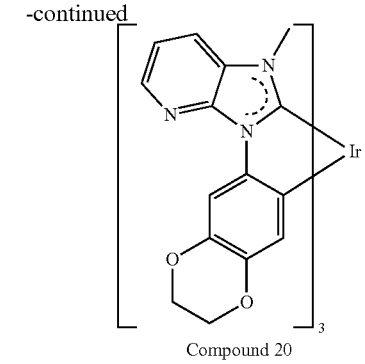

Compound 20

Synthesis of Compound 20

Iridium dimer (1 g, 1.493 mmol), 1-(2,3-dihydrobenzo[b][1,4]dioxin-6-yl)-3-methyl-1H-imidazo[4,5-b]pyridin-3-ium chloride (3.67 g, 12.10 mmol) and silver(I) oxide (2.77 g, 11.95 mmol) were added to 75 mL DMF and degassed with nitrogen for 30 minutes. Reaction mixture was heated to reflux for 24 h. Upon cooling to room temperature, the reaction mixture was diluted with 1:2 mixture of ether and hexanes (200 mL) and filtered through a Celite® plug. Compound 20 (1.5 g, 51% yield) was finally purified by column chromatography over silica gel using THF/hexanes as eluent.

Example 12

Synthesis of Compound 21

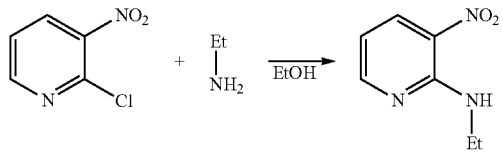

Synthesis of N-ethyl-3-nitropyridin-2-amine

2-Chloro-3-nitropyridine (20.00 g, 126 mmol) was added to ethylamine in ethanol (40 mL, 80 mmol) at room temperature and kept overnight. The solution was evaporated, the residue was diluted with 150 mL of EtOAc, washed with aqueous $NaHCO_3$ and purified by column chromatography on silica gel (hexane/ethyl acetate 4/1) to give yellow solid (19.5 g, 92%).

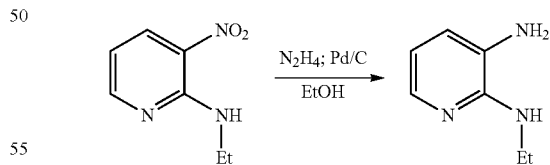

Synthesis of $N^2$-ethylpyridine-2,3-diamine

N-ethyl-3-nitropyridin-2-amine (19.50 g, 117 mmol) was dissolved in 200 mL of ethanol at room temperature with suspended palladium on carbon 10% (1 g, 9.40 mmol). A solution of hydrazine (14.95 g, 467 mmol) in 50 mL of ethanol was added dropwise at room temperature, and reaction was stirred overnight. Filtering through Celite® pad and evaporation provided $N^2$-ethylpyridine-2,3-diamine as a dark red solid (12 g, 75%).

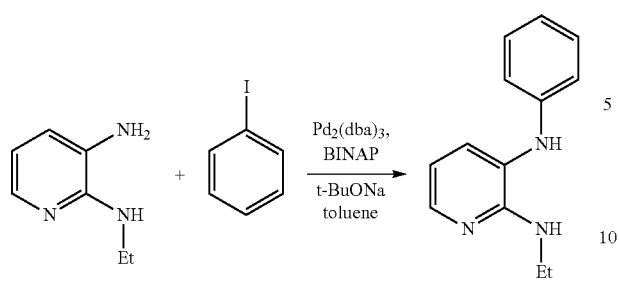

Synthesis of $N^2$-ethyl-$N^3$-phenylpyridine-2,3-diamine $N^2$-ethylpyridine-2,3-diamine (16.00 g, 117 mmol) and iodobenzene (19.61 mL, 175 mmol) were suspended in 300 mL of toluene. 8,8'-Bis(diphenylphosphino)-1,1'-binaphthalene (BINAP) (2.179 g, 3.50 mmol) and $Pd_2$ $dba_3$ (2.136 g, 2.333 mmol) were added, followed by sodium 2-methylpropan-2-olate (16.81 g, 175 mmol). The reaction flask was filled with nitrogen, stirred and refluxed overnight. The reaction mixture was cooled down, filtered through a silica plug and evaporated. The residue was purified by column chromatography on silica gel (hexane/ethyl acetate 4/1) to provide $N^2$-ethyl-$N^3$-phenylpyridine-2,3-diamine as a brown solid (8.5 g, 34%).

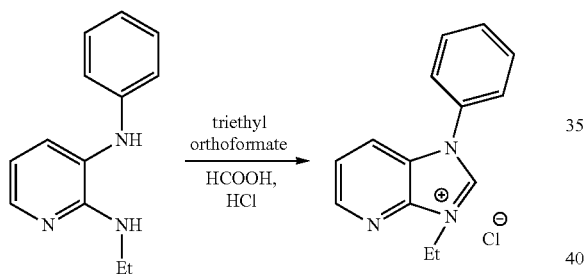

Synthesis of 3-chloro-3-ethyl-1-phenyl-2,3-dihydro-1H-imidazo[4,5-b]pyridin-3-ium-2-ide $N^2$-ethyl-$N^3$-phenylpyridine-2,3-diamine (8.5 g, 40 mmol), concentrated HCl (6 mL), and 4 mL of formic acid were added to the triethyl orthoformate (376 mL). The reaction was refluxed overnight. After it cooled to room temperature, the beige solid was collected by filtration. The solid was further purified by recrystallizing from ethanol to give 3-chloro-3-ethyl-1-phenyl-2,3-dihydro-1H-imidazo[4,5-b]pyridin-3-ium-2-ide (9.4 g, 91% yield).

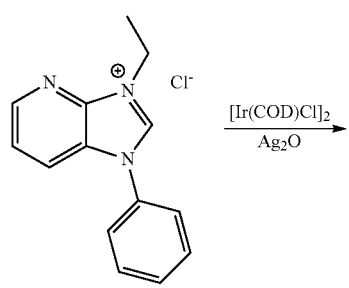

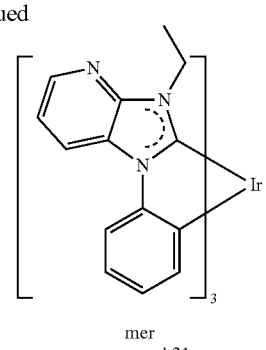

mer
compound 21

Synthesis of Compound 21

Iridium dimer (1.00 g, 1.493 mmol), carbene ligand precursor (2.327 g, 8.96 mmol) and silver(I) oxide (2.076 g, 8.96 mmol) were added to 166 mL DMF and degassed with bubbled nitrogen for 30 minutes. The reaction mixture was heated to reflux for 24 h. Upon cooling, reaction mixture was filtered through a Celite® plug and organic solvents were removed from filtrate via distillation. Crude product was dissolved in dichloromethane, washed with dilute $Na_2CO_3$ solution and dried. Compound 21 (0.4 g, 31% yield) was obtained after column chromatography of crude material using dichloromethane as solvent.

Example 13

Synthesis of Compound 22

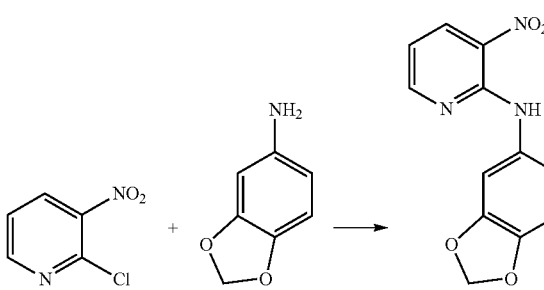

Synthesis of N-(benzo[d][1,3]dioxol-5-yl)-3-nitropyridin-2-amine

A 500 mL round bottom flask was charged with 2-chloro-3-nitropyridine (12.0 g, 76.0 mmol), 3,4-(methylenedioxy)aniline (12.97 g, 95.0 mmol), sodium acetate (7.76 g, 95.0 mmol) and acetic acid (200 mL). This was stirred at reflux for 6 h. The solvent was evaporated on a rotovap, and the crude product was column chromatographed with silica gel using a mobile phase gradient of 50-100% dichloromethane in hexane to give N-(benzo[d][1,3]dioxol-5-yl)-3-nitropyridin-2-amine (13.1 g, 67%) as a red solid.

Synthesis of N²-(benzo[d][1,3]dioxol-5-yl)pyridine-2,3-diamine

The N-(benzo[d][1,3]dioxol-5-yl)-3-nitiopyridin-2-amine was hydrogenated in a 1:1 mixture of ethyl acetate and ethanol using Pd/C 10% (2 g) under 35 psi of hydrogen. The product was chromatographed using a gradient of 50-100% ethyl acetate in dichloromethane to afford N²-(benzo[d][1,3]dioxol-5-yl)pyridine-2,3-diamine.

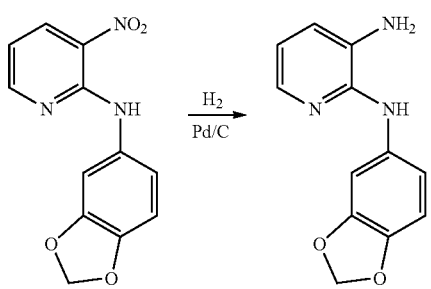 [SMILES: O=[N+]([O-])c1cccnc1Nc1ccc2c(c1)OCO2 ; "H2" ; Nc1cccnc1Nc1ccc2c(c1)OCO2]

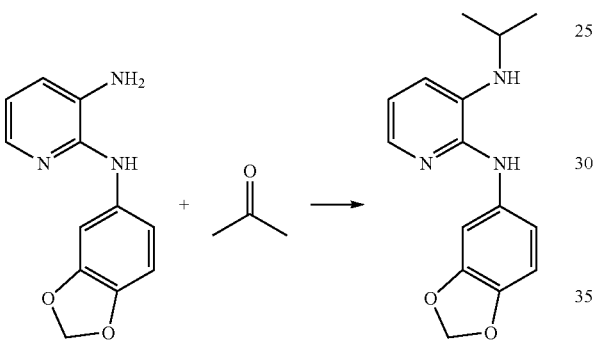

Synthesis of N²-(benzo[d][1,3]-dioxol-5-yl)-N³-isopropylpyridine-2,3-diamine

The N²-(benzo[d][1,3]dioxol-5-yl)pyridine-2,3-diamine (8.5 g, 37.1 mmol) was dissolved in dichloromethane (150 mL). Acetone (4.1 mL, 55.6 mmol), sodium triacetoxyborohydride (11.79 g, 55.6 mmol) and acetic acid (4.2 mL, 74.2 mmol) were added to it. This was stirred at ambient temperature for 18 h. The mixture was washed with 1N NaOH and then washed with water. The organic layer was concentrated in vacuo and chromatographed using a gradient of 0-10% ethyl acetate in dichloromethane to give N²-(benzo[d][1,3]dioxol-5-yl)-N³-isopropylpyridine-2,3-diamine (7.8 grams, 78%).

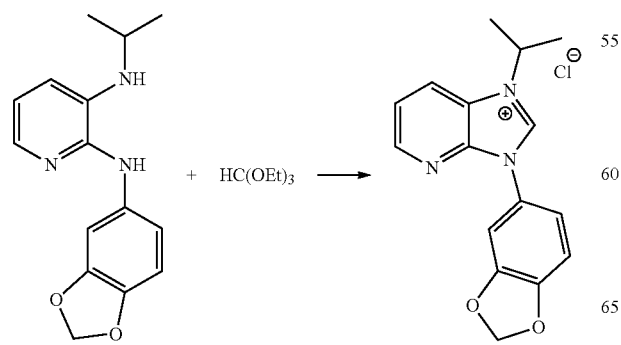

Synthesis of 3-(benzo[d][1,3]dioxol-5-yl)-1-isopropyl-3H-imidazo[4,5-b]pyridin-1-ium chloride The diamino pyridine (7.78 g, 28.7 mmol) was stirred in triethylorthoformate (189 mL). Concentrated HCl (2.4 mL) and formic acid (11 μL) were added and this was stirred at reflux overnight. The mixture was concentrated in vacuo and hexane was then added to give 3-(benzo[d][1,3]dioxol-5-yl)-1-isopropyl-3H-imidazo[4, 5-1)]pyridin-1-ium chloride (6.81 g, 75%) as a pink powder which was filtered and washed with hexane.

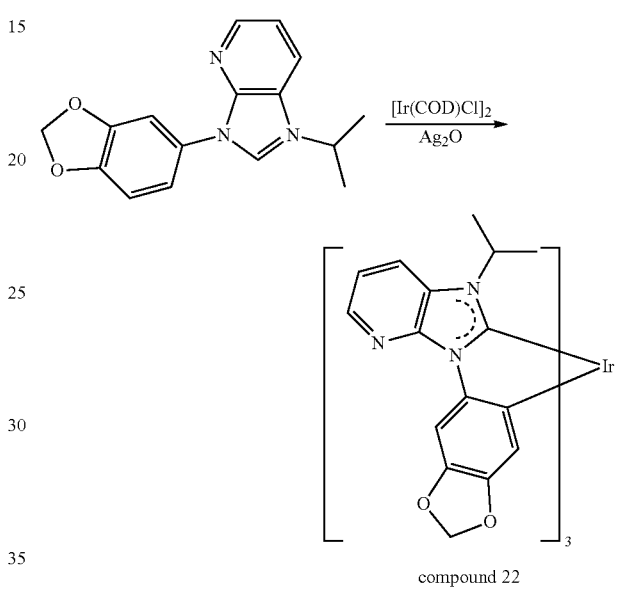

compound 22

Synthesis of Compound 22

Iridium dimer (1 g, 1.493 mmol), 3-(benzo[d][1,3]dioxol-5-yl)-1-isopropyl-3H-imidazo[4,5-b]pyridin-1-ium chloride (3.37 g, 11.95 mmol), and silver(I) oxide (2.80 g, 12.10 mmol) were added to 15 mL degassed DMF in a three neck flask. The reaction mixture was degassed further for another 20 minutes and heated to 150° C. for 24 h. Crude reaction mixture was filtered through a Celite® plug and solvents were removed under reduced pressure. Compound 22 (0.9 g, 58%) was isolated from crude by column chromatography over silica gel using THF/dichloromethane/hexanes as eluent.

Example 14

Synthesis of Compound 24

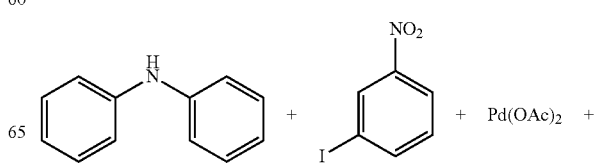

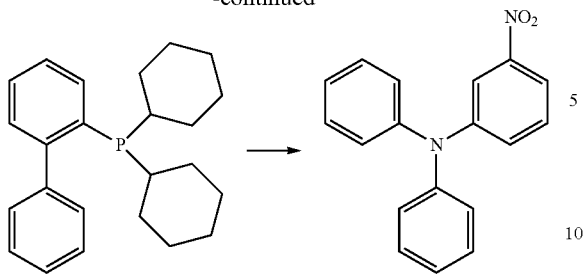

Synthesis of 3-nitro-N,N-diphenylaniline

A 1 L round bottom flask was charged with diphenylamine (13.29 g, 79.0 mmol), 1-iodo-3-nitrobenzene (19.56 g, 79.0 mmol), palladium (II) acetate (0.70 g, 3.12 mmol), biphenyl-2-dicyclohexylphosphine (2.19 g, 6.25 mmol), sodium tert-butoxide (10.48 g, 109 mmol) and toluene (400 mL). This was stirred at reflux for 18 h. The mixture was then filtered. The filtrate was concentrated in vacuo, and the crude product was chromatographed (silica gel) using a gradient of 10-20% dichloromethane in hexane to give 3-nitro-N,N-diphenylaniline (14.15 g, 62%) as an orange solid.

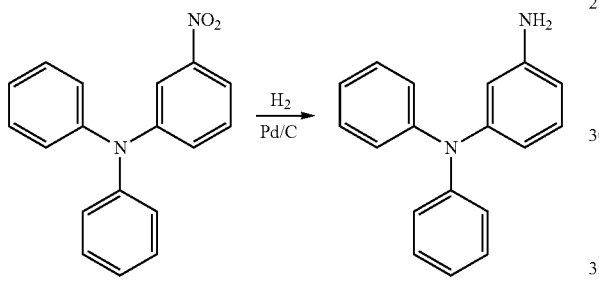

Synthesis of $N^1,N^1$-diphenylbenzene-1,3-diamine

A hydrogenation bottle was charged with 3-nitrotriphenylamine (14.0 g, 48.2 mmol), Pd/C 10% (3 g) and ethyl acetate (300 mL). This was shaken under 40 psi of hydrogen for 1 h. The mixture was filtered and the filtrate was chromatographed using a gradient of 20-100% dichloromethane in hexane to give $N^1,N^1$-diphenylbenzene-1,3-diamine (10.97 g, 87.4% yield).

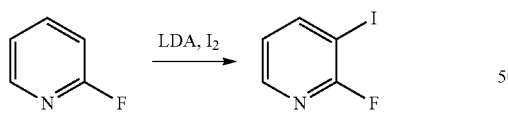

Synthesis of 2-fluoro-3-iodopyridine

A 1 L 2-necked flask was charged with 100 mL of a 2 N solution of lithium diisopropylamide and 400 mL of tetrahydrofuran. This was cooled to $-72°$ C. and 2-fluoropyridine (19.42 g, 200 mmol) dissolved in 100 mL of tetrahydrofuran was added dropwise. This was stirred at $-70°$ C. for 4 h before dropwise addition of 51 g (200 mmol) of iodine dissolved in 150 mL of tetrahydrofuran. This was stirred for 1 h before being quenched with water. The mixture was diluted with ethyl acetate and aqueous sodium bisulfite. The organic layer was evaporated in vacuo and the product was distilled on a Kugelrohr yielding 2-fluoro-3-iodopyridine (27.0 g, 60.6% yield).

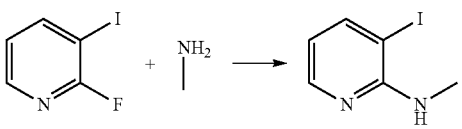

Synthesis of 3-iodo-N-methylpyridin-2-amine

A 1 L round bottom flask was charged with 2-fluoro-3-iodopyridine (27.0 g, 121 mmol) and 500 mL of 40% aqueous solution of methylamine. This was stirred at reflux for 4 h before being cooled to ambient temperature. The product was extracted with dichloromethane. Evaporation of the dichloromethane gave 3-iodo-N-methylpyridin-2-amine (26.8 g, 95% yield).

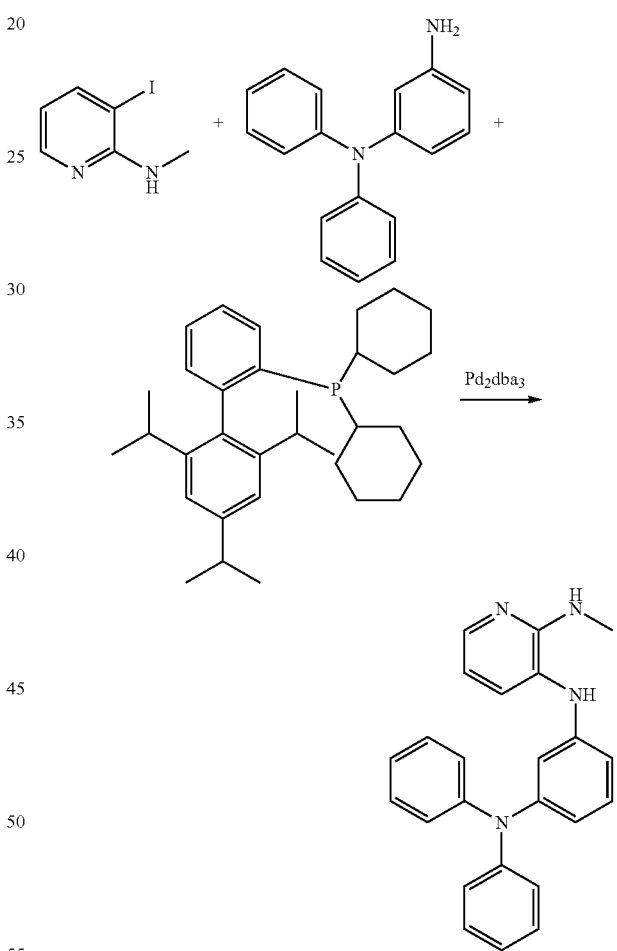

Synthesis of $N^3$-(3-(diphenylamino)phenyl)-$N^2$-methylpyridine-2,3-diamine

A 1 L round-bottomed flask was charged with 3-iodo-N-methylpyridin-2-amine (8.95 g, 38.3 mmol), $N^1,N^1$-diphenylbenzene-1,3-diamine (9.96 g, 38.3 mmol), dicyclohexyl (2',4',6'-triisopropyl-[1,1'-biphenyl]-2-yl)phosphine (0.183 g, 0.384 mmol) and sodium 2-methylpropan-2-olate (5.15 g, 53.6 mmol) in toluene (500 mL). Nitrogen was bubbled through for 10 minutes. Then $Pd_2\,dba_3$ (88 mg, 0.10 mmol)

was added and this was stirred at 120° C. for overnight. The mixture was then filtered and the filtrate was concentrated and chromatographed using a mobile phase gradient of 0-20% ethyl acetate in dichloromethane to give $N^3$-(3-(diphenylamino)phenyl)-$N^2$-methylpyridine-2,3-diamine (12.2 g, 91% yield).

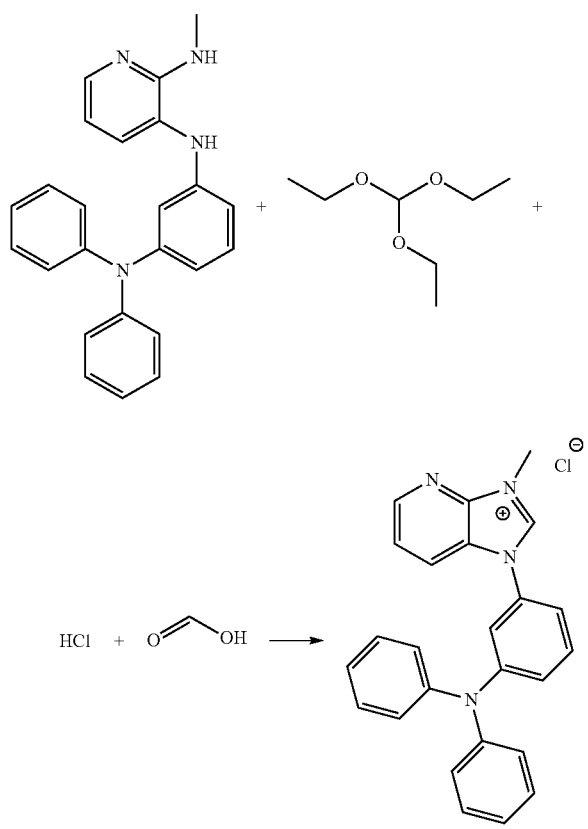

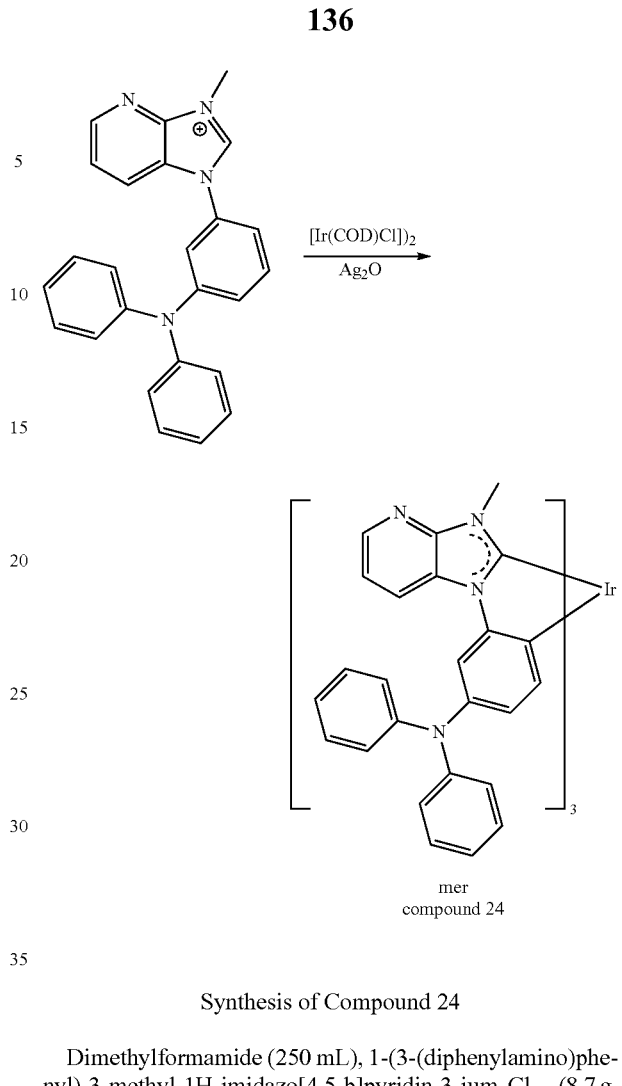

mer
compound 24

Synthesis of 1-(3-(diphenylamino)phenyl)-3-methyl-1H-imidazo[4,5-b]pyridin-3-ium chloride A 500 mL round bottom flask was charged with $N^3$-(3-(diphenylamino)phenyl)-$N^2$-methylpyridine-2,3-diamine (12.1 g, 33.0 mmol), triethoxymethane (150 mL), conc. HCL (3 mL, 12N) and formic acid (0.10 mL). This was stirred at reflux overnight. The mixture was then cooled to ambient temperature and the product was filtered and washed with hexane to give 1-(3-(diphenylamino)phenyl)-3-methyl-1H-imidazo[4,5-b]pyridin-3-ium chloride as a white powder (9.3 g, 68%).

Synthesis of Compound 24

Dimethylformamide (250 mL), 1-(3-(diphenylamino)phenyl)-3-methyl-1H-imidazo[4,5-b]pyridin-3-ium, Cl— (8.7 g, 21.1 mmol), Silver (I) oxide (5.10 g, 22.0 mmol) and the iridium dimer (2.02 g, 3.0 mmol) were placed into a 500 mL 2-necked round bottom flask. This was stirred at an internal temperature of 145° C. for 20 h. The mixture was then filtered through Celite® and the cake was washed with dichloromethane. The filtrate was concentrated in vacuo and the crude product was purified on a silica gel column eluted with a gradient of 0-3% ethyl acetate in dichloromethane giving Compound 24 (1.40 g, 17.5% yield) as a yellow solid.

Example 15

Synthesis of Compound 25

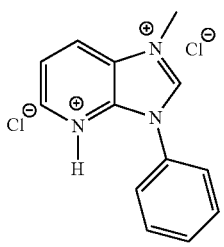

+

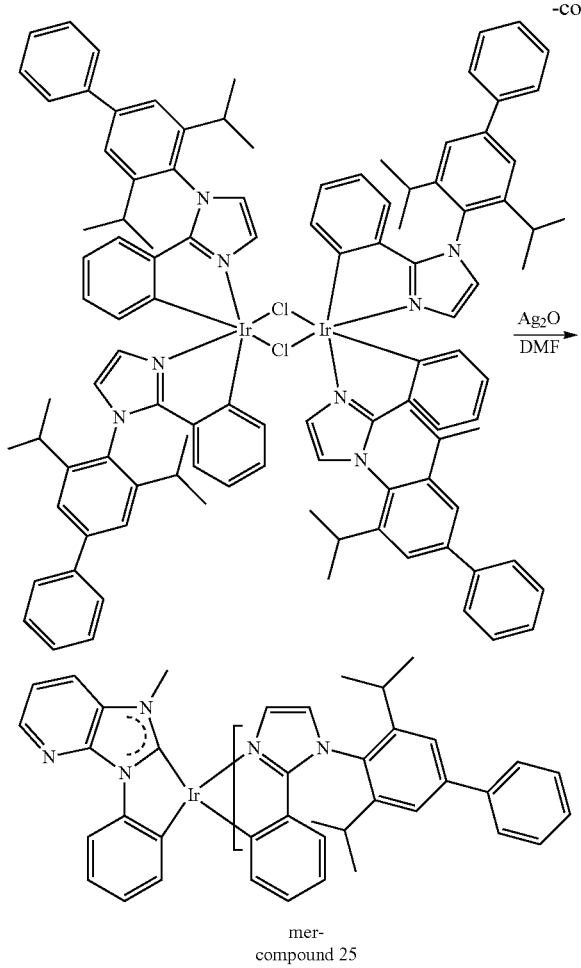

mer-
compound 25

Synthesis of Compound 25

Carbene ligand precursor (1 g, 3.56 mmol), iridium chlorobridged dimer (0.877 g, 0.445 mmol) and silver oxide (0.824 g, 3.56 mmol) were mixed in DMF (50 mL) and refluxed for 4 h. The mixture was cooled to room temperature and monitored by TLC. The reaction was stopped and filtered through a Celite® plug. Dichloromethane was added and mixture was washed with LiCl solution three times and dried over $MgSO_4$. The solvent was evaporated. The residue was purified by a triethylamine treated column using 1:2 dichloromethane/hexanes as solvent to give Compound 25 (0.75 g, 73% yield).

Example 16

Synthesis of Compound 26

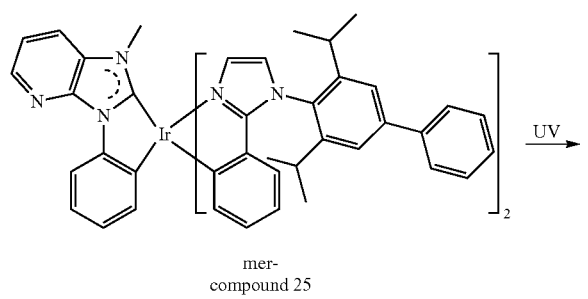

mer-
compound 25

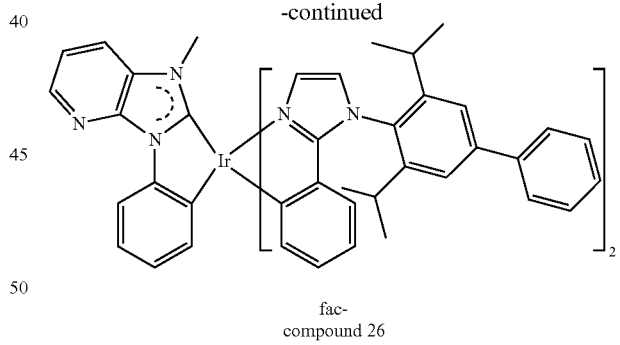

fac-
compound 26

Synthesis of Compound 26

Compound 25 (1.3 g, 1.1 mmol) was dissolved in DMSO (80 mL) and degassed with nitrogen. The compound was isomerized under UV irradiation. The reaction was monitored by NMR. After the reaction was complete, the reaction mixture was poured into water. The precipitate was collected by filtration. The solid was further purified by a short column to give Compound 26 (1.0 g, 77% yield).

Example 17

Synthesis of Compound 28

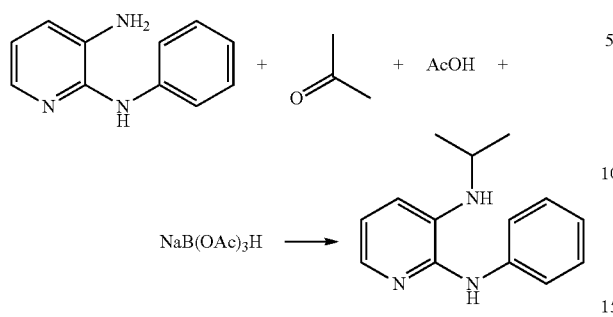

Synthesis of N³-isopropyl-N²-phenylpyridine-2,3-diamine

N²-phenylpyridine-2,3-diamine (14.1 g, 76 mmol) and acetone (8.39 mL, 114 mmol) was added to a solution of acetic acid and dichloromethane. Sodium triacetoxyborohydride (22.59 g, 107 mmol) was added to the reaction mixture and stirred overnight at room temperature. Reaction mixture was quenched with 1N HCl. Organic layer was extracted with ethyl acetate. Ethyl acetate solution was washed with 1N sodium hydroxide solution followed by brine and dried over anhd. MgSO₄. N³-isopropyl-N²-phenylpyridine-2,3-diamine (16.3 g, 94% yield) was isolated from crude by column chromatography using hexanes and ethyl acetate as eluent.

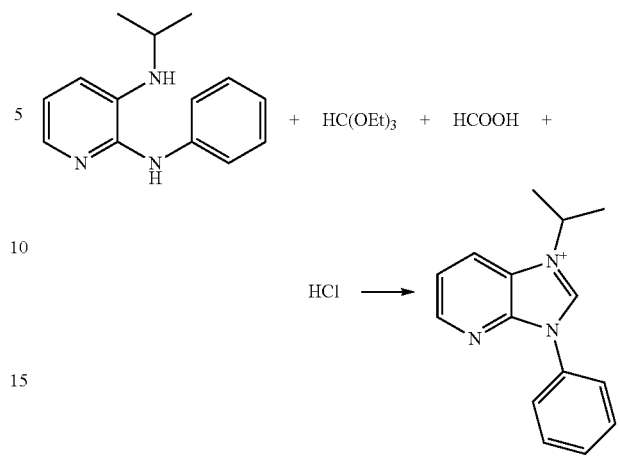

Synthesis of 1-isopropyl-3-phenyl-3H-imidazo[4,5-b]pyridin-1-ium chloride

N³-isopropyl-N²-phenylpyridine-2,3-diamine (10 g, 44.0 mmol), triethoxymethane (293 mL, 1760 mmol), formic acid (0.017 mL, 0.440 mmol) and hydrogen chloride (4.24 mL, 44.0 mmol) were mixed together and heated to reflux overnight. The reaction mixture was cooled to room temperature and the precipitate was filtered off. The solid product was collected and washed with hexanes. 1-isopropyl-3-phenyl-3H-imidazo[4,5-b]pyridin-1-ium chloride (8.1 g, 67% yield) was isolated as white crystalline solid after recrystallization from boiling ethanol.

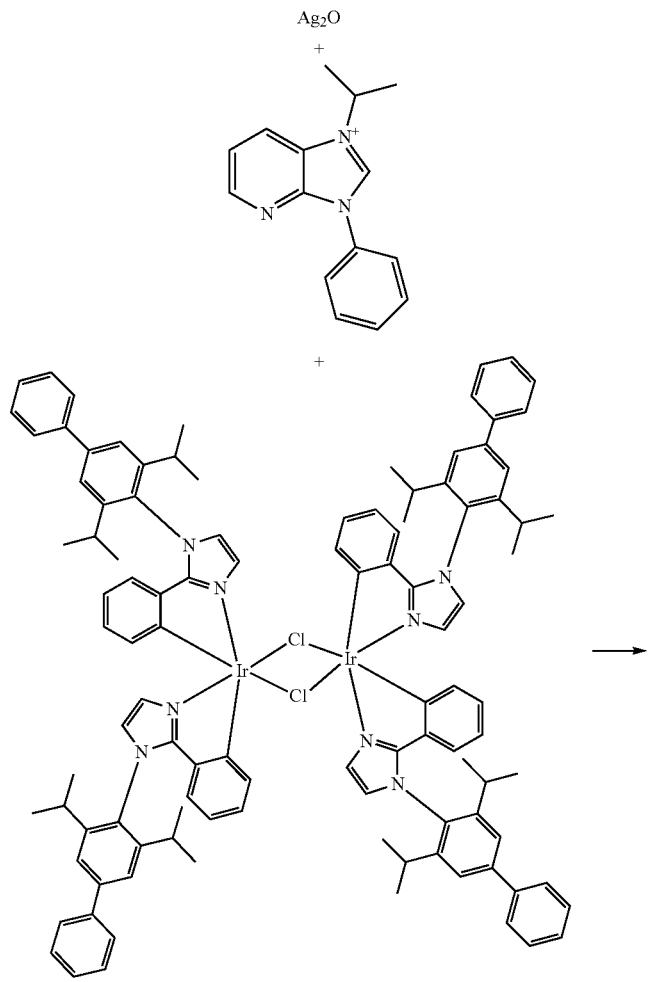

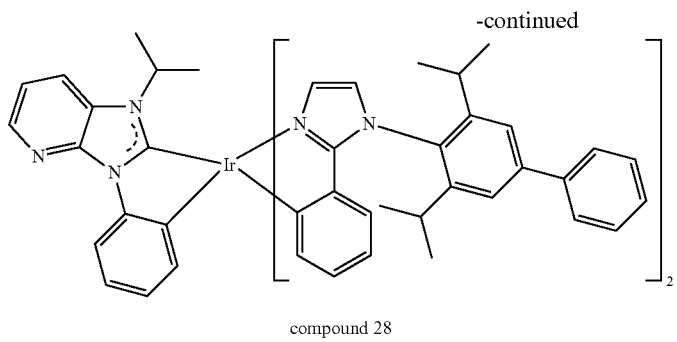

compound 28

Synthesis of Compound 28

Iridium chloro-bridged dimer (2 g, 1.013 mmol), silver(I) oxide (0.939 g, 4.05 mmol) and 1-isopropyl-3-phenyl-3H-imidazo[4,5-b]pyridin-1-ium chloride (1.11 g, 4.05 mmol) were added to 100 mL DMF and degassed for 30 minutes by bubbling nitrogen gas. The reaction mixture was heated to 50° C. for 1 h. Crude reaction mixture was poured into 200 mL 3:1 mixture of hexanes and ether. Precipitate thus obtained was filtered through a Celite® pad. Organic solvent was removed under reduced pressure to give a light yellow color crude product. Crude mixture of compounds was photoisomerized in 100 mL DMSO. The DMSO solution was poured over 400 mL ice water and solids were collected by filtration. Compound 28 (0.15 g, 7% yield) thus obtained was further purified by sublimation under high vacuum.

Example 18

Synthesis of Compound 29 and Compound 30

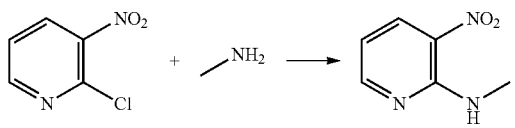

Synthesis of N-methyl-3-nitropyridin-2-amine

Methylamine (33% in EtOH) (110 mL, 883 mmol) was placed in a 500 mL three necked round bottom flask. It was cooled to 0° C. using ice bath. 2-chloro-3-nitropyridine (20 g, 126 mmol) was added to the above solution in portions as this is an exothermic reaction. After the addition was complete the reaction mixture was stirred for 2 h at 0° C. and later 1 h at room temperature. Solvent was concentrated and residue was taken in 500 mL of water and extracted with EtOAc 3×150 mL. Combine organic layer was dried over $Na_2SO_4$, filtered and concentrated to give a bright orangish yellow solid (19 g, 98.5%).

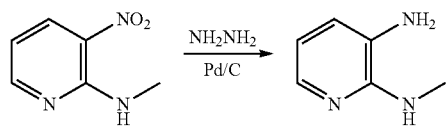

Synthesis of $N^2$-methylpyridine-2,3-diamine

Palladium (0.924 g, 0.868 mmol) was added to a three necked 1 L round bottom flask equipped with a condenser and flow of $N_2$, and it was wet by adding a few mL of water. Then, N-methyl-3-nitropyridin-2-amine (19.0 g, 124 mmol) dissolved in ethanol (130 mL) was added. Hydrazine (15.41 ml, 496 mmol) was added to the above solution dropwise over a period of 20 minutes with continuous stirring. The reaction was exothermic, and $H_2$ gas evolved during the reaction. The reaction mixture was stirred at room temperature for about 2 h. The color of the reaction changed from yellow to colorless. Completion of the reaction was checked by TLC. Pd was filtered on a tightly packed Celite® plug. The Celite® was first washed with DCM, and Pd was filtered off. A little bit of Celite® was placed on the top of Pd for safety, and it was washed with DCM until all the product was washed off of the Celite®. Combined solvent was concentrated and residue was taken in EtOAc washed with $H_2O$. NaCl solid was added to remove any left over hydrazine. EtOAc was dried on $Na_2SO_4$, filtered and concentrated to give a dark brown solid (11.95 g; 78.25%).

Synthesis of $N^2$-methyl-$N^3$-phenylpyridine-2,3-diamine $N^2$-methylpyridine-2,3-diamine (11.95 g, 97 mmol), iodobenzene (16.22 ml, 146 mmol), sodium 2-methylpropan-2-olate (13.99 g, 146 mmol), 8,8'-bis(diphenylphosphino)-1,1'- binaphthalene (BINAP) (60.4 g, 97 mmol) with toluene (400 mL) were added to a three necked 1 L round bottom flask. The reaction was degassed with $N_2$ for 20 minutes. $Pd_2(dba)_3$ (1.777 g, 1.941 mmol) was added and the reaction mixture was refluxed for 20 h. The reaction mixture was concentrated to dryness. Residue was dissolved in EtOAc. It was not clear solution, but a suspension was obtained and then filtered through a silica gel plug. The desired product was concentrated and recrystallized from DCM/hexanes providing a yield of 6.45 g, 33.3%.

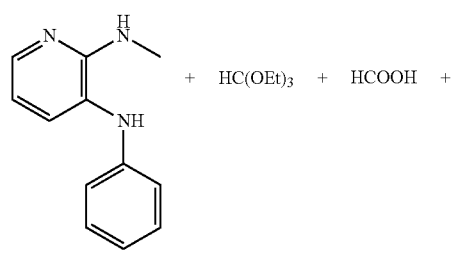

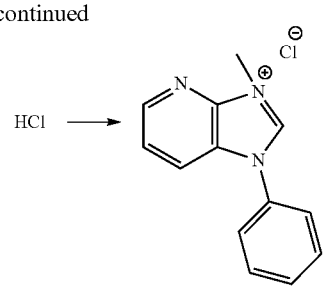

Synthesis of Carbene Precursor $N^2$-methyl-$N^3$-phenylpyridine-2,3-diamine (6.45 g, 32.4 mmol) and triethoxymethane (269 mL, 1619 mmol) were added to a 500 mL three necked round bottom flask, followed by the addition of hydrogen chloride (4.6 mL, 32.4 mmol) and formic acid (3.1 mL, 32.4 mmol) under $N_2$ at room temperature. The reaction was heated to 80° C. overnight and stirred under nitrogen. After 18 h, a blue solution with a solid was obtained. The reaction was cooled to room temperature, and filtered. The solid was washed with EtOAc and hexanes, then it was dried to afford a light blue fluffy solid (4.3 g, 54%).

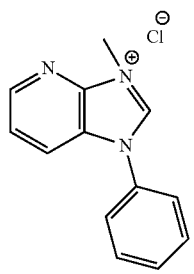

+

$Ag_2O$

+

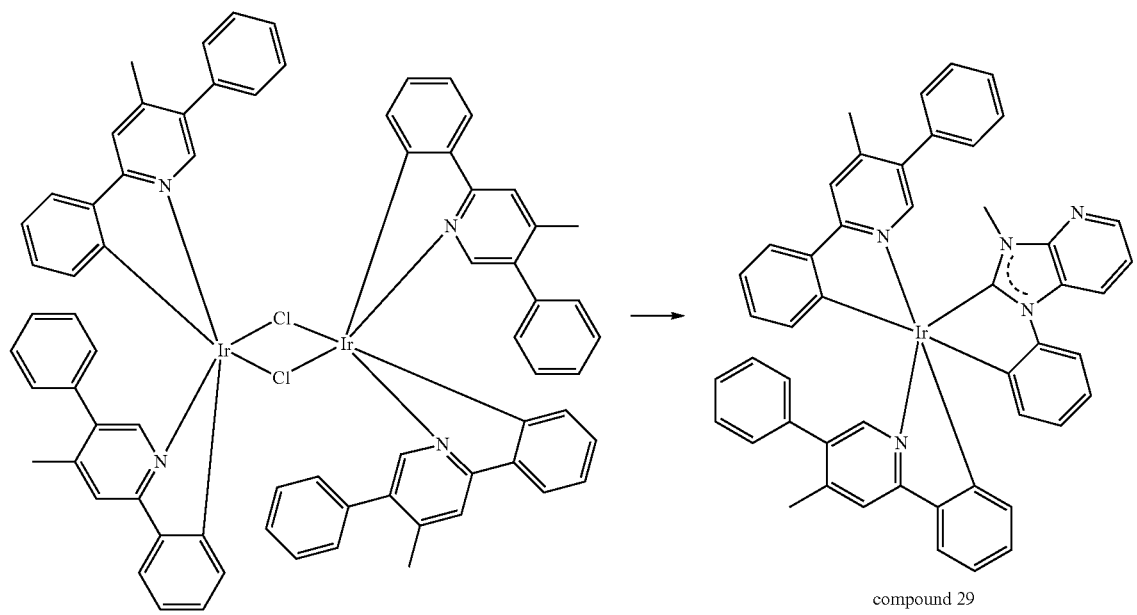

compound 29

Synthesis of Compound 29

The carbene precursor (2.3 g, 9.36 mmol) and silver oxide (2.71 g, 11.70 mmol) with toluene (Volume: 100 ml) were added to a 250 mL round bottom flask. The reaction mixture was stirred for 10 minutes at room temperature, followed by the addition of iridium dimer (2.3 g, 1.605 mmol). The reaction mixture was refluxed for 1 h, and then it was cooled to room temperature. The reaction mixture was concentrated by removing toluene upon rotoevaporation. The dark residue obtained was dissolved in dichloromethane. Ag$_2$O was removed by passing it through a tightly packed Celite® plug. The Celite® plug was washed with dichloromethane. The compound in DCM solution was passed through a pretreated silica gel plug with 20% triethyl amine and hexane. The filtered dichloromethane solution was concentrated to one fourth of its volume. 2-Isopropyl alcohol was added and concentrated on rotoevaporation. The product crashed out as a yellow precipitate in the solvent. The yellow precipitate was filtered and washed with MeOH, followed by hexane, to give 2.35 g of the desired product as mer isomer (57.3% yield). The isomer was photoisomerized in CH$_3$CN under UV irradiation. The crude compound was purified by column to afford 0.67 g of Compound 29.

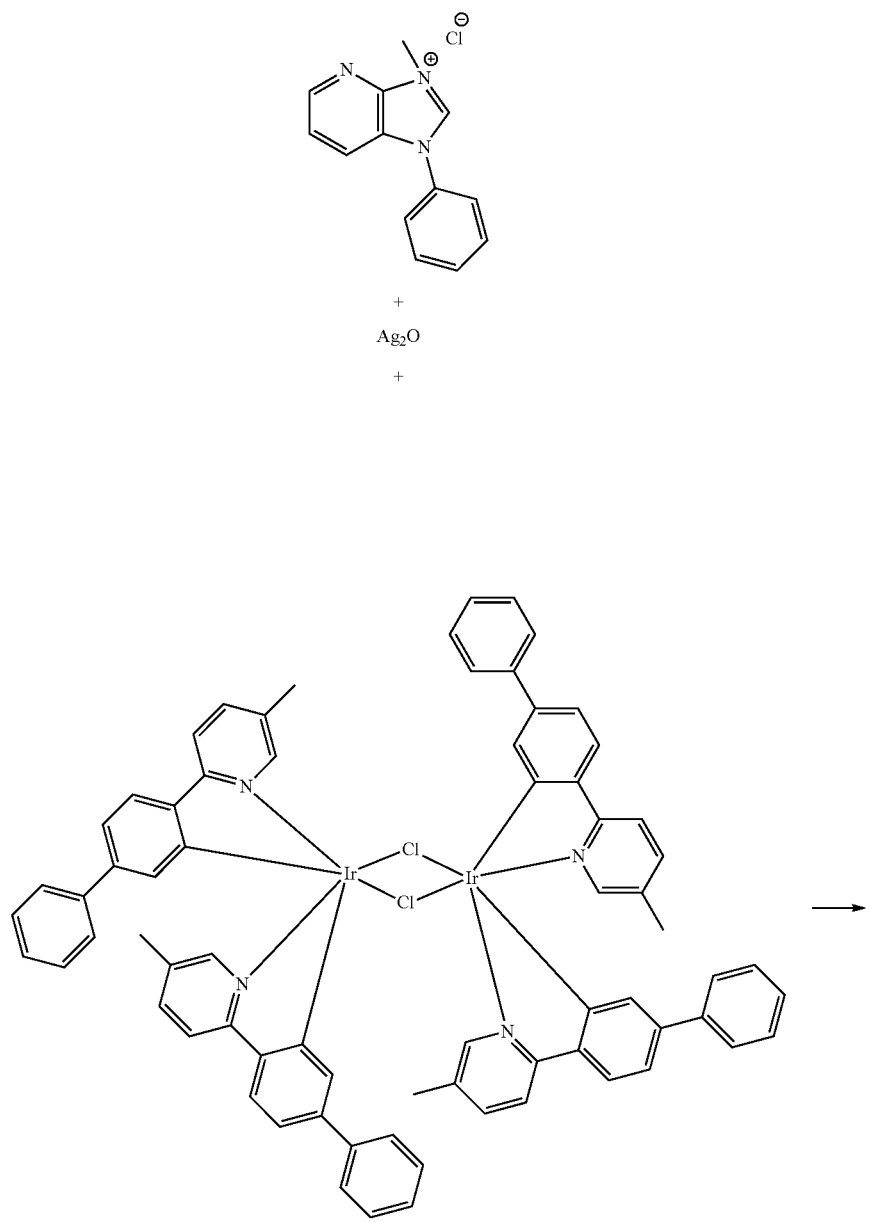

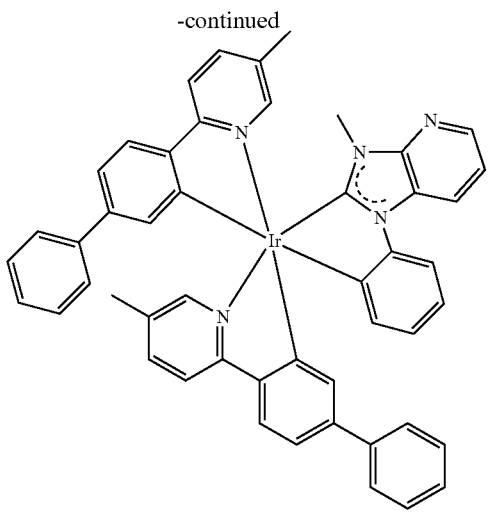

compound 30

Synthesis of Compound 30

A 250 mL round bottom flask was charged with carbene precursor (1.58 g, 6.43 mmol) and silver oxide (1.863 g, 8.04 mmol) with toluene (100 mL). The reaction mixture was stirred for few minutes, followed by the addition of dimer (1.58 g, 1.103 mmol). The reaction mixture was refluxed for 1 h. After 1 h, the reaction mixture was cooled to room temperature. Toluene was removed upon rotoevaporation. The dark residue obtained was dissolved in dichloromethane. $Ag_2O$ was removed by passing it through a tightly packed Celite® plug. The Celite® plug was washed with dichloromethane. The DCM solution was passed through a silica gel plug pretreated with 20% triethyl amine/hexane and eluted with DCM. This was concentrated to dryness. Residue was dissolved in DCM and IPA was added and concentrated. The yellow precipitate was filtered and washed with MeOH followed by hexane to give 1.2 g of the desired compound as mer isomer. The mer isomer was isomerized under UV irradiation to give 0.9 g of Compound 30 as fac isomer.

Example 19

Synthesis of Compound 31

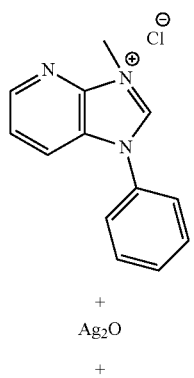

+

$Ag_2O$

+

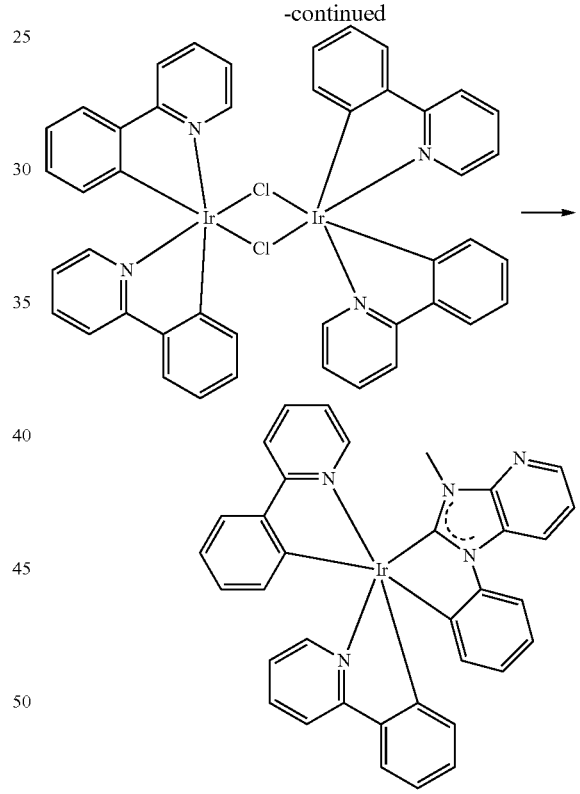

Synthesis of Mer Isomer

Carbene precursor (1.0 g, 4.07 mmol) and silver oxide (1.179 g, 5.09 mmol) were suspended in toluene, stirred for 10 minutes and IrPPy dimer (0.742 g, 0.692 mmol) was added as one portion. The reaction mixture was then heated to reflux for 1 h, cooled to room temperature and the toluene was evaporated. The residue was purified by column chromatography on silica gel (treated with $Et_3N$, hexane/DCM 1/1 eluent). Evaporation of pure fractions provided target complex (0.98 g) as yellow solid.

Synthesis of Compound 31
The mer complex (0.720 g, 1.014 mmol) was dissolved in 300 mL of acetonitrile at room temperature and subjected to photolysis for 2 h. Evaporation, followed by crystalliziation from DCM/MeCN, provided 0.65 g of fac-isomer (Compound 31) as yellow solid.
Example 20
Synthesis of Compound 32
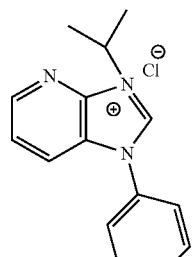
+
Ag$_2$O
+
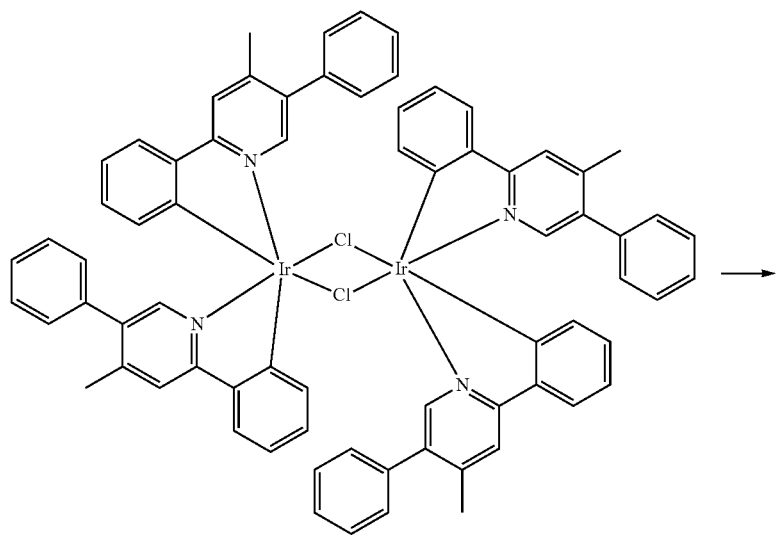
→
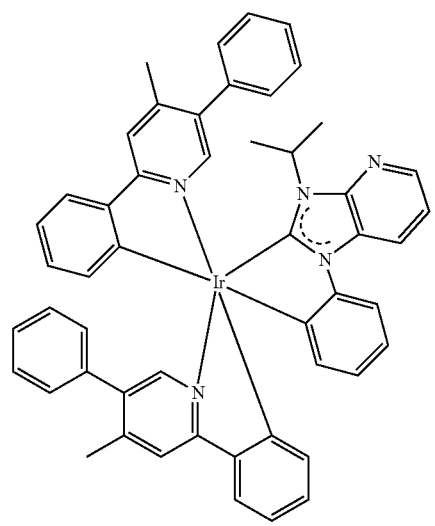

Synthesis of Mer Isomer

3-Chloro-3-isopropyl-1-phenyl-2,3-dihydro-1H-imidazo[4,5-b]pyridin-3-ium-2-ide (2.0 g, 7.31 mmol) and silver oxide (2.116 g, 9.13 mmol) were suspended in 200 mL of toluene, stirred for 30 minutes. Then, the dimer complex (1.779 g, 1.242 mmol) was added, and it was refluxed under nitrogen for 1 h. It was filtered through a short silica plug, and concentrated to ¼ of the volume. 75 mL of i-PrOH was added and a yellow solid was filtered (2.0 g, 88%).

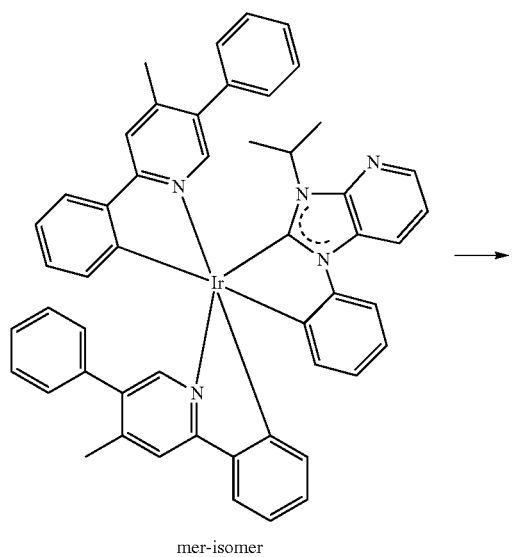

mer-isomer

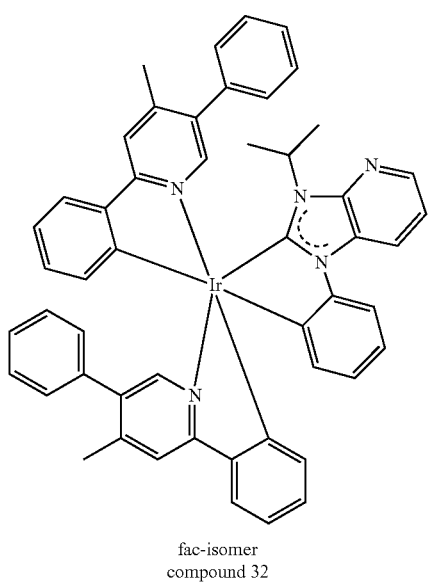

fac-isomer
compound 32

Synthesis of Compound 32

The solution of 2.0 g of mer isomer in 200 mL of DMSO was subjected to photolysis at 40-45° C. (Rayonet, 3 h). The reaction was monitored by HPLC. After completion the reaction mixture was diluted with 200 mL of water, and the yellow solid was separated by filtration. It was purified by column chromatography on silica, and then eluted with hexane/DCM 3/7 mixture. Pure fractions were concentrated and the yellow solid was filtered. Sublimation at 295° C./$10^{-5}$ provided 1.8 g (90%) of pure Compound 32.

Device Examples

All device examples were fabricated by high vacuum ($<10^{-7}$ Torr) thermal evaporation. The anode electrode is 1200 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package.

The organic stack of the Devices consisted of sequentially, from the ITO surface, 100 Å of hole injection layer (HIL), 300 Å of 4,4'-bis[N-(1-naphthyl)-N-phenylamino]biphenyl (α-NPD) as the hole transporting later (HTL), 300 Å of a host-dopant mixture as the emissive layer (EML), 50 Å or 100 Å of blocking layer (BL), and 400 Å of electron transporting layer (ETL).

Comparative Device Examples were fabricated similarly to Device Examples, except that Compounds A or H were used as the emitter.

As used herein, the following compounds have the following structures:

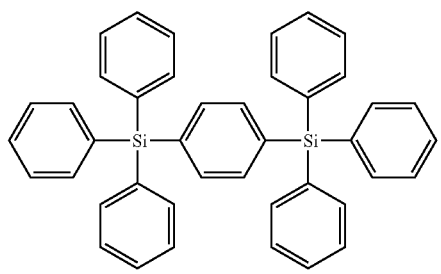 [SMILES: c1ccc([Si](c2ccccc2)(c2ccccc2)c2ccc([Si](c3ccccc3)(c3ccccc3)c3ccccc3)cc2)cc1]
UGH2
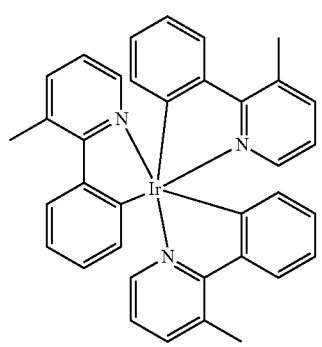
Compound C
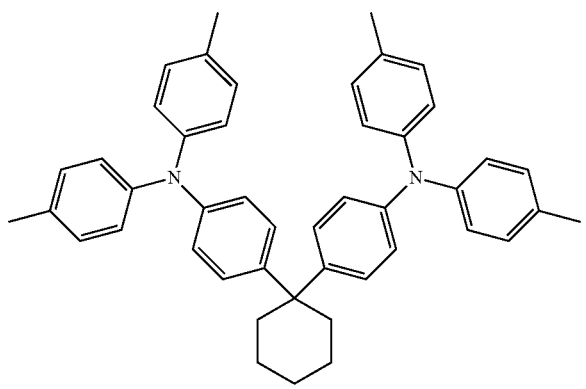
TAPC
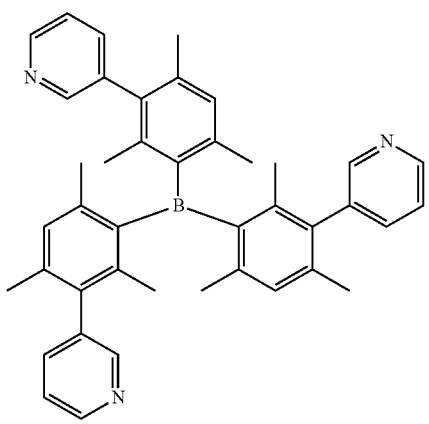 [SMILES: Cc1cc(C)c(-c2cccnc2)c(C)c1B(c1c(C)cc(C)c(-c2cccnc2)c1C)c1c(C)cc(C)c(-c2cccnc2)c1C]
3TPYMB

TPBi
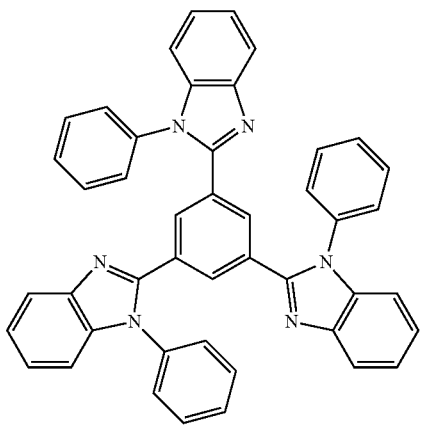 [SMILES: c1ccc(-n2c(-c3cc(-c4nc5ccccc5n4-c4ccccc4)cc(-c4nc5ccccc5n4-c4ccccc4)c3)nc3ccccc32)cc1]
TCTA
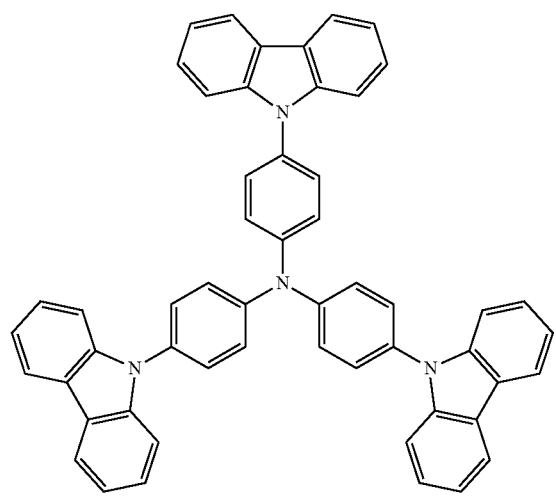 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1]
UGH3
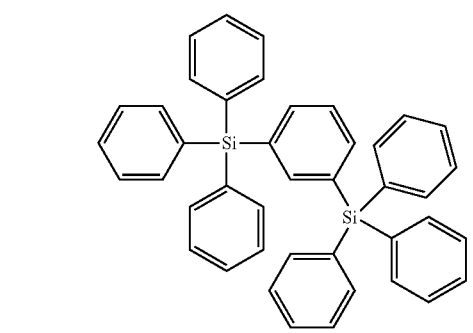 [SMILES: c1ccc([Si](c2ccccc2)(c2ccccc2)c2cccc([Si](c3ccccc3)(c3ccccc3)c3ccccc3)c2)cc1]
Compound D
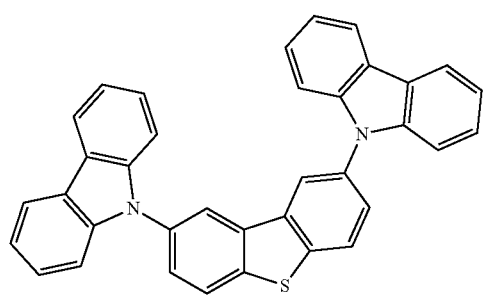 [SMILES: c1ccc2c(c1)c1ccccc1n2-c1ccc2sc3ccc(-n4c5ccccc5c5ccccc54)cc3c2c1]

-continued
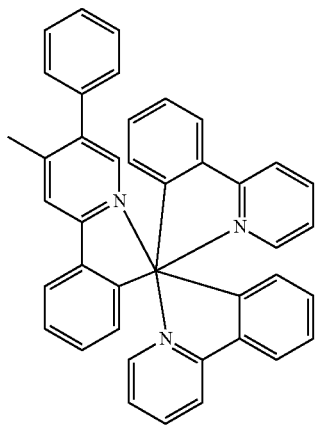
Compound E
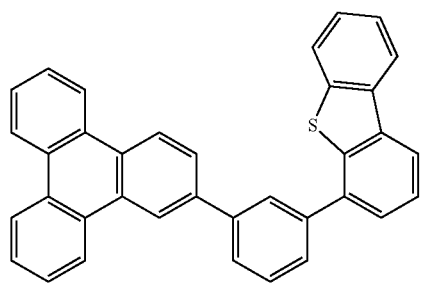 [SMILES: c1cc(-c2ccc3c4ccccc4c4ccccc4c3c2)cc(-c2cccc3c2sc2ccccc23)c1]
Compound F
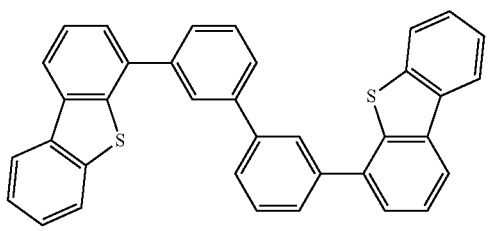 [SMILES: c1cc(-c2cccc(-c3cccc4c3sc3ccccc34)c2)cc(-c2cccc3c2sc2ccccc23)c1]
Compound G
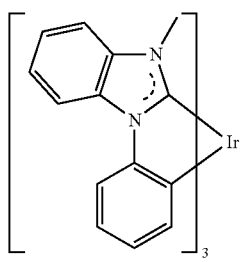
-fac
Compound A
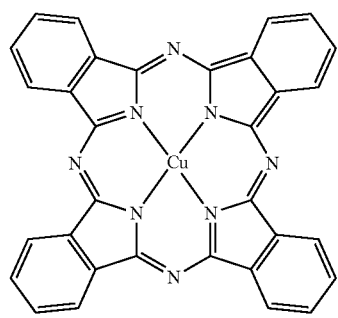
CuPc

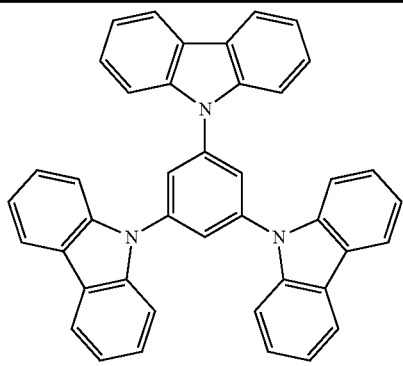

tCP

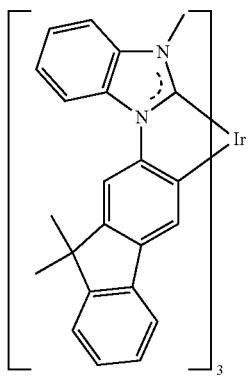

Compound H mer

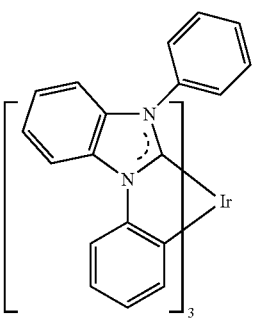

Compound B

-fac

Device examples are detailed in Table 3 with doping percentages (%) and thickness (Å) noted in parenthesis. Ex. is an abbreviate for Example. Cmpd. is an abbreviation for Compound. Comp. is an abbreviation for Comparative. The corresponding device data is summarized in Table 4.

TABLE 3

| Device Ex. | Device Structure |
|---|---|
| Ex. 1 | Cmpd. C(100 Å)/NPD(300 Å)/TCTA(50 Å)/UGH2: Cmpd. 8(15%, 300 Å)/TPBi: AlQ(400 Å) |
| Ex. 2 | LG101(100 Å)/TAPC(300 Å)/UGH3: Cmpd. 21(10%, 300 Å)/Cmpd. D(50 Å)/3TPYMB(400 Å) |
| Ex. 3 | LG101(100 Å)/NPD(300 Å)/UGH2: Cmpd. 10(15%, 300 Å)/Cmpd. D(50 Å)/LG201(400 Å) |
| Ex. 4 | Cmpd. C(100 Å)/NPD(300 Å)/UGH3: Cmpd. 19(10%, 300 Å)/Cmpd. D(50 Å/AlQ(400 Å) |
| Ex. 5 | Cmpd. C(100 Å)/NPD(300 Å)/Cmpd. D: Cmpd. 25(15%, 300 Å/Cmpd. D(50 Å)/AlQ(400 Å) |
| Ex. 6 | Cmpd. C(100 Å)/NPD(300 Å)/Cmpd. D: Cmpd. 26(15%, 300 Å)/Cmpd. D(50 Å)/AlQ(400 Å) |
| Ex. 7 | Cmpd. C(100 Å)/NPD(300 Å)/Cmpd. D: Cmpd. 28(15%, 300 Å)/Cmpd.d D(50 Å)/AlQ(400 Å) |
| Ex. 8 | Cmpd. E(100 Å)/NPD(300 Å)/Cmpd. F: Cmpd. 5(10%, 300 Å)/Cmpd. F(100 Å)/AlQ(400 Å) |
| Ex. 9 | Cmpd. E(100 Å)/NPD(300 Å)/Cmpd. F: Cmpd. 29(7%, 300 Å)/Cmpd. F(100 Å)/AlQ(400 Å) |
| Ex. 10 | Cmpd. E(100 Å)/NPD(300 Å)/Cmpd. F: Cmpd. 30(10%, 300 Å)/Cmpd. F(100 Å)/AlQ(400 Å) |

TABLE 3-continued

| Device Ex. | Device Structure |
|---|---|
| Ex. 11 | Cmpd. E(100 Å)/NPD(300 Å)/Cmpd. F: Cmpd. 3(10%, 300 Å)/Cmpd. F(100 Å)/AlQ(400 Å) |
| Ex. 12 | Cmpd. E(100 Å)/NPD(300 Å)/Cmpd. F: Cmpd.d 4(10%, 300 Å)/Cmpd. F(100 Å)/AlQ(400 Å) |
| Ex. 13 | Cmpd. C(100 Å)/NPD(300 Å)/Cmpd. G: Cmpd. 31(9%, 300 Å)/Cmpd. F(100 Å)/AlQ(400 Å) |
| Ex. 14 | Cmpd. E(100 Å)/NPD(300 Å)/Cmpd. F: Cmpd. 32(10%, 300 Å)/Cmpd. F(100 Å)/AlQ(400 Å) |
| Comp. Ex. 1 | CuPc(100 Å)/NPD(300 Å)/UGH3: Cmpd A(6%, 300 Å/BAlQ(400 Å) |
| Comp. Ex. 2 | CuPc(100 Å)/NPD(300 Å)/tCP: Cmpd H(6%, 300 Å/BAlQ(400 Å) |

TABLE 4

| | | | | At 1000 nits | | | |
|---|---|---|---|---|---|---|---|
| | 1931 CIE | | | FWHM | V | LE | EQE | PE |
| Ex. | x | y | $\lambda_{max}$ | (nm) | (V) | (Cd/A) | (%) | (lm/W) |
| Ex. 1 | 0.156 | 0.155 | 456 | 74 | 12.1 | 5 | 4.1 | 1.3 |
| Ex. 2 | 0.162 | 0.060 | 430 | 56 | 10 | 4.1 | 8.2 | 1.3 |
| Ex. 3 | 0.157 | 0.163 | 458 | 71 | 11.3 | 2.2 | 1.7 | 0.6 |
| Ex. 4 | 0.164 | 0.080 | 436 | 63 | 12.8 | 2.7 | 3.8 | 0.7 |
| Ex. 5 | 0.190 | 0.345 | 490 | 78 | 9 | 8.7 | 4 | 3 |
| Ex. 6 | 0.175 | 0.288 | 486 | 74 | 7.9 | 10.1 | 5.2 | 4.0 |
| Ex. 7 | 0.170 | 0.287 | 486 | 70 | 7.2 | 14.5 | 7.6 | 6.3 |
| Ex. 8 | 0.408 | 0.541 | 552 | 108 | 9.8 | 13 | 4.2 | 4.2 |
| Ex. 9 | 0.382 | 0.572 | 548 | 96 | 8.7 | 24.6 | 7.4 | 8.9 |
| Ex. 10 | 0.383 | 0.588 | 524 | 72 | 6.8 | 48.1 | 13.7 | 22.1 |
| Ex. 11 | 0.311 | 0.546 | 520 | 98 | 10.2 | 3.7 | 1.2 | 1.1 |
| Ex. 12 | 0.414 | 0.552 | 552 | 98 | 7.3 | 37.3 | 11.6 | 16.1 |
| Ex. 13 | 0.227 | 0.549 | 494 | 68 | 7.3 | 22.4 | 7.8 | 9.7 |
| Ex. 14 | 0.324 | 0.600 | 538 | 86 | 6.5 | 38.2 | 11.2 | 3.4 |
| Comp. Ex. 1 | 0.153 | 0.091 | 428 | 80 | 20.8 | 1.17 | 1.89 | 0.17 |
| Comp. Ex. 2 | 0.174 | 0.393 | 501 | 73 | 15 | 4.68 | 2 | 0.98 |

Examples 1-4 demonstrate deep blue emission of the parent pyridyl carbene structures. Example 2, in particular demonstrates high efficiency of 8.2% at a brightness of 1000 nits and very good deep blue color (CIE 0.162, 0.060) with a peak emission wavelength of 430 nm. The emission from these devices is Gaussian, due to the strong MLCT character of the pyridine containing dopants, whereas comparative example 2 has vibronic structured emission intrinsic to compound A. Device examples 1-4 are red-shifted from the comparative example resulting in a more useful color in the visible wavelengths. An example of redshifting comparative compound A by extending the conjugation is shown in comparative example 2. This device is measured to have an electroluminescent transient of 53 μs, due to enhanced ligand centered emission character. This results in low device efficiency. Nitrogen containing carbenes can be used to red shift the emission without losing the desirable MLCT emission. Substitution of electron donating groups, as shown for compounds 20, 22, 23, 24 can further red shift the emission into the desirable range without losing strong MLCT properties.

Examples 5-7 demonstrate pyridyl carbene ligands used on heteroleptic dopants with phenyl imidazole ligands. These materials have an approximate 10 nm blue-shift from the highest energy peak compared to tris phenyl imidazole analogues due to the effect of the carbene ligand. In devices these materials give modest efficiency with quantum efficiency in the range of 4-8% and blue CIE. It is found that N-isopropyl substitution in Compound 28 (Example 7) improves the sublimation making it a better material for vacuum deposition. This may explain the improved performance with respect to device efficiency shown for Example 7 compared to Example 6.

Examples 9, 10, 13 and 14 demonstrate pyridyl carbene ligands used on heteroleptic dopants in combination with phenyl pyridine ligands. The carbene ligand can be used to tune the emission properties compared to the tris phenyl pyridine analogues. For example, Example 13 shows a peak emission at 494 nm compared to 510 nm for tris Ir(ppy)$_3$. Examples 8, 11, and 12 demonstrate devices with pyrazine containing compounds, i.e., 2 nitrogen atoms. These materials are significantly red-shifted, compared to the pyridyl containing compounds in Examples 1-4, to the more desirable color region with broad Gaussian emission. This broad emission may be useful for white lighting. It is seen that mer isomers in Examples 8 and 12 have higher efficiency as they are red-shifted compared to the analogous fac isomer. The fac isomer in Example 11 is likely quenched due to the triplet energy of compound F resulting in low device efficiency. The N-isopropyl group is again found to improve sublimation which may explain the improved device efficiency compared to Example 8 (N-methyl).

Examples 1-4 demonstrate deep blue emitters in a wide bandgap host. The nitrogen containing rings show a useful red-shifting effect compared to the non-nitrogen containing comparative example, which emits in the UV part of the spectrum.

Examples 8, 11 and 12 demonstrate that devices comprising two nitrogen-containing emitters can have further red-shifted emission into a desired emission range. These materials may be promising as broadband emitters.

Further examples demonstrate that these nitrogen containing N-heterocyclic carbene ligands can be used in red and green heteroleptic complexes. These ligands can be successfully used to tune the color of emission to the desired range.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound selected from the group consisting of:

Compound 1
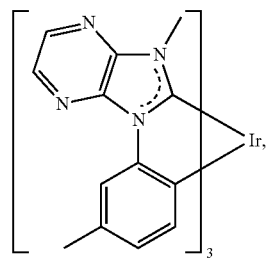
-fac

Compound 2
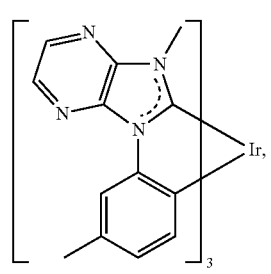
-mer

Compound 3
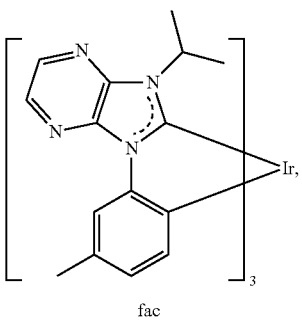
fac

Compound 4
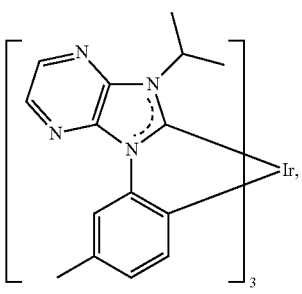
mer

Compound 5
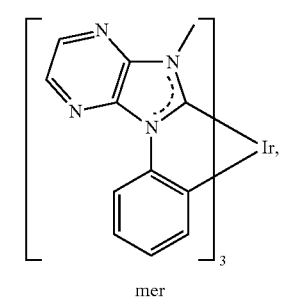
mer

Compound 6
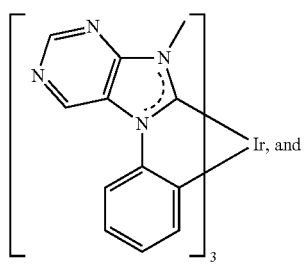
Ir, and

Compound 7
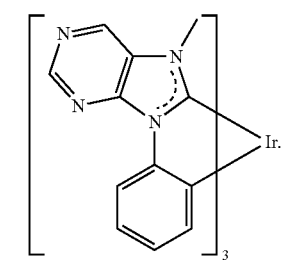
Ir.

2. A first device comprising an organic light emitting device, comprising:
 an anode;
 a cathode; and
 an organic layer, disposed between the anode and the cathode, wherein the organic layer comprises a compound selected from the group consisting of:

Compound 1
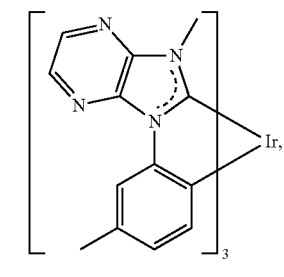
-fac

Compound 2
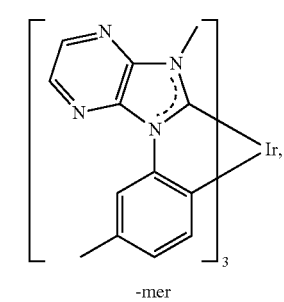
-mer

Compound 3

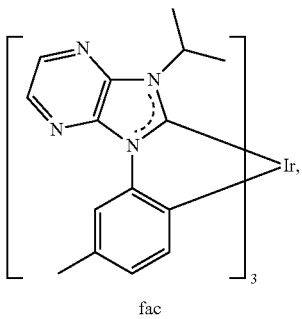

fac

Compound 4

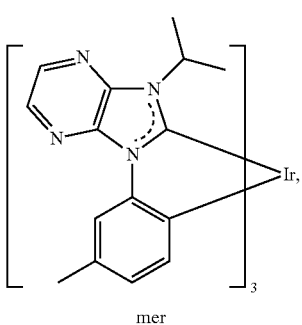

mer

Compound 5

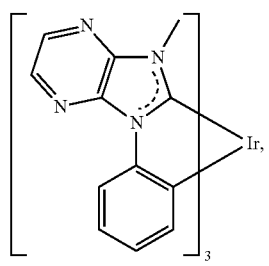

mer

Compound 6

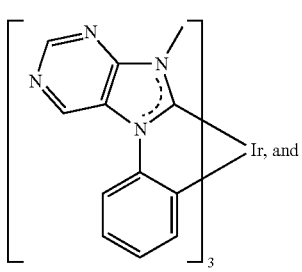

Ir, and

Compound 7

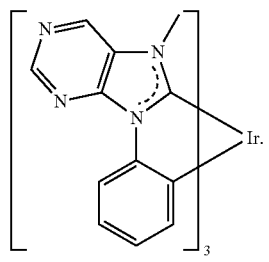

Ir.

3. The first device of claim 2, wherein the organic layer is an emissive layer and the compound is an emissive dopant.

4. The first device of claim 3, wherein the organic layer further comprises a host.

5. The first device of claim 4, wherein the host comprises at least one of the chemical groups selected from the group consisting of:

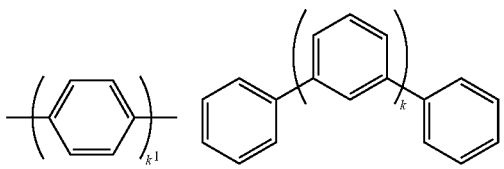

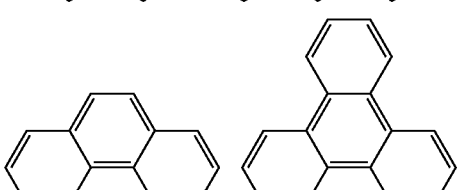

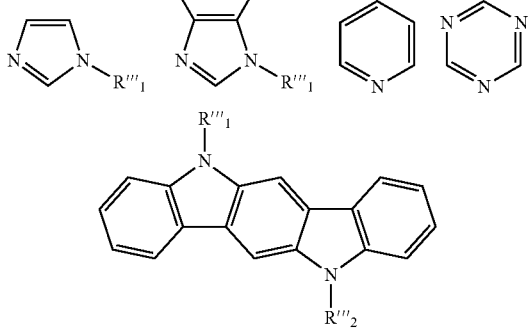

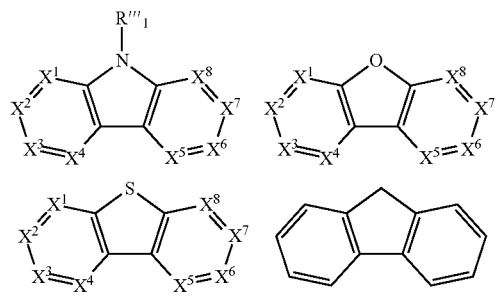

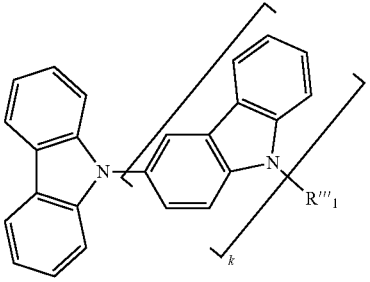

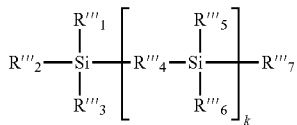

-continued

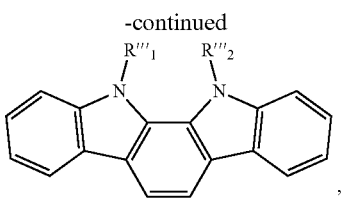

wherein each of R'''$_1$, R'''$_2$, R'''$_3$, R'''$_5$, R'''$_6$ and R'''$_7$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein R'''$_4$ is selected from the group consisting of alkylene, cycloalkylene, heteroalkylene, arylalkylene, alkenylene ether, arenylene ether, amine, silylene, alkenylene, cycloalkenylene, heteroalkenylene, alkynylene, arylene, heteroarylene, acyl, carbonyl, ester, sulfinyl, sulfonyl, phosphino, and combinations thereof;

wherein k$^1$ is an integer from 1 to 20 and k is an integer from 0 to 20; and wherein each of X$^1$, X$^2$, X$^3$, X$^4$, X$^5$, X$^6$, X$^7$ and X$^8$ are independently selected from the group consisting of CH and N.

6. The first device of claim 4, wherein the host is a metal complex.

7. The first device of claim 4, wherein the host is a metal carbene complex.

8. The first device of claim 2, wherein the first device is a consumer product.

* * * * *